(12) United States Patent
Kurane et al.

(10) Patent No.: US 7,354,707 B2
(45) Date of Patent: Apr. 8, 2008

(54) NUCLEIC ACID PROBES, METHOD FOR DETERMINING CONCENTRATIONS OF NUCLEIC ACID BY USING THE PROBES, AND METHOD FOR ANALYZING DATA OBTAINED BY THE METHOD

(75) Inventors: Ryuichiro Kurane, Tsukuba (JP); Takahiro Kanagawa, Tsukuba (JP); Yoichi Kamagata, Tsukuba (JP); Masaki Torimura, Tsukuba (JP); Shinya Kurata, Tokyo (JP); Kazutaka Yamada, Tokyo (JP); Toyokazu Yokomaku, Tokyo (JP)

(73) Assignees: National Institute of Advanced Industrial Science and Technology, Tokyo (JP); Kankyo Engineering Co., Ltd., Tokyo (JP)

( * ) Notice: Subject to any disclaimer, the term of this patent is extended or adjusted under 35 U.S.C. 154(b) by 49 days.

(21) Appl. No.: 09/891,517

(22) Filed: Jun. 27, 2001

(65) Prior Publication Data

US 2002/0106653 A1    Aug. 8, 2002

(30) Foreign Application Priority Data

| Jun. 27, 2000 | (JP) | ............................. 2000-193133 |
| Aug. 3, 2000 | (JP) | ............................. 2000-236115 |
| Sep. 26, 2000 | (JP) | ............................. 2000-292483 |

(51) Int. Cl.
*C12Q 1/68* (2006.01)
*C07H 21/00* (2006.01)
*G06F 19/00* (2006.01)

(52) U.S. Cl. .................. 435/6; 435/91.1; 435/91.2; 536/24.3; 536/24.31; 536/24.33; 702/19

(58) Field of Classification Search ............... 435/92.2; 702/19, 20
See application file for complete search history.

(56) References Cited

U.S. PATENT DOCUMENTS

| 5,753,444 A | 5/1998 | Wu et al. ....................... 435/6 |
| 5,766,889 A | 6/1998 | Atwood ..................... 435/91.2 |
| 6,699,661 B1 * | 3/2004 | Kurane et al. ................. 435/6 |
| 6,727,356 B1 * | 4/2004 | Reed et al. ................. 536/26.6 |

FOREIGN PATENT DOCUMENTS

| JP | 8-89299 | 4/1996 |
| WO | WO 99/11813 | 3/1999 |

OTHER PUBLICATIONS

Liu et al. Characterization of Microbial Diversity by Determining Terminal Restriction Fragment Length Polymorphisms of Gene Encoding 16S rRNA. Applied and Environmental Microbiology. Nov. 1997, vol. 63, No. 11, pp. 4516-4522.*
Aynacioglu et al. Population frequency, mutation linkage and analytical methodology for the Arg16Gly, Gln27Glu and Thr164Ile polymorphisms in the B2-adrenergic receptor among Turks. Journal of Clinical Pharmacology. 1999. vol. 48, pp. 761-764.*
Zhang et al. Novel TSC2 Mutation in a Patient With Pulmonary Tuberous Scelerosis: Lack of Loss Heterozygosity in a Lung Cyst. American Journal of Medical Genetics. 1999. vol. 82, pp. 368-370.*
Sreevatsan et al. Algorithmic Approach to High-Throughput Molecular Screening for Alpha Interferon-Resistant Genotypes in Hepatitis C Patients. Journal of Clinical Molecular Biology. Jul. 1998, vol. 48, pp. 1895-1901.*
Liu et al. (Applied and Environmental Microbiology (1997) November, pp. 4516-4522).*
Deborah S. Grove, Methods & Review, "Quantitative Real-Time Polymerase Chain Reaction for the Core Facility Using TaqMan and the Perkin-Elmer/Applied Biosystems Division 7700 Sequence Detector", Apr. 1999, pp. 1-15.
Perkin Elmer 9600 PE 9700 Thermal Cycler, "Perkin Elmer 9600 & 9700 PCR", 2001, pp. 1-5.

* cited by examiner

*Primary Examiner*—Lori A. Clow
(74) *Attorney, Agent, or Firm*—Oblon, Spivak, McClelland, Maier & Neustadt, P.C.

(57) ABSTRACT

Nucleic acid probes are provided, each of which is formed of a single-stranded oligonucleotide which can hybridize to a target nucleic acid and is labeled with a fluorescent dye or with a fluorescent dye and a quencher substance. The nucleic acid probes can be easily designed, permit determination, polymorphous analysis or real-time quantitative PCR of nucleic acids in short time, and are not dissociated during reactions. Nucleic acid determination methods, polymorphous analysis methods and real-time quantitative PCR methods, which make use of the nucleic acid probes, are also provided.

20 Claims, 39 Drawing Sheets

Fig. 3
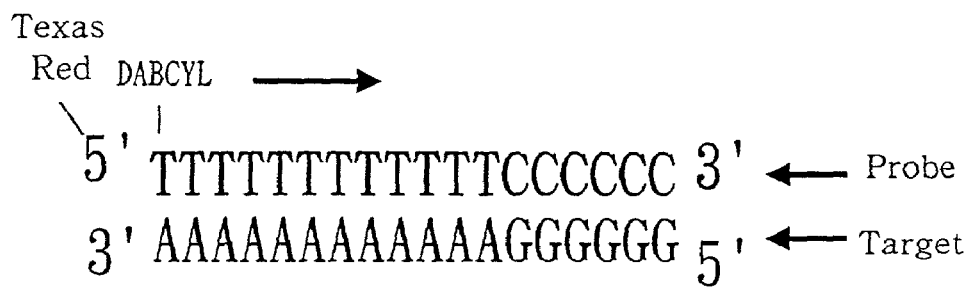
(Probe and target when the base interval is zero base)
(Probe and target when the base interval is 16 bases)

Fig. 5
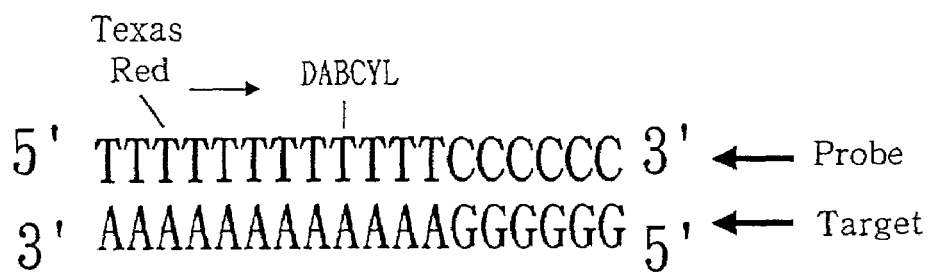
(Probe and target when the base interval is 6 bases)
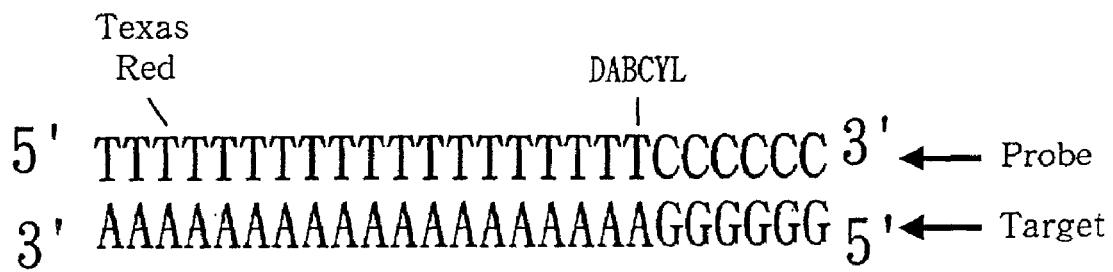
(Probe and target when the base interval is 16 bases)

Number of bases from Texas red modified on 3rd T from the 5' end to DABCYL — modified base (Value as counted supposing that the 4th base from the 5' end base is 1)

A : 35 – nucleotides – chained deoxyriboligonucleic acid probe
B : 35 – nucleotides – chained 2 – O – Me probe
C : 17 – nucleotides – chained deoxyriboligonucleic acid probe
D : 17 – nucleotides – chained 2 – O – Me probe HP : Helper probe HP + (M) : Helper probe + 2 – O – Me probe HP + (D) : Helper probe + deoxyribooligonucleotide probe Ref. : Reference

NUCLEIC ACID PROBES, METHOD FOR DETERMINING CONCENTRATIONS OF NUCLEIC ACID BY USING THE PROBES, AND METHOD FOR ANALYZING DATA OBTAINED BY THE METHOD

BACKGROUND OF THE INVENTION a) Field of the Invention

This invention relates to novel nucleic acid probes each of which is labeled with a fluorescent dye and/or a quencher substance. Specifically, a single-stranded oligonucleotide is labeled with the fluorescent dye and/or the quencher substance such that the intensity of fluorescence in a hybridization reaction system increases or decreases when the nucleic acid probe is hybridized with a target nucleic acid. This invention also relates to a method for determining a concentration of a nucleic acid by using the nucleic acid probe. The present invention is also concerned with determination kits, determination devices, and various measurement systems associated with such kits or devices. The present invention also pertains to a method for analyzing the kinds and amounts of various nucleic acids, a method for analyzing data obtained by such methods, and computer-readable recording media with procedures, which are required to have steps of the analysis method performed by a computer, recorded as a program.

b) Description of the Related Art

A variety of methods are conventionally known to determine a concentration of a nucleic acid by using a nucleic acid probe labeled with a fluorescent dye. These methods include:

(1) Dot blotting assay

After a target nucleic acid and a nucleic acid probe labeled with a fluorescent dye are hybridized on a membrane, unreacted nucleic probe is washed off. The intensity of fluorescence only from fluorescent dye molecules, by which the nucleic acid probe hybridized with the target nucleic acid is labeled, is measured.

(2) Method making use of an intercalator: Glazer et al., Nature, 359, 959, 1992

A certain specific fluorescent dye called "intercalator" emits strong fluorescence upon its insertion into a double strand of a nucleic acid. This method measures an increase in fluorescence from the fluorescent dye. Examples of the fluorescent dye can include ethidium bromide [Jikken Igaku (Laboratory Medicine), 15(7), 46-51, Yodosha (1997)] and SYBR R Green I (LightCycler™ System, Apr. 5, 1999; pamphlet distributed by Roche Diagnostics, Mannheim, Germany).

(3) Method making use of FRET (fluorescence energy transfer): Mergny et al., Nucleic Acid Res., 22, 920-928, 1994

This method comprises hybridizing two nucleic acid probes to a target nucleic acid. These two nucleic acid probes are labeled by different fluorescent dyes, respectively. The fluorescent dye of one of the two probes can transfer energy to the fluorescent dye or the other probe such that the latter fluorescent dye is caused to emit fluorescence. These two probes are designed such that they hybridize with their fluorescent dyes being located opposite each other and apart from each other by 1 to 9 bases. When these two nucleic acid probes hybridize to the target nucleic acid, emission of fluorescence from the latter fluorescent dye takes place. The intensity of this fluorescence emission is proportional to the number of replications of the target nucleic acid.

(4) Molecular beacon method: Tyagi et al., Nature Biotech., 14, 303-308, 1996

A nucleic acid probe for use in this method is labeled at an end thereof with a reporter dye and at an opposite end thereof with a quencher dye. As both end portions of the probe are complementary with each other in their base sequences, the overall base sequence of the probe is designed to form a hairpin stem. Owing to this structure, emission from the reporter dye is suppressed by the quencher dye under Forster resonant energy in a state suspended in a liquid. When the probe hybridizes to a target nucleic acid, the hairpin stem structure is broken. This leads to an increase in the distance between the reporter pigment and the quencher pigment, so that the transfer of Forster resonant energy no longer takes place. This allows the reporter dye to make emission.

(5) Davis's method: Davis et al., Nucleic Acids Res., 24, 702-706, 1996

This method uses DNA constructs containing one or two fluorescein molecules in flow cytometry. The fluorescein molecules were attached to the 3' end of a DNA probe through an 18-atom spacer arm that resulted in a 10-fold increase in fluorescence intensity compared to the DNA probe to which fluorescein was directly attached to the 3' end of the probe.

Applied to various determination methods for nucleic acids, Fish methods (fluorescent in situ hybridization assays), PCR methods, LCR methods (ligase chain reactions), SD methods (strand displacement assays), competitive hybridization and the like, significant developments have been made on these methods.

(6) Substantial technical improvements have been made on methods for amplifying a target gene by PCR [Tanpakushitsu, Kakusan, Koso (Proteins, Nucleic Acids, Enzymes), 35(17), KYORITSU SHUPPAN CO., LTD. (1990)] and conducting a polymorphous analysis on the target gene so amplified, and these polymorphous analysis methods have now found wide-spread utility in various fields such as medical field [Jikken Igaku (Laboratory Medicine), 15(7), Yodosha (1997)]. Various diseases, especially immune-related diseases have hence been elucidated from genes, thereby obtaining certain successful outcomes.

Although these methods are now widely used, they include a disadvantageous step that, subsequent to hybridization reaction between a nucleic acid probe labeled with a fluorescent dye and a target nucleic acid, an unhybridized portion of the nucleic acid probe has to be washed out of the reaction system. Obviation of this step can apparently bring about shorter determination time, simplified determination, and accurate determination. There is, accordingly, a long-standing desire for the development of a nucleic acid determination method which does not include such a step.

SUMMARY OF THE INVENTION

With the foregoing in view, the present invention has as an object thereof the provision of a method for determining a concentration of a target nucleic acid by using a nucleic acid probe labeled with a fluorescent dye, which makes it possible to determine the concentration of the target nucleic acid in a shorter time, more easily and more accurately, and also the provision of nucleic acid probes useful for the practice of the method and various devices making use of the probes.

The present invention also has as a second object thereof the provision of a novel polymorphous analysis method for easily and quickly performing determination of a polymorphous composition of a target gene and reagent kits useful in the method, a computer-readable recording medium with programmed procedures, which are required to make a computer perform a method for analyzing data obtained by the quantitative polymorphous analysis method, and an analysis system for the quantitative polymorphous analysis.

To achieve the above-described objects, the present inventors have proceeded with a variety of investigations and have obtained findings as will be described below.

A detailed study was conducted on a variety of nucleic acid probes, and in a trial and error manner, many probes were prepared. As a result, it has been found that, even in the case of a nucleic acid probe composed of an oligonucleotide which does not form a stem-loop structure between nucleotide chains at positions where the oligonucleotide is labeled with a fluorescent dye and a quencher substance, respectively, labeling by the dye and substance at specific positions may allow the quencher substance to act on the emission of fluorescence from the fluorescent dye and may give quenching effect on the emission of fluorescence.

The present inventors have proceeded with an investigation on methods for determining a concentration of a nucleic acid by using a nucleic acid probe. As a result, it was found that emission of fluorescence from a fluorescent dye decreases (quenching phenomenon of fluorescence) when a nucleic acid probe labeled with the fluorescent dye hybridizes to a target nucleic acid. It was also found that this decrease is significant with certain specific dyes. It was also found that the extent of this decrease varies depending on bases in a probe portion, to which the fluorescent dye is conjugated, or on the sequence of the bases.

Performance of a polymorphous analysis on a target gene after amplifying the target gene by a quantitative gene amplification method makes it possible to easily and quickly determine the pre-amplification amount and polymorphous composition of the target gene with good quantitativeness.

The present invention has been completed based on the above-described findings.

Therefore, the present invention provides the following (novel) nucleic acid probes, methods, kits and devices:

1) A novel nucleic acid probe for determining a concentration of a target nucleic acid, comprising:
   a single-stranded oligonucleotide capable of hybridizing to the target nucleic acid, and
   a fluorescent dye and a quencher substance, both of which are labeled on the oligonucleotide,
   wherein the oligonucleotide is labeled with the fluorescent dye and the quencher substance such that an intensity of fluorescence in a hybridization reaction system increases when the nucleic acid probe is hybridized with the target nucleic acid; and the oligonucleotide forms no stem-loop structure between bases at positions where the oligonucleotide is labeled with the fluorescent dye and the quencher substance, respectively.

2) A nucleic acid probe for determining a concentration of a target nucleic acid, the probe being labeled with a fluorescent dye, wherein:
   the probe is labeled at an end portion thereof with the fluorescent dye, and
   the probe has a base sequence designed such that, when the probe hybridizes at the end portion thereof to the target nucleic acid, at least one G (guanine) base exists in a base sequence of the target nucleic acid at a position 1 to 3 bases from an end base of the target nucleic acid hybridized with the probe;
   whereby the fluorescent dye is reduced in fluorescence emission when the probe labeled with the fluorescent dye hybridizes to the target nucleic acid.

3) A nucleic acid probe for determining a concentration of a target nucleic acid, the probe being labeled with a fluorescent dye, wherein:
   the probe is labeled at an end portion thereof with the fluorescent dye, and
   the probe has a base sequence designed such that, when the probe hybridizes to the target nucleic acid, plural base pairs in a probe-nucleic acid hybrid complex form at least one G (guanine) and C (cytosine) pair at the end portion;
   whereby the fluorescent dye is reduced in fluorescence emission when the probe labeled with the fluorescent dye hybridizes to the target nucleic acid.

4) A nucleic acid probe for determining a concentration of a target nucleic acid, the probe being labeled with a fluorescent dye, wherein:
   the probe is labeled at a modification portion other than a 5' end phosphate group or a 3' end OH group thereof with the fluorescent dye, and
   the probe has a base sequence designed such that, when the probe hybridizes to the target nucleic acid, plural base pairs in a probe-nucleic acid hybrid complex form at least one G (guanine) and C (cytosine) pair at the modification portion;
   whereby the fluorescent dye is reduced in fluorescence emission when the probe labeled with the fluorescent dye hybridizes to the target nucleic acid.

5) A nucleic acid probe as described above under any one of 1) to 4) for determining a concentration of a nucleic acid, wherein the oligonucleotide of the nucleic acid probe for the measurement of the nucleic acid is a chemically-modified nucleic acid.

6) A nucleic acid probe as described above under any one of 1) to 5) for determining a concentration of a target nucleic acid, said nucleic acid probe being labeled with a fluorescent dye, wherein the oligonucleotide of the nucleic acid probe for the determination of the nucleic acid is a chimeric oligonucleotide which comprises a ribonucleotide and a deoxyribonucleotide.

7) A method for determining a concentration of a target nucleic acid, which comprises:
   hybridizing a nucleic acid probe as described above under any one of 1) to 6) to the target nucleic acid, and
   measuring an intensity of fluorescence in a measuring system.

8) A method for determining a concentration of a target nucleic acid, which comprises:
   hybridizing a nucleic acid probe as described above under any one of 1) to 6) to the target nucleic acid, and
   measuring a change in fluorescence emission from the fluorescent dye after the hybridization relative to fluorescence emission from the fluorescent dye before the hybridization.

9) A method for determining a concentration of a target nucleic acid by using a nucleic acid probe as described above under any one of 1) to 6), wherein the nucleic acid probe and the target nucleic acid are hybridized to each other after subjecting the target nucleic acid to heat treatment under conditions suited for sufficient degradation of a high-order structure of the target nucleic acid.
10) A method as described above under 9) for measuring a concentration of a target nucleic acid, wherein a helper probe for the practice of a hybridization reaction is added to a hybridization reaction system before the hybridization reaction.
11) A method for analyzing or determining polymorphism and/or mutation of a target nucleic acid, which comprises:
hybridizing a nucleic acid probe as described above under any one of 1) to 6) to the target nucleic acid, and measuring a change in an intensity of fluorescence.
12) A novel quantitative, polymorphous analysis method comprising:
amplifying a target gene by a quantitative gene amplification method; and
performing a polymorphous analysis with respect to the target gene to determine an amount of the target gene and a polymorphous composition or amounts of individual components of the target gene.
13) A quantitative, polymorphous analysis method as described above under 12), wherein the polymorphous analysis is T-RELP (terminal restriction fragment length polymorphism), RFLP restriction fragment length polymorphism), SSCP (single strand conformation) or CFLP (cleavage fragment length polymorphism).
14) A quantitative, polymorphous analysis method as described above under 12) or 13), wherein the quantitative gene amplification method is quantitative PCR or real-time monitoring quantitative PCR.
15) A kit for determining a concentration of a target nucleic acid, wherein the kit includes or is accompanied by a nucleic acid probe as described above under any ore of 1) to 6) or a nucleic acid probe and a helper probe as described above under any one of 1) to 6).
16) A kit for analyzing or determining polymorphism and/or mutation of a target nucleic acid, comprising a nucleic acid probe as described above under any one of 1) to 6) or a nucleic acid probe and a helper probe as described above under any one of 1) to 6).
17) A reagent kit for use in quantitative PCR, wherein the kit includes or is accompanied by a nucleic acid probe as described above under any one of 1) to 6) or a nucleic acid probe and a helper probe as described above under any one of 1) to 6).
18) A device for determining a concentration of at least one target nucleic acid out of plural nucleic acids, comprising:
a solid support, and
a like plural number of nucleic acid probes as described above under any one of 1) to 6) bound on a surface of the solid support such that the concentration of the target nucleic acid can be determined by hybridizing the target nucleic acid to the corresponding one of the probes and determining a change in an intensity of fluorescence.
19) A method for determining a concentration of a target nucleic acid, which comprises determining the concentration of the target nucleic acid or analyzing or determining polymorphism and/or mutation of the target nucleic acid by using a nucleic acid determination device as described above under 18), or a quantitative, polymorphous analysis method of a target nucleic acid, which comprises performing a quantitative, polymorphous analysis of the target nucleic acid by using a nucleic acid determination device as described above under 18).
20) A nucleic acid determination method, a method for analyzing or determining polymorphism and/or mutation of a target nucleic acid, or a quantitative, polymorphous analysis method as described above under any one of 7) to 14), wherein the target nucleic acid is a nucleic acid contained in cells derived from a microorganism or animal obtained by single colony isolation or a nucleic acid contained in a homogenate of the cells.
21) A method for determining a concentration of a target nucleic acid by using PCR, which comprises:
conducting reactions in PCR by using a nucleic acid probe as described above under any one of 1) to 6), and
determining an initial concentration of the amplified target nucleic acid from percentage of a change in an intensity of fluorescence occurred as a result of hybridization between the probe and the amplified target nucleic acid.
22) A method for determining a concentration of a target nucleic acid by using PCR, which comprises:
conducting reactons in PCR by using as a primer a nucleic acid probe as described above under any one of 1) to 6), and
determining an initial concentration of the amplified target nucleic acid from percentage of a change in an intensity of fluorescence occurred as a result of hybridization between the primer or an amplified nucleic acid amplified from the primer and the amplified target nucleic acid.
23) A method for determining an initial concentration of a target nucleic acid amplified in PCR, which comprises:
conducting reactions in PCR by using a nucleic acid probe as described above under any one of 1) to 6);
measuring an intensity of fluorescence in a reaction system in which in a course of a nucleic acid extending reaction, the probe has been degraded out from the probe-target nucleic acid complex by polymerase or in which a nucleic acid denaturing reaction is proceeding or has been completed and also an intensity of fluorescence in the reaction system in which the target nucleic acid or amplified target nucleic acid is hybridized with the nucleic acid probe; and then calculating percentage of a change in the latter intensity of fluorescence from the former intensity of fluorescence.
24) A method for determining an initial concentration of a nucleic acid amplified in PCR, which comprises:
conducting reactions in PCR by using, as a primer, a nucleic acid probe as described above under any one of 1) to 6);
measuring an intensity of fluorescence in a reaction system in which the probe and the target nucleic acid or amplified nucleic acid have not hybridized with each other and also an intensity of fluorescence in the reaction system in which the probe and the target nucleic acid or amplified nucleic acid are hybridized with each other; and then
calculating percentage of a decrease of the former intensity of fluorescence from the latter intensity of fluorescence.
25) A method as described above under 23) or 24) for determining a concentration of a nucleic acid amplified in PCR, wherein the PCR is real-time quantitative PCR.
26) A method for analyzing data obtained by a nucleic acid determination method as described above under any one of 23) to 25), further comprising correcting an intensity value of fluorescence in a reaction system, said intensity value being available after the target nucleic acid has hybridized to the nucleic acid probe labeled with the fluorescent dye, in accordance with an intensity value of fluorescence in the reaction system available after a probe-nucleic acid hybrid complex so formed has been denatured.

27) A method for analyzing data obtained by a real-time quantitative PCR method as described above under any one of 23) to 25), further comprising, as a correction processing step, correcting an intensity value of fluorescence in a reaction system, said intensity being available in each cycle after the amplified nucleic acid has conjugated to the fluorescent dye or after the amplified nucleic acid has hybridized to the nucleic acid probe labeled with the fluorescent dye, in accordance with an intensity value of fluorescence in the reaction system available after a nucleic acid-fluorescent dye conjugate or probe-nucleic acid hybrid complex so formed has been denatured in the cycle.

28) A method for analyzing a melting curve of a target nucleic acid, which comprises:
  performing PCR on the target nucleic acid by using a nucleic acid probe as described above under to any one of 1) to 6); and
  analyzing the melting curve of the target nucleic acid to determine a Tm value of each amplified nucleic acid.

Numerous advantageous effects have been brought about by the present invention as will be set out below.

1) First Aspect of the Invention (Fluorescence Emitting Probe)

As the probe according to the present invention has been obtained by simply binding the fluorescent dye and the quencher substance to the single-stranded deoxyribooligonucleotide which does not form any stem loop, the designing of the base sequence of a probe which hybridizes to a target nucleic acid is not complex and is easy. Further, the emission of fluorescence from the fluorescent dye is suppressed by the quencher substance before the probe hybridizes to the target nucleic acid, so that the background of a measurement is extremely low. Accordingly, the measurement of the target nucleic acid is accurate. Moreover, the measurement is simple and can be conducted in a short time.

2) Second Aspect of the Invention (Fluorescence Quenching Probe)

(1) The probe according to the present invention has been obtained by simply binding the specific fluorescent dye to the single-stranded deoxyribooligonucleotide. The probe is designed such that the intensity of fluorescence decreases when the reaction system changes from a non-hybridization system to a hybridization system. Therefore, the designing of the probe is not complex and is easy. As a consequence, the measurement of a target nucleic acid is accurate and simple.

(2) In particular, the fluorescence quenching probe according to the present invention, which comprises the chemically-modified oligonucleotide or the like, or the fluorescence quenching probe according to the present invention, which comprises the chimeric oligonucleotide, has been developed for the determination of RNA having a complex structure, especially a nucleic acid such as tRNA. This invention has made it possible to determine such a nucleic acid easily, simply and accurately.

3) Third Aspect of the Present Invention (the Invention Relating to Use of He Above-Described Fluorescence Emitting Probe and Fluorescence Quenching Probe According to the Present Invention)

(1) Use of fluorescence emitting probes or fluorescence quenching probes according to the present invention makes it possible to simply and easily produce a determination kit for determining a concentration of a target nucleic acid, said kit including or being accompanied by such probes, or a nucleic acid chip or nucleic acid device such as a DNA chip with the probes bound thereon.

(2) Since use of the method, determination kit, nucleic acid chip or nucleic acid device according to the present invention does not require an operation such as that needed to remove unreacted nucleic acid probe from a determination system, the concentration of a target nucleic acid can be determined in a short time and with ease.

(3) When applied to a co-cultivation system of microorganisms or a symbiotic cultivation system of microorganisms, the viable count of a particular microorganism strain in the system can be specifically measured in a short time.

(4) Further, the present invention has also made it possible to simplify, with improved accuracy, determination of polymorphism, such as SNP (single nucleotide polymorphism), or mutation of a target nucleic acid.

(5) Further, the quantitative PCR method making use of probes of the present invention has the following advantageous effects:
  a. As the quantitative PCR method does not involve addition of any factor which may act in an inhibitive manner on amplification of a target nucleic acid by Taq DNA polymerase, quantitative PCR can be conducted under similar conditions as conventionally-known usual PCR having specificity.
  b. The specificity of PCR can be maintained high, so that amplification of primer dimer is retarded. Compared with conventionally-known quantitative PCR, the quantitation limit can he lowered on the order of about one digit.
  c. It is no longer required to provide a complex nucleic acid probe. It is, therefore, possible to save time and cost which would otherwise be required for such a complex nucleic acid probe.
  d. A target nucleic acid can be effectively amplified, so that the amplification step can be monitored in real time.

(6) The present invention has also provided the method for analyzing data obtained by real-time quantitative PCR which makes use of fluorescence emitting probes or fluorescence quenching probes according to the present invention.

(7) The data analysis method according to the present invention can be used to prepare a working line for the determination of the number of copies of a nucleic acid in a nucleic acid sample of unknown nucleic acid copy number. This working line has a correlation coefficient which is far higher than those available by conventional methods. Use of the data analysis method according to the present invention, therefore, makes it possible to accurately determine the number of copies of nucleic acid.

(8) A working line the correlation efficient of which is high can be automatically prepared by the use of the data analysis software relating to the analysis method of data obtained by real-time quantitative PCR, the computer-readable recording medium with the procedures of the analysis method recorded as a program therein, or the determination or analysis system for the real-time quantitative PCR. The data analysis software, computer-readable recording medium, and the determination or analysis system all pertain to the present invention.

(9) Further, use of the novel method according to the present invention for the analysis of the melting curve of a nucleic acid makes it possible to determine the Tm value of the nucleic acid with high accuracy. Moreover, use of the data analysis software for the method, the computer-readable recording medium with the procedures of the analysis method recorded as a program therein, or the determination or analysis system for the real-time quantitative PCR makes it possible to obtain an accurate Tm value.

(10) Quantitative, polymorphous analysis method

Determination of the amount of a target gene or the polymorphous composition of the gene is performed with respect to the nucleic acid after amplifying the nucleic acid by the novel quantitative PCR method of the present invention. The amplified nucleic acid is modified with the fluorescent dye. As the fluorescent dye can be analyzed as a marker in the polymorphous analysis, the polymorphous analysis can be conducted easily and quickly with good quantitativeness.

BRIEF DESCRIPTION OF THE DRAWINGS

FIG. 4 is a diagram illustrating effects of the distance (the number of bases) between the fluorescent dye (Texas Red) and the quencher substance (Dabcyl) on the emission of fluorescence from the fluorescence emitting probe making use of interaction between the fluorescent dye and the quencher substance, in which:

Figure 6:
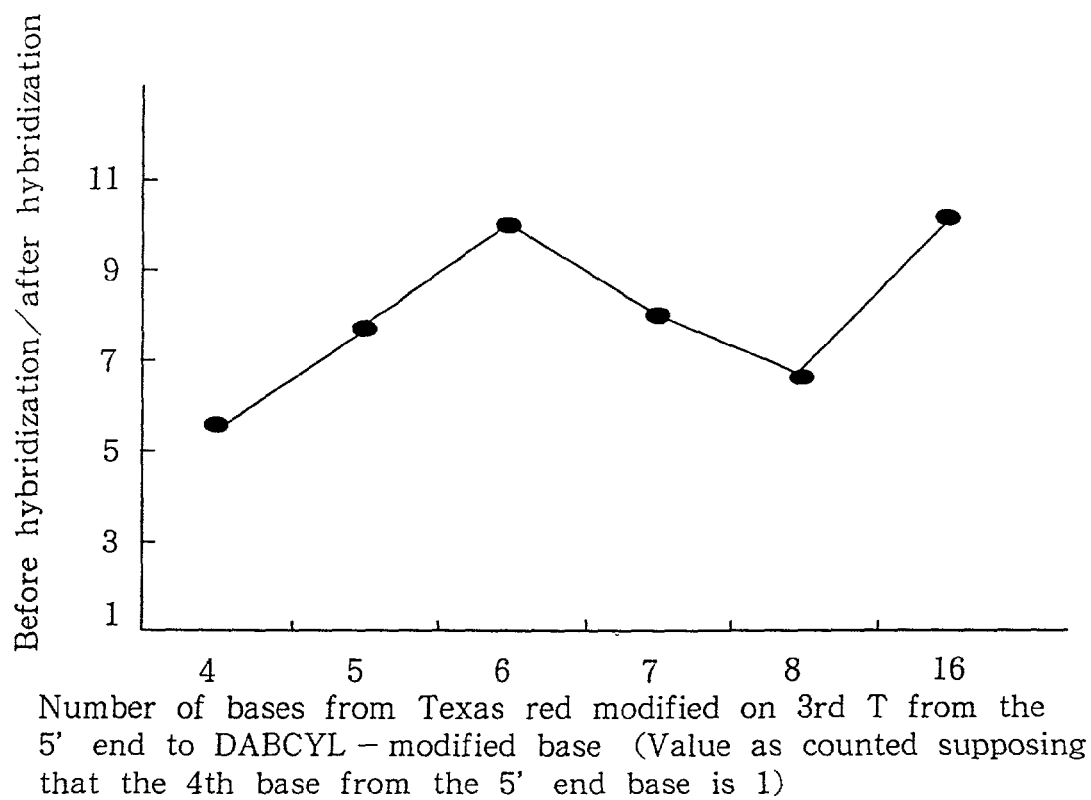
Figure 7:
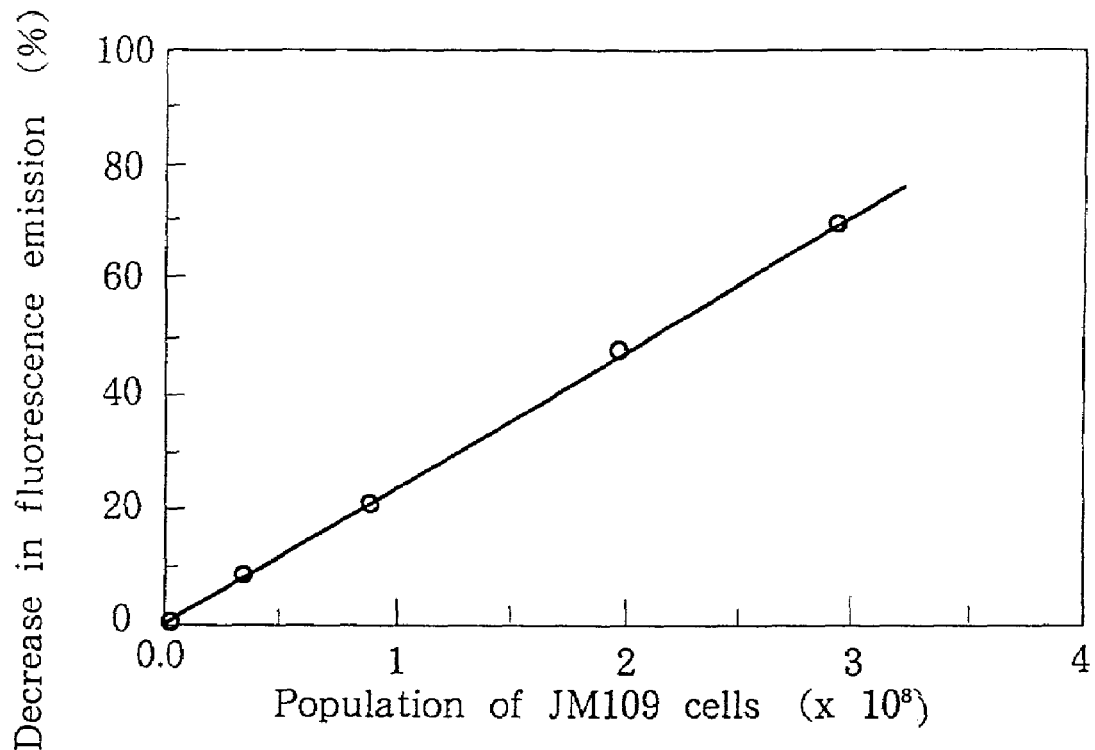
Figure 8:
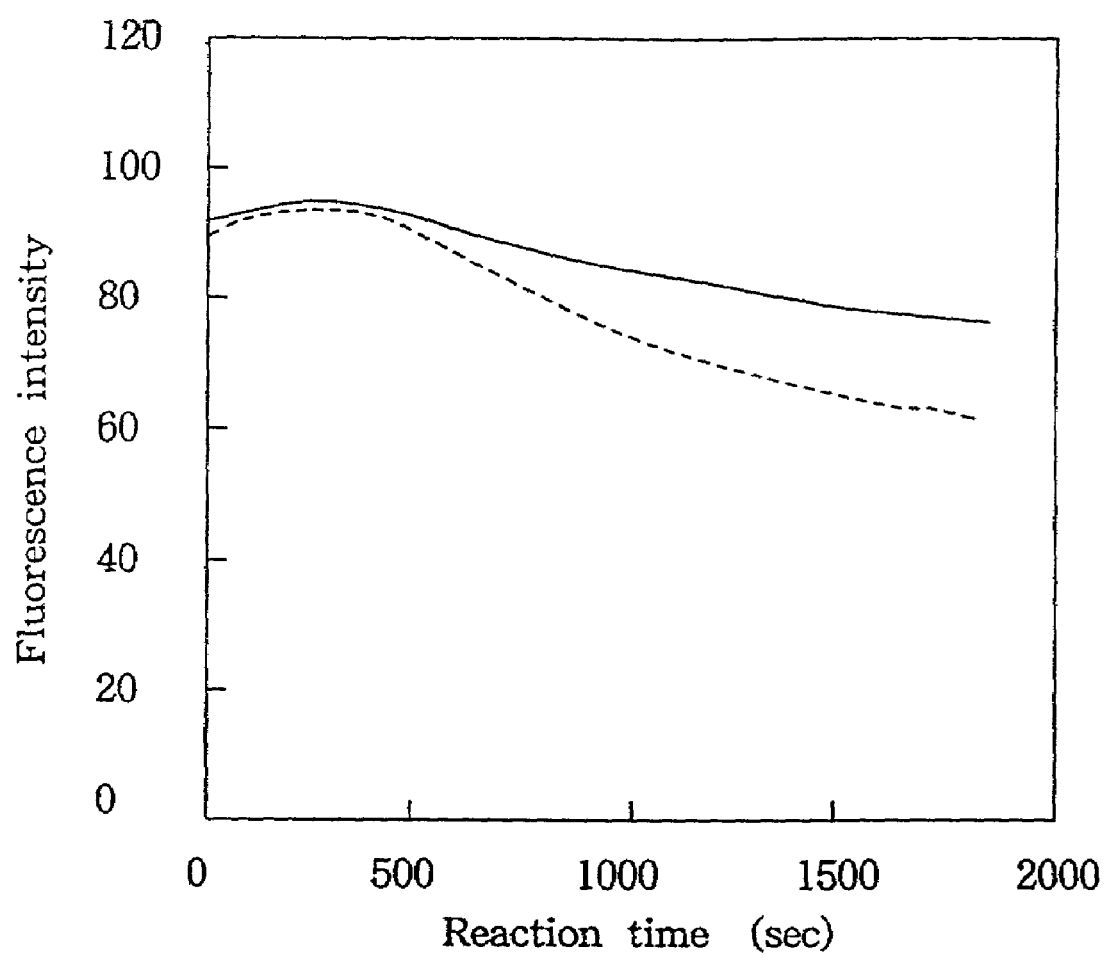
Figure 9:
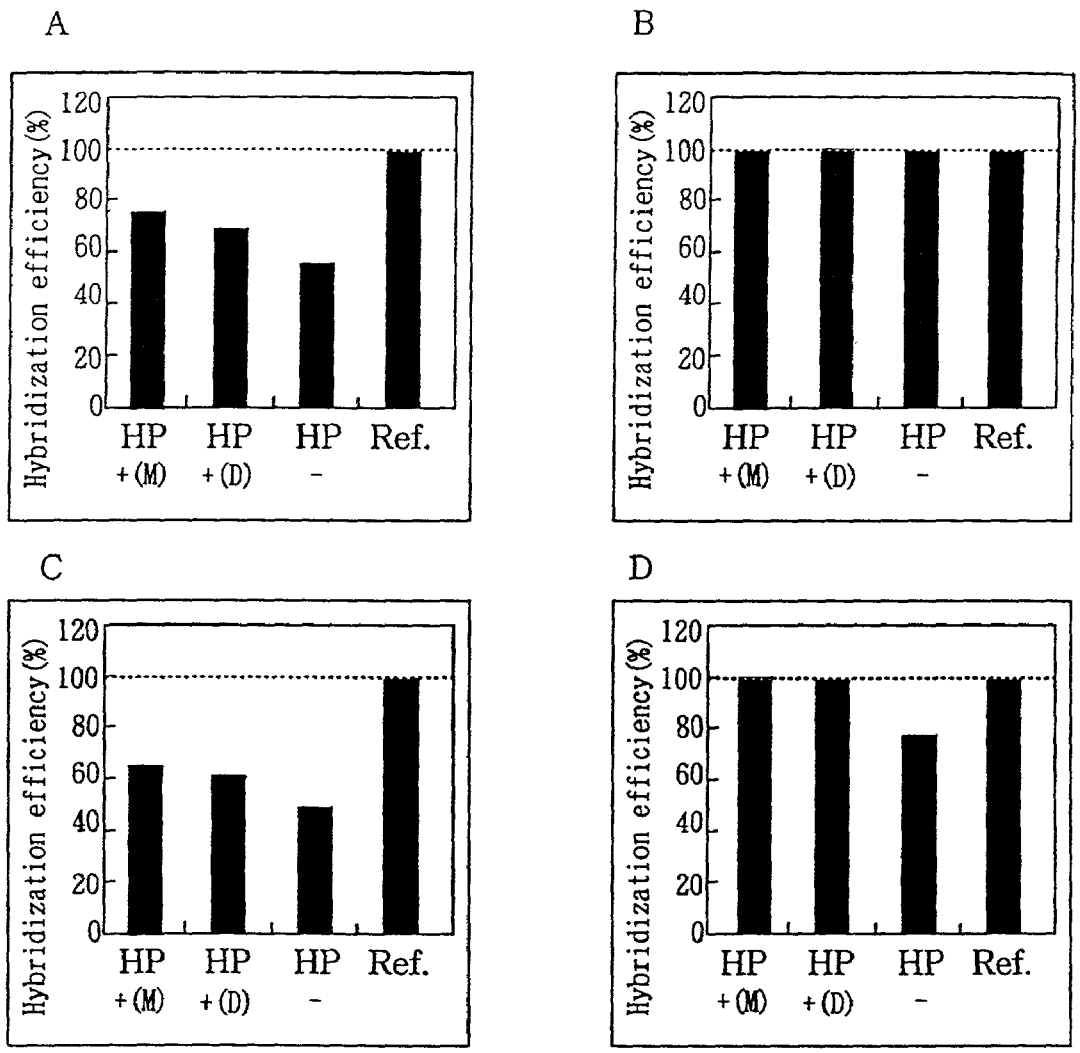

Open column: Fluorescence intensity after hybridization (absolute value of fluorescence intensity, measuring wave length: 623.5 nm), Closed column: Fluorescence intensity before hybridization (absolute value of fluorescence intensity, measuring wave length: 623.5 nm), —●—: Fluorescence intensity before hybridization/fluorescence intensity after hybridization;

FIG. 5 illustrates probe designs, in each of which bases in a deoxyribooligonucletide chain were modified with both fluorescent dye (Texas Red) and quencher substance (Dabcyl), respectively, and target nucleic acid designs. In the top half of FIG. 5, the sequence (5'→3') is that of SEQ ID NO: 109. In the bottom half of FIG. 5, the sequence (5'→3') is that of SEQ ID NO: 110;

FIG. 6 is a diagram illustrating effects of the distance (the number of bases) between the fluorescent dye (Texas Red) and the quencher substance (Dabcyl) on the emission of fluorescence as observed using a probe in which bases in a deoxyribooligonucletide chain were modified with both of the fluorescent dye and the quencher substance, respectively;

FIG. 7 is a diagram showing measurement data of fluorescence intensity when the sequence of bases in 16S rRNA of *Escherichia coli*, said bases ranging from the $335^{th}$ base to the $358^{th}$ base as counted from the 5' end, was determined using a nucleic acid probe obtained in Example 7;

FIG. 8 diagrammatically illustrates effects of heat treatment of a target nucleic acid on hybridization of a 35-nucleotides-chained 2-O-Me probe to the target nucleic acid, in which:

Dashed curve: rRNA was added as a target nucleic acid subsequent to its heat treatment, and Solid curve: rRNA not subjected to heat treatment;

FIG. 9 diagrammatically shows effects of the number of bases in a nucleotide chain of a probe, a helper probe and methylation of an OH group on the 2' carbon of ribose at the 5' end of the probe on the hybridization between the probe and a target nucleic acid, 16S rRNA, in which:

Ref: Reference

In the references of the probes A,B, 35-base oligonucleotide was used as a target nucleic acid.

Figure 10:
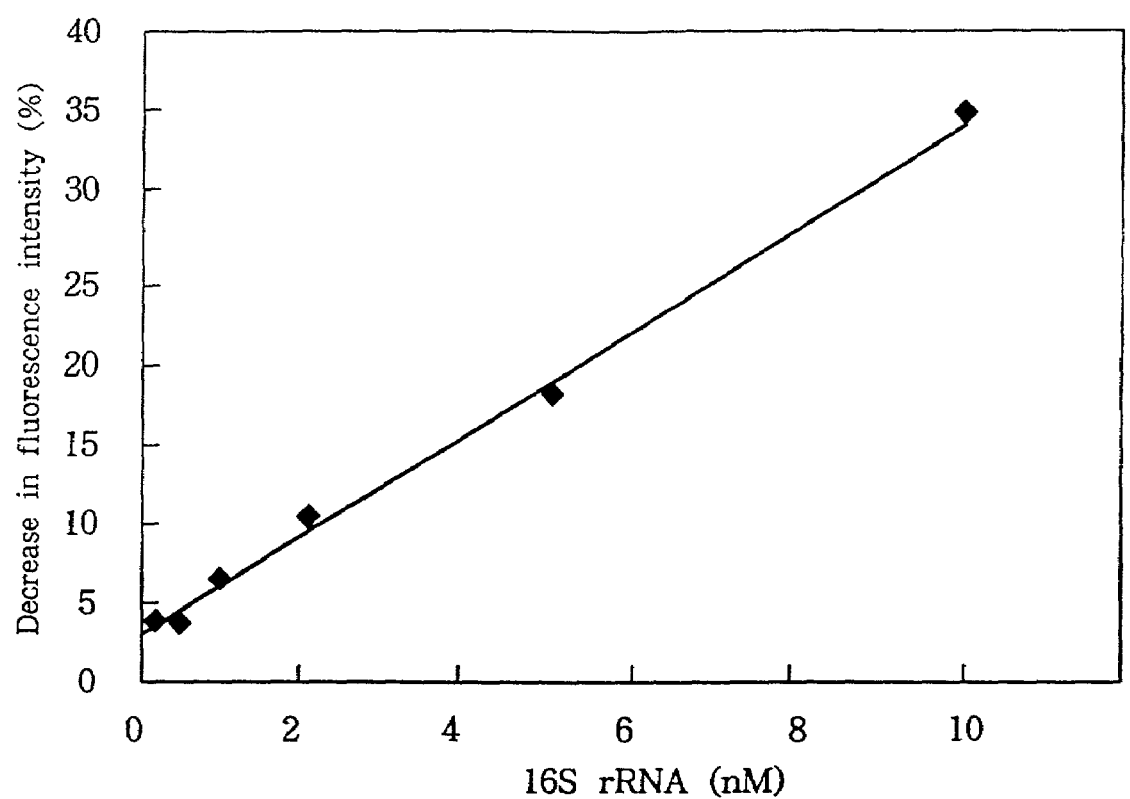
Figure 11:
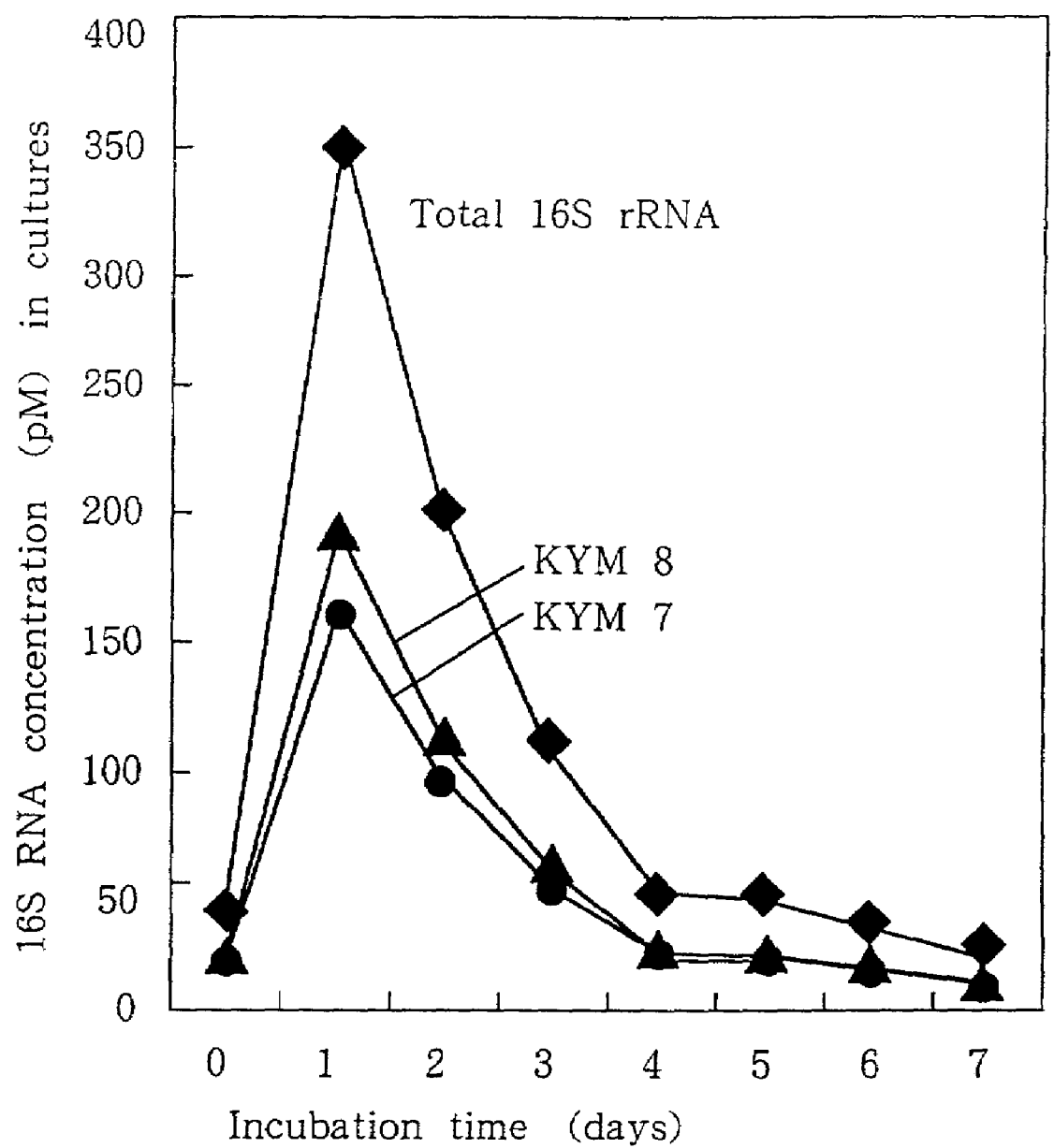
Figure 12:
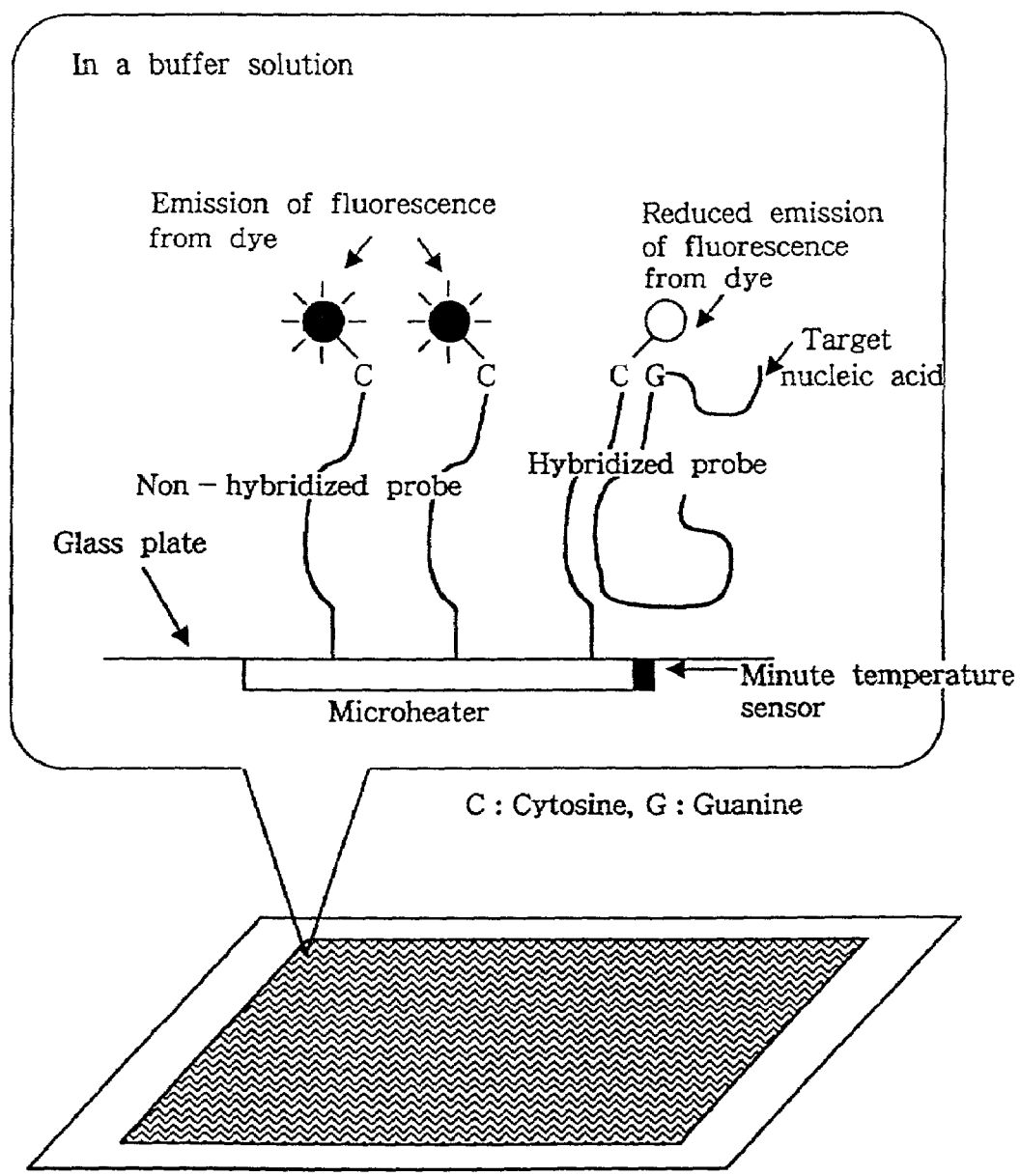
Figure 13:
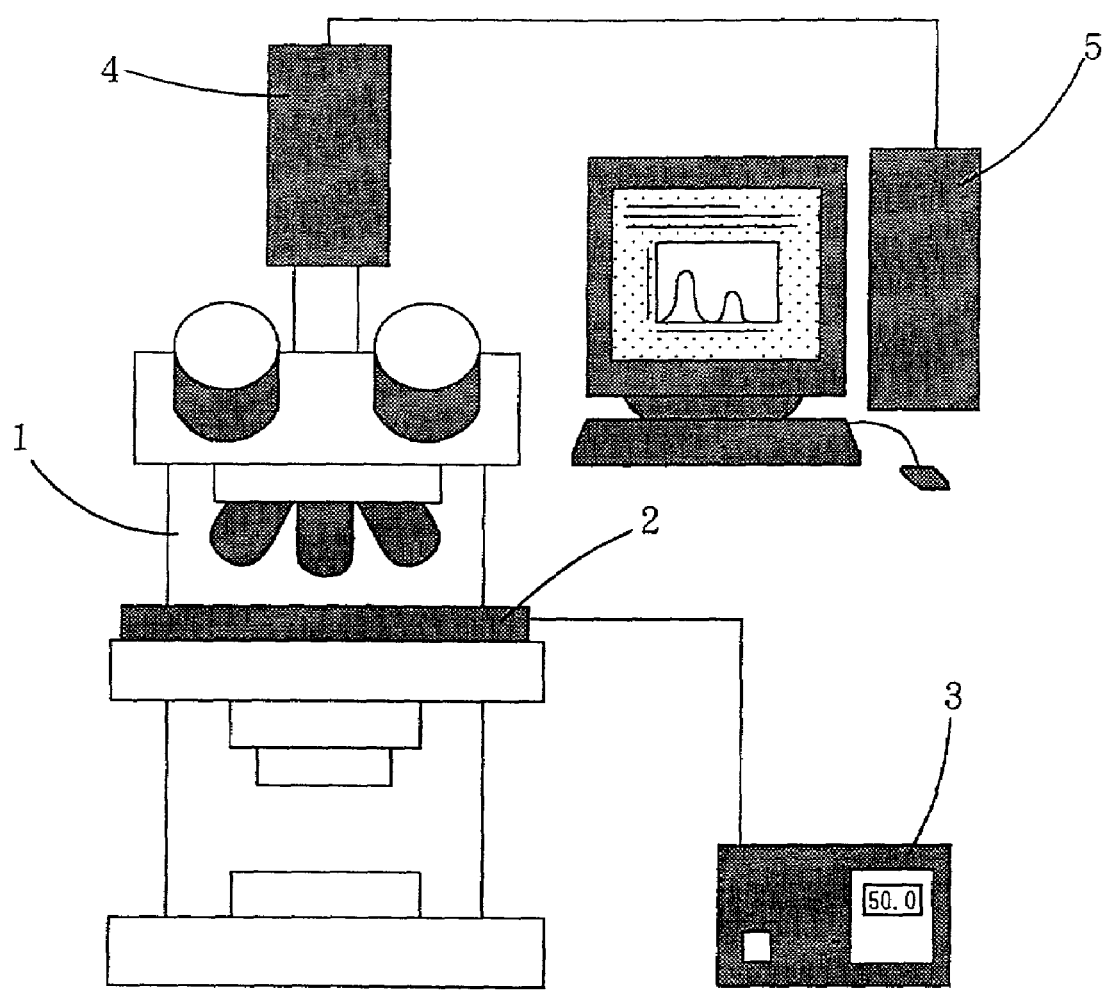
Figure 14:
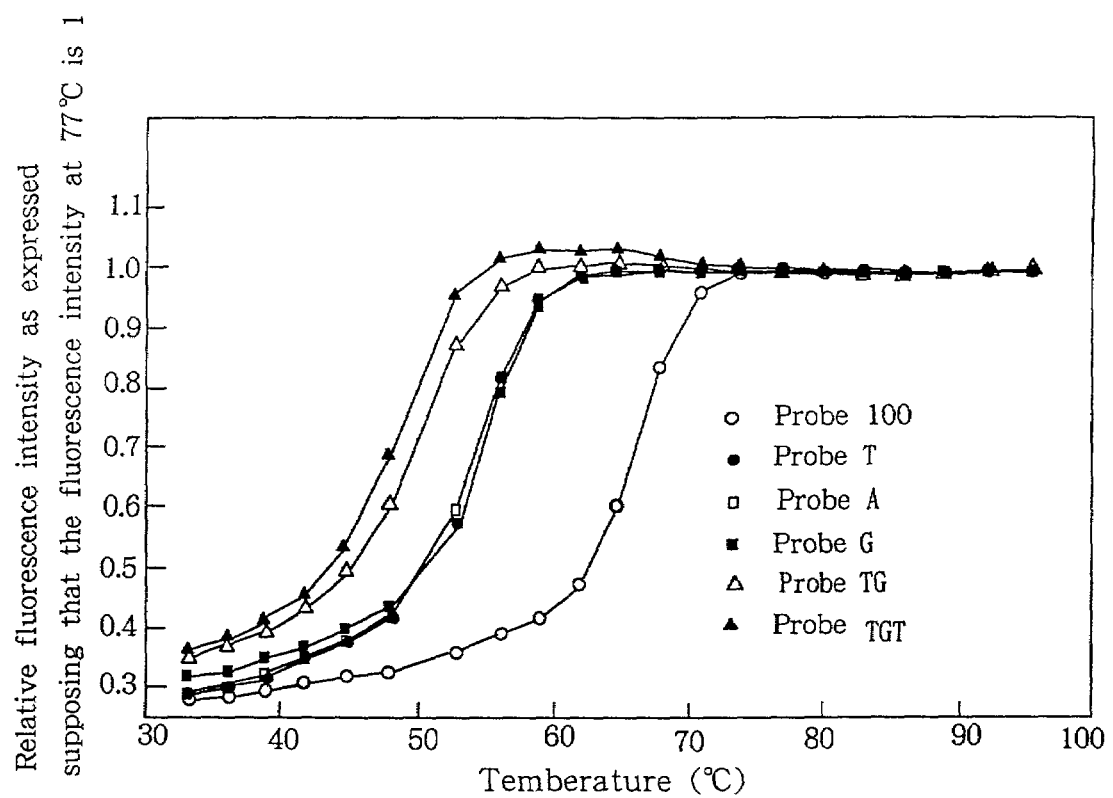
Figure 15:
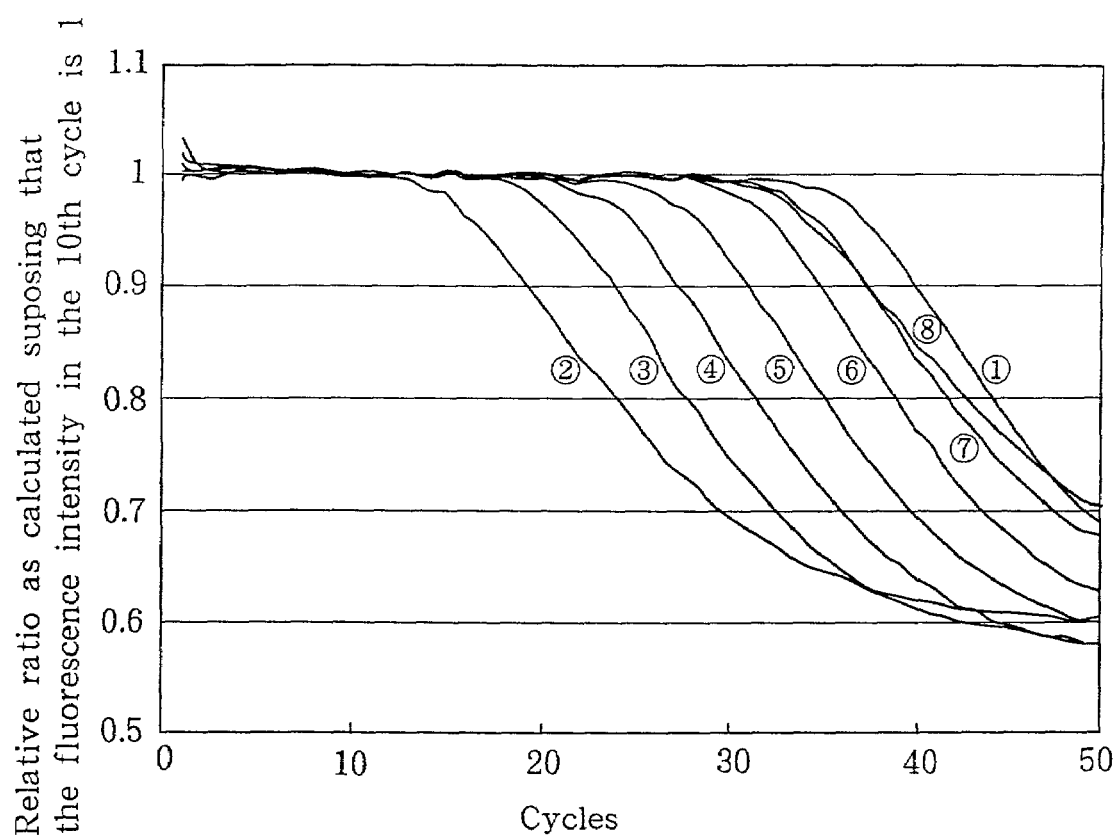

In the references of the probes C,D, 17-base oligonucleotide was used as a target nucleic acid;

FIG. 10 shows a working curve for rRNA assay by an invention method;

FIG. 11 diagrammatically shows analysis results of the time-dependent rRNA amount of strains, KYM-7 and KYM-8, in co-cultivation by a FISH method according to the present invention;

FIG. 12 is a schematic illustration of a DNA chip according to the present invention, in which MP-10MH-PG microheaters were used;

FIG. 13 is a schematic illustration of equipment for an SNAPs detection or determination making use of the DNA chip according to the present invention;

FIG. 14 is a diagram showing experimental results of the SNAPs detection or determination making use of the DNA chip according to the present invention;

FIG. 15 diagrammatically illustrates a relationship between cycles and a decrease in fluorescence emission from a fluorescent dye in a quantitative PCR method making use of primers 1 and 2 labeled with "BODIPY FL/C6", in which signs ① to ⑧ have the following meanings:

① Number of copies of *E. coli* genome DNA: 0; primer: primer 1+primer 2.

② Number of copies of *E. coli* genome DNA: $2.4 \times 10^6$; primer: same as above.

③ Number of copies of *E. coli* genome DNA: $2.4 \times 10^5$; primer: same as above.

④ Number of copies of *E. coli* genome DNA: $2.4 \times 10^4$; primer: same as above.

⑤ Number of copies of *E. coli* genome DNA: $2.4 \times 10^3$; primer: primer 1.

⑥ Number of copies of *E. coli* genome DNA: $2.4 \times 10^2$; primer: same as above.

⑦ Number of copies of *E. coli* genome DNA: $2.4 \times 10^1$; primer: same as above.

⑧ Number of copies of *E. coli* genome DNA: $2.4 \times 10^0$; primer: same as above.

Figure 16:
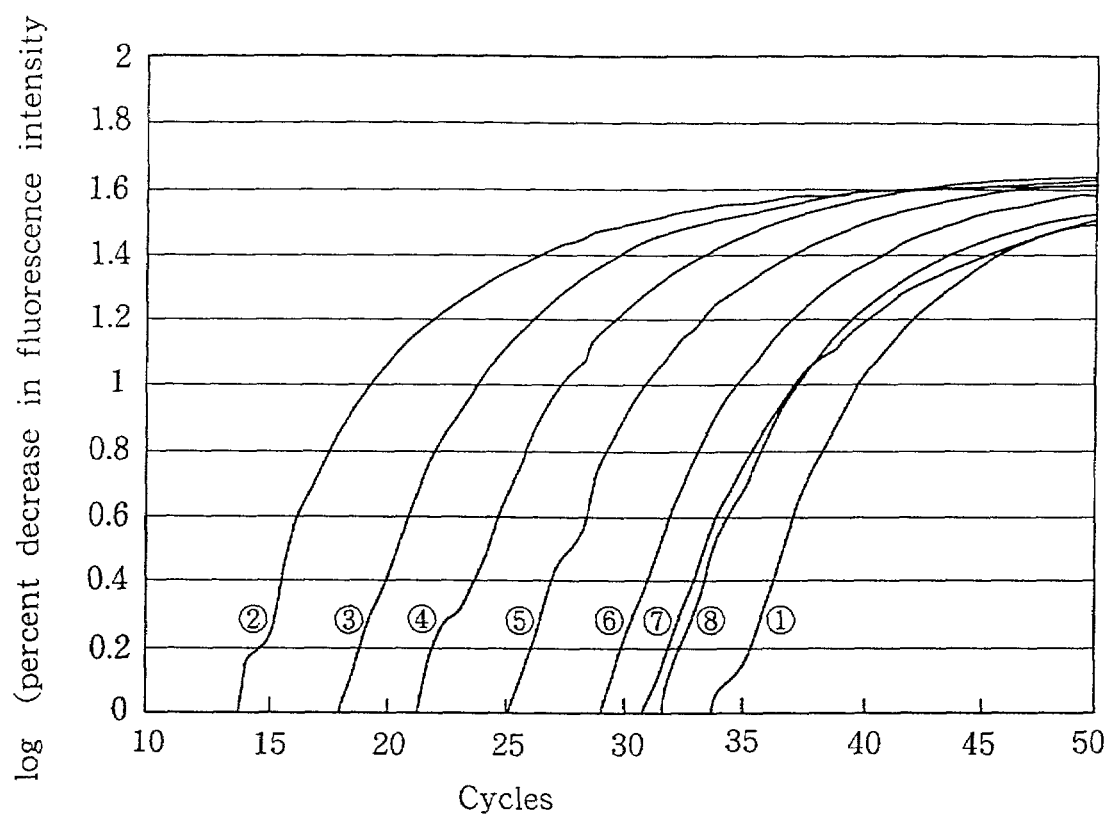
Figure 17:
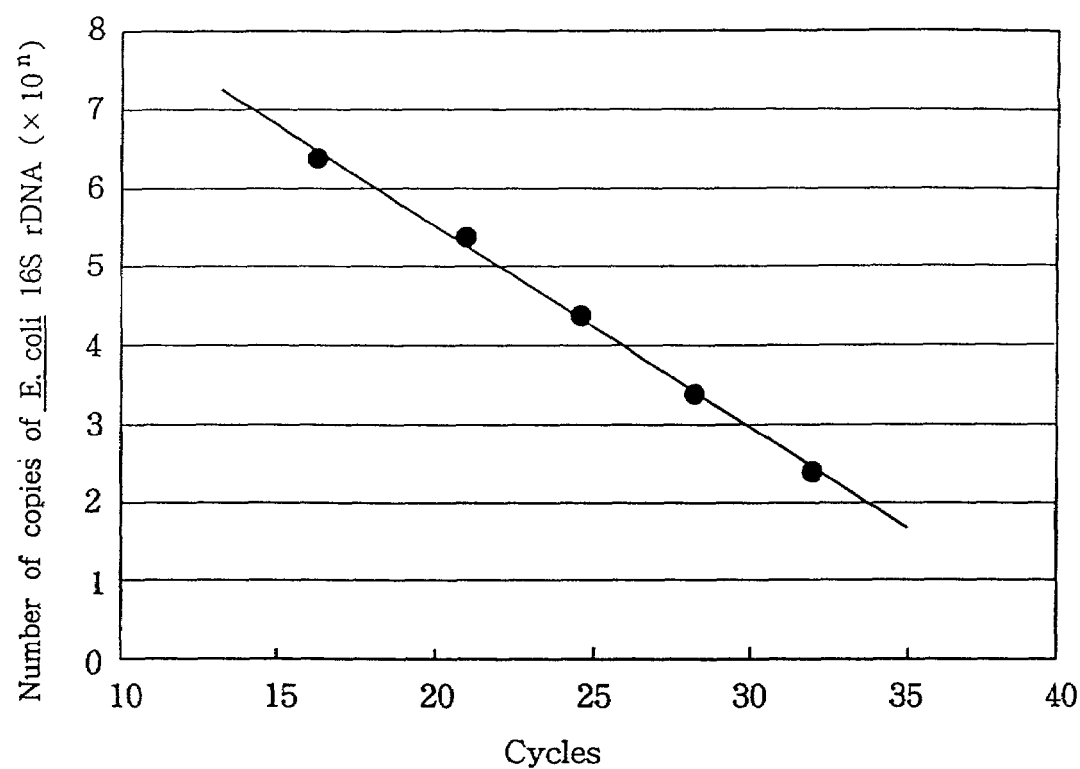
Figure 18:
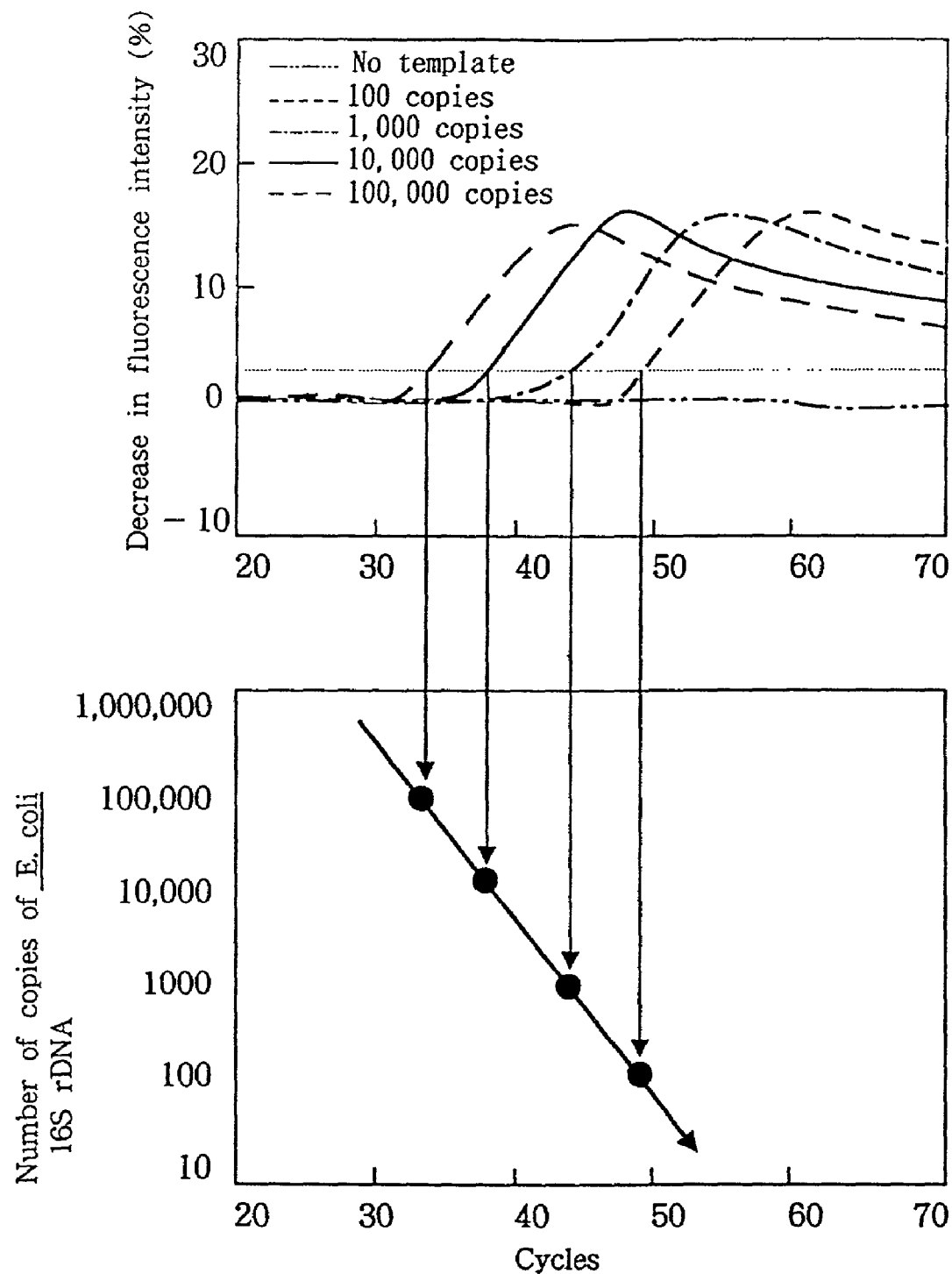
Figure 19:
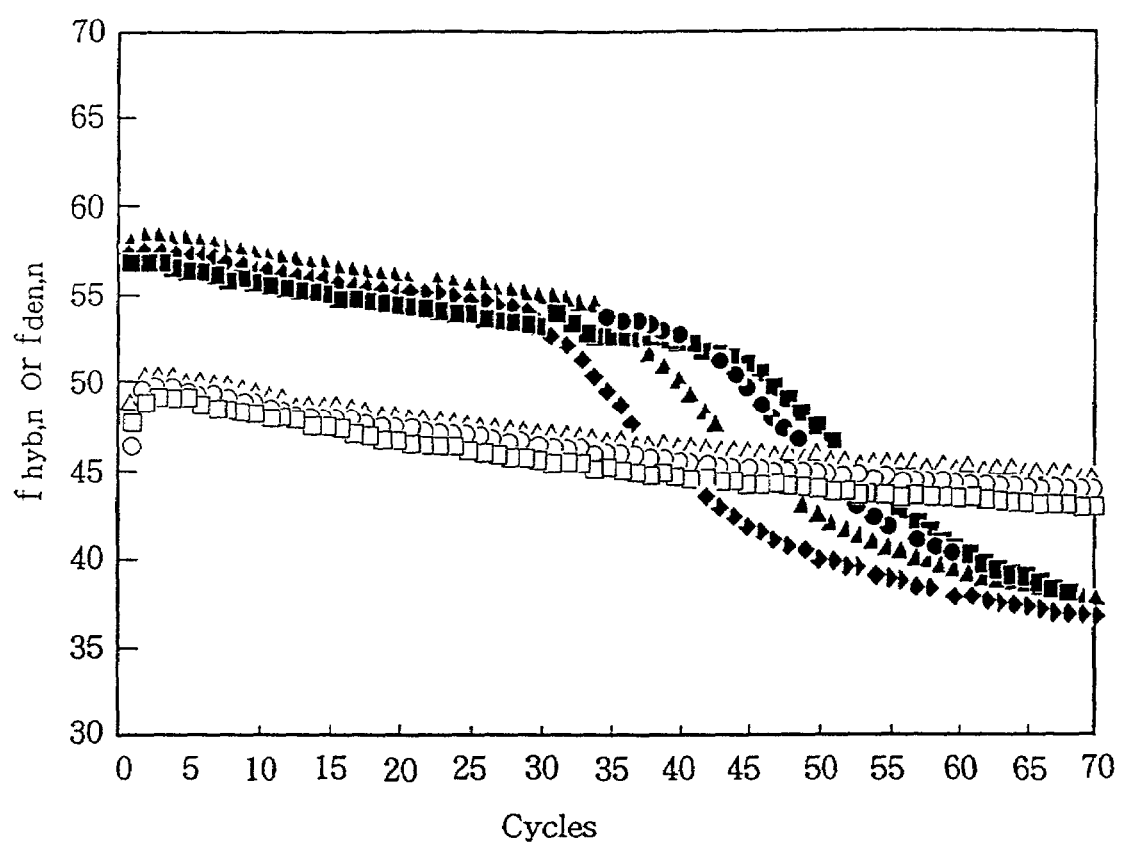

FIG. 16 diagrammatically shows a relationship between cycles and the logarithm of a decrease in fluorescence emission from a fluorescent dye in the quantitative PCR making use of primers 1 and 2 labeled with "BODIPY FL/C6", in which signs ① to ⑧ have the same meanings as defined above in connection with FIG. 15;

FIG. 17 is a diagram showing a working line for 16S rDNA of *Escherichia coli*, which was prepared using the quantitative PCR according to the present invention;

FIG. 18 (upper diagram) depicts decreases (%) in fluorescence intensity in real-time quantitative PCR according to the present invention in which a single probe of the present invention was used as opposed to two probes labeled with a fluorescent dye and required for a conventional real-time quantitative PCR method using FRET;

FIG. 18 (lower diagram) shows a working line prepared by calculating numbers of cycles (threshold numbers: Ct values) at which decreases in fluorescence intensity were begun to be significantly observed;

FIG. 19 depicts fluorescence decrease curves obtained by real-time quantitative PCR, which used an invention primer labeled with "BODIPY FL/C6", without performing correction processing according to the present invention, in which:
- ■ Target nucleic acid: 10 copies; Temperature of the reaction system upon measurement of fluorescence intensity: 72° C.
- ● Target nucleic acid: 100 copies; Temperature of the reaction system upon measurement of fluorescence intensity: 72° C.
- ▲ Target nucleic acid: 1,000 copies; Temperature of the reaction system upon measurement of fluorescence intensity: 72° C.
- ♦ Target nucleic acid: 10,000 copies; Temperature of the reaction system upon measurement of fluorescence intensity: 72° C.
- □ Target nucleic acid: 10 copies; Temperature of the reaction system upon measurement of fluorescence intensity: 95° C.
- ○ Target nucleic acid: 100 copies; Temperature of the reaction system upon measurement of fluorescence intensity: 95° C.
- Δ A Target nucleic acid: 1,000 copies; Temperature of the reaction system upon measurement of fluorescence intensity: 95° C.
- ◇ Target nucleic acid: 10,000 copies; Temperature of the reaction system upon measurement of fluorescence intensity: 95° C.

Figure 20:
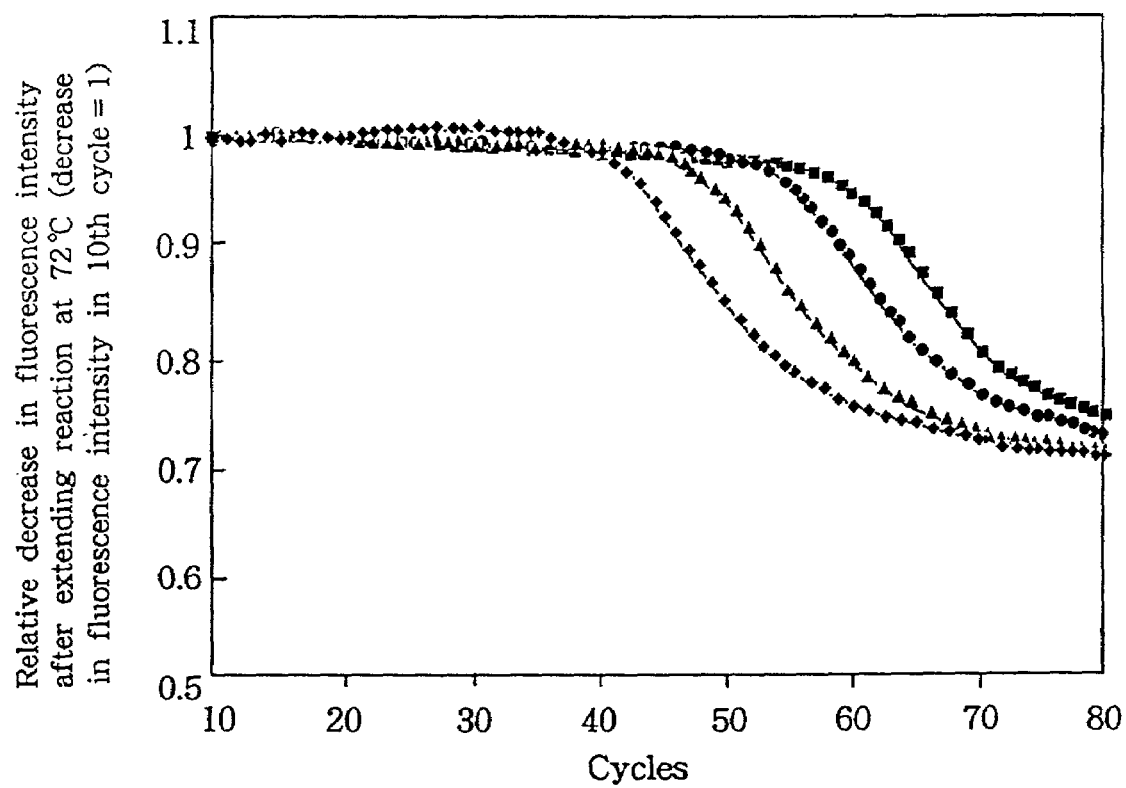

FIG. 20 shows fluorescence decrease curves obtained by the real-time quantitative PCR in FIG. 19 except that on each of the curves, each decrease (%) in fluorescence emission was corrected assuming that the corresponding value in the $10^{th}$ cycle was 1, in which:
- ■ Target nucleic acid: 10 copies; Temperature upon measurement of fluorescence intensity: 72° C.
- ● Target nucleic acid: 100 copies; Temperature upon measurement of fluorescence intensity: 72° C.
- ▲ Target nucleic acid: 1,000 copies; Temperature upon measurement of fluorescence intensity: 72° C.
- ♦ Target nucleic acid: 10,000 copies; Temperature upon measurement of fluorescence intensity: 72° C.

Figure 21:
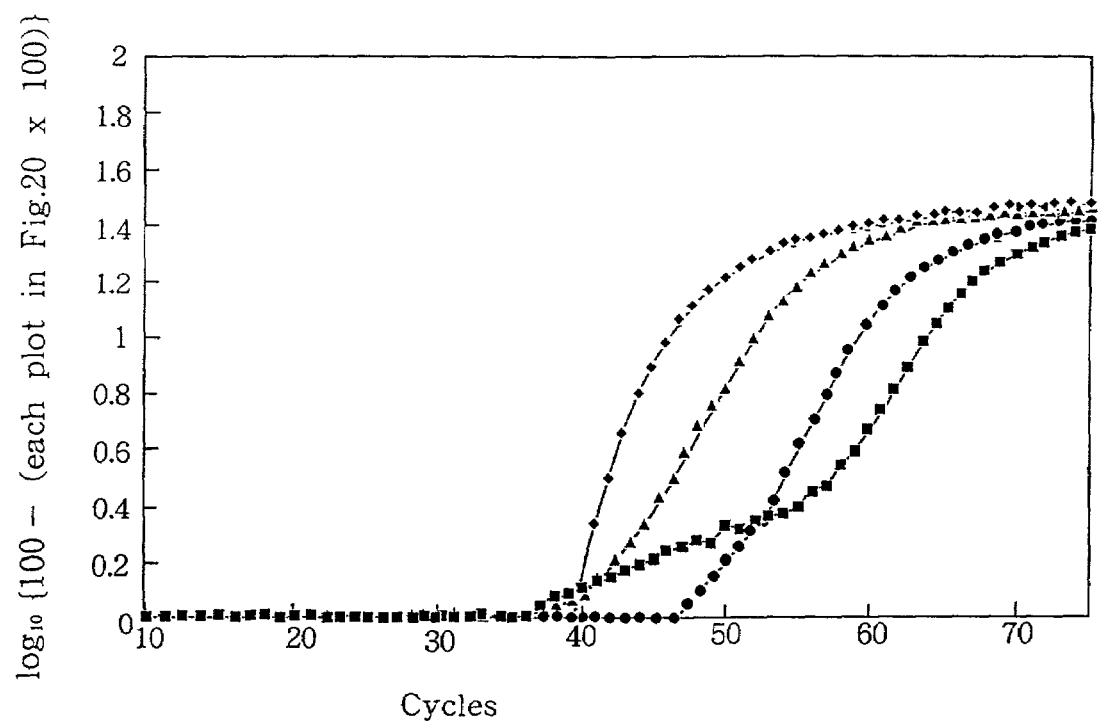

FIG. 21 shows curves obtained by calculating, with respect to the individual plotted values on the respective curves in FIG. 20, the rates of decreases (the rates of changes) in fluorescence intensity in accordance with the formula (9) and then plotting the thus-calculated values, in which:
- ■ Target nucleic acid: 10 copies.
- ● Target nucleic acid: 100 copies.
- ▲ Target nucleic acid: 1,000 copies.
- ♦ Target nucleic acid: 10,000 copies.

Figure 22:
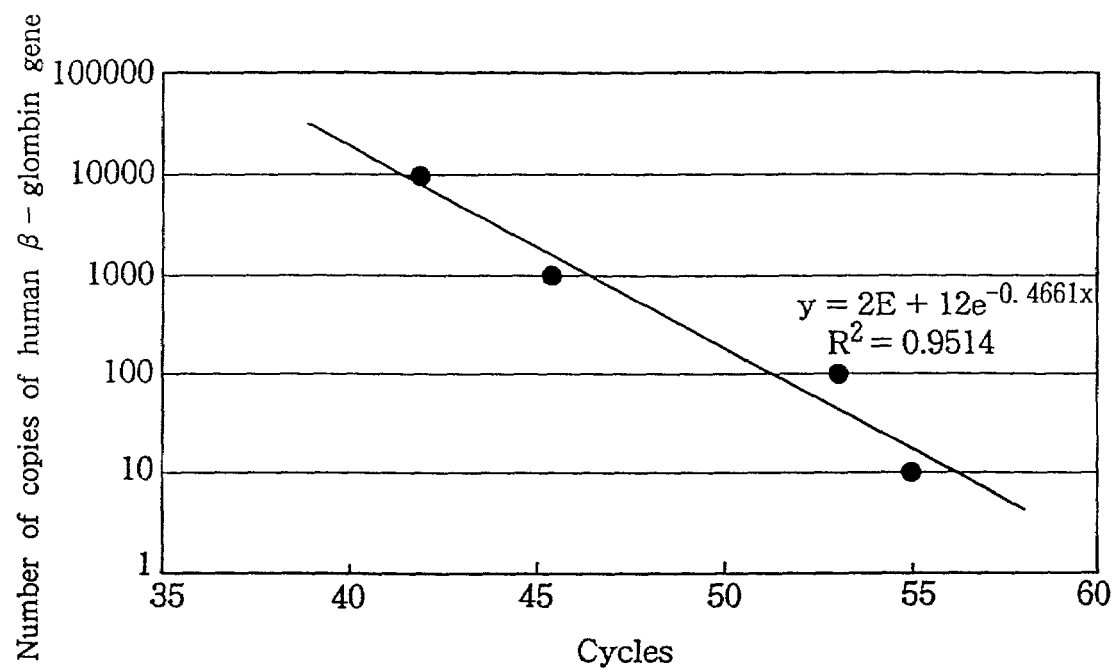

FIG. 22 shows a working line for human genome DNA as obtained from the data in FIG. 21, in which:
- y: Number of copies of human β-globin gene,
- x: cycles (Ct), and
- $R^2$: correlation coefficient.

Figure 23:
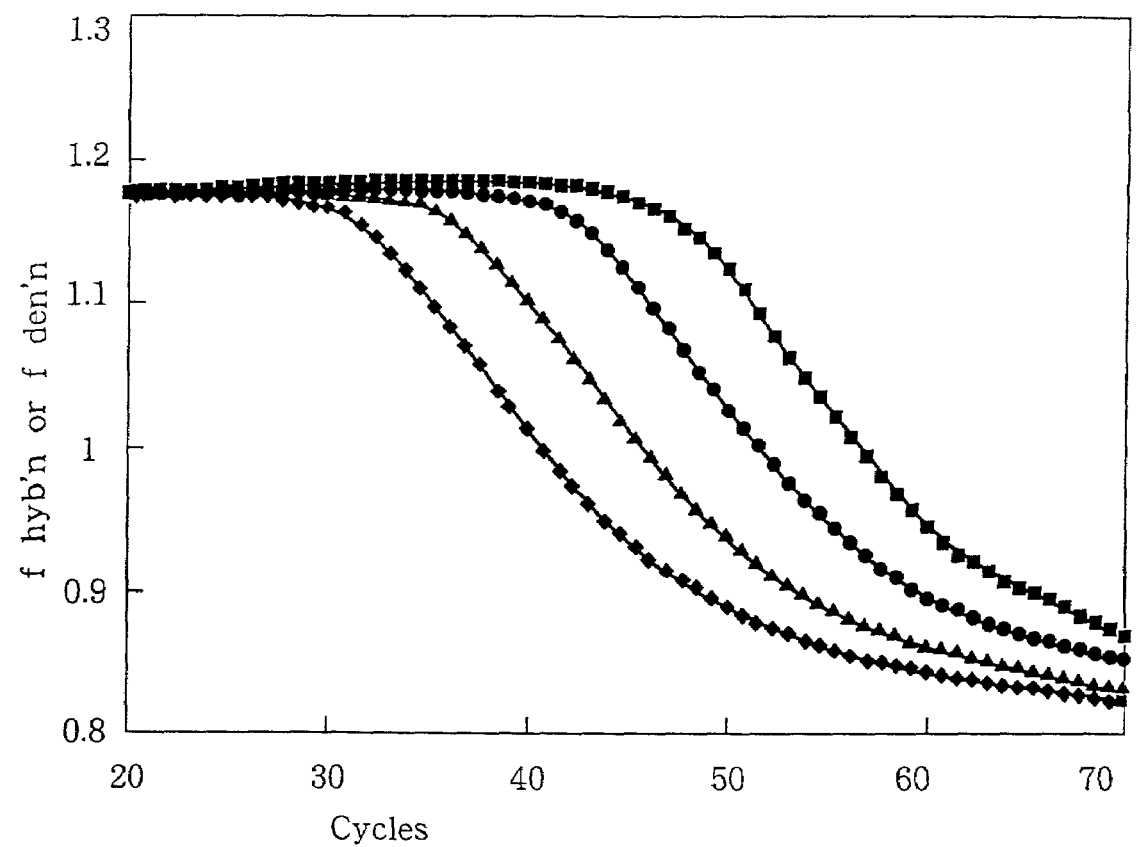

FIG. 23 depicts curves obtained by subjecting the measurement values in the individual cycles in FIG. 19 to correction processing in accordance with the formula (1) and then plotting the corrected values relative to their corresponding cycles, in which:
- ■ Target nucleic acid: 10 copies.
- ● Target nucleic acid: 100 copies.
- ▲ Target nucleic acid: 1,000 copies.
- ♦ Target nucleic acid: 10,000 copies.

Figure 24:
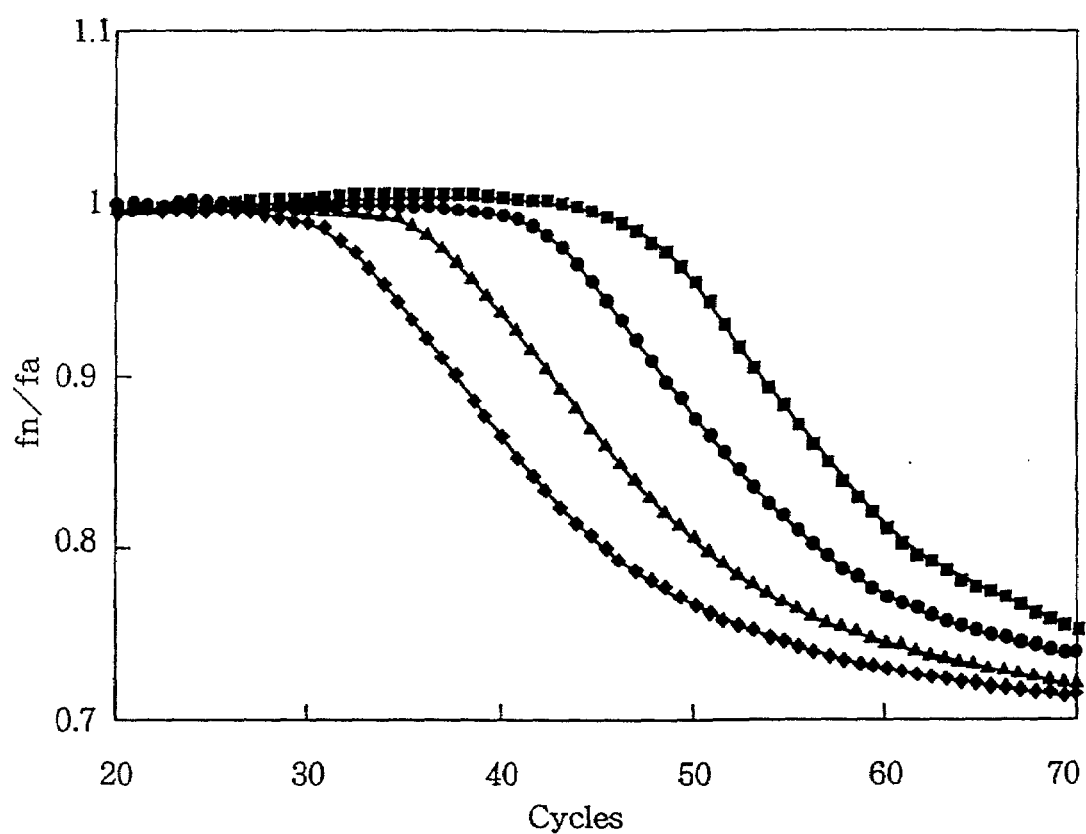

FIG. 24 illustrates curves obtained by plotting values, which had been obtained by processing the processed values of the individual cycles in FIG. 23 in accordance with the formula (3), against their corresponding cycles, in which
- ■ Target nucleic acid: 10 copies.
- ● Target nucleic acid: 100 copies.
- ▲ Target nucleic acid: 1,000 copies.
- ♦ Target nucleic acid: 10,000 copies.

Figure 25:
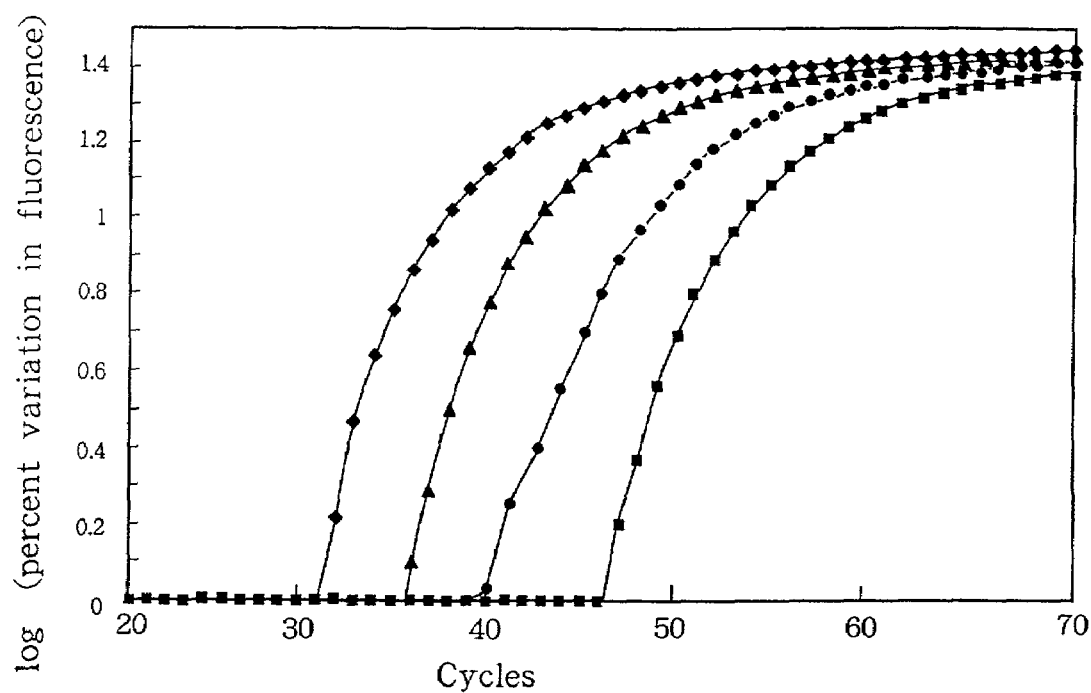

FIG. 25 shows curves obtained by subjecting the corrected values in the individual cycles in FIG. 24 to correction processing in accordance with the formula (6) and then plotting the corrected values relative to their corresponding cycles, in which:
- ■ Target nucleic acid: 10 copies.
- ● Target nucleic acid: 100 copies.
- ▲ Target nucleic acid: 1,000 copies.
- ♦ Target nucleic acid: 10,000 copies.

Figure 26:
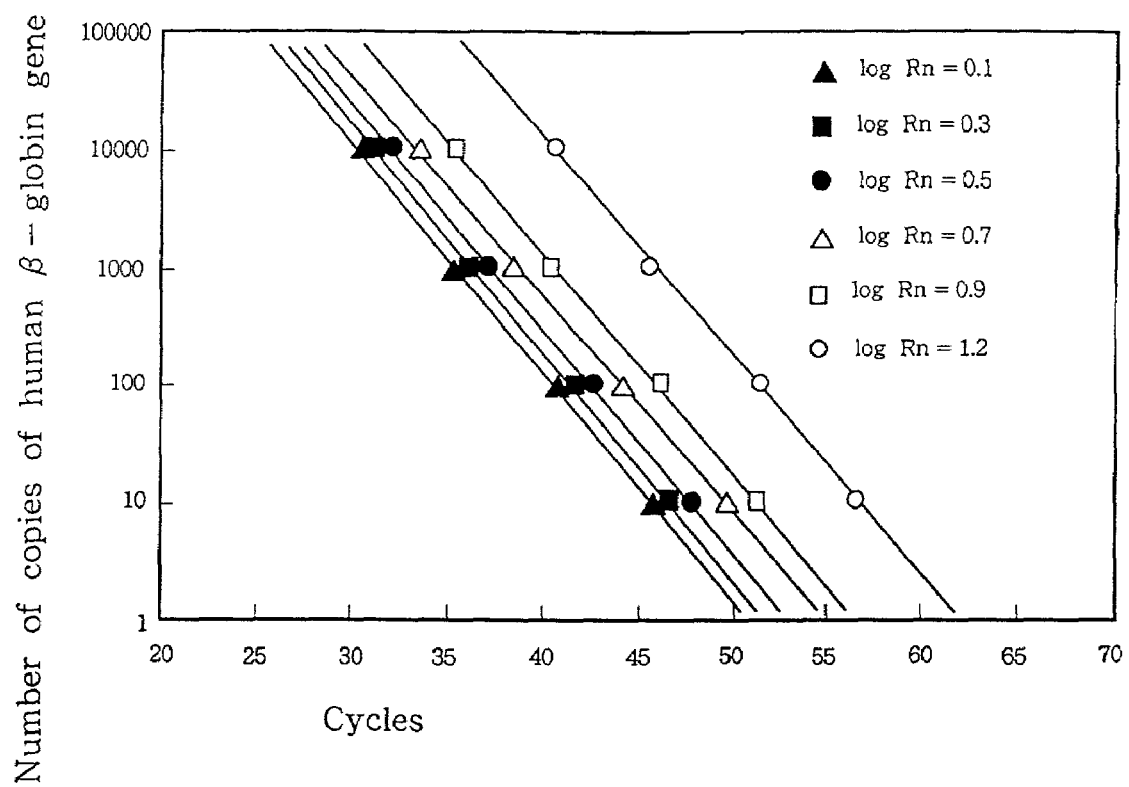

FIG. 26 shows working lines drawn corresponding to 0.1, 0.3, 0.5, 0.7, 0.9 and 1.2 chosen at will as candidates for Ct values from the respective values of log (changes in fluorescence, %) in FIG. 24, in which the individual working lines have the following correlation coefficients:
- ▲ $\log_{10}$ (change in fluorescence, %)=0.1; correlation coefficient: 0.998
- ■ $\log_{12}$ (change in fluorescence, %)=0.3; correlation coefficient: 0.999
- ● $\log_{10}$ (change in fluorescence, %)=0.5; correlation coefficient: 0.9993
- Δ$\log_{10}$ (change in fluorescence, %)=0.7 correlation coefficient: 0.9985
- □ $\log_{10}$ (change in fluorescence, %)=0.9 correlation coefficient: 0.9989
- ○ $\log_{10}$ (change in fluorescence, %)=1.2 correlation coefficient: 0.9988

Figure 27:
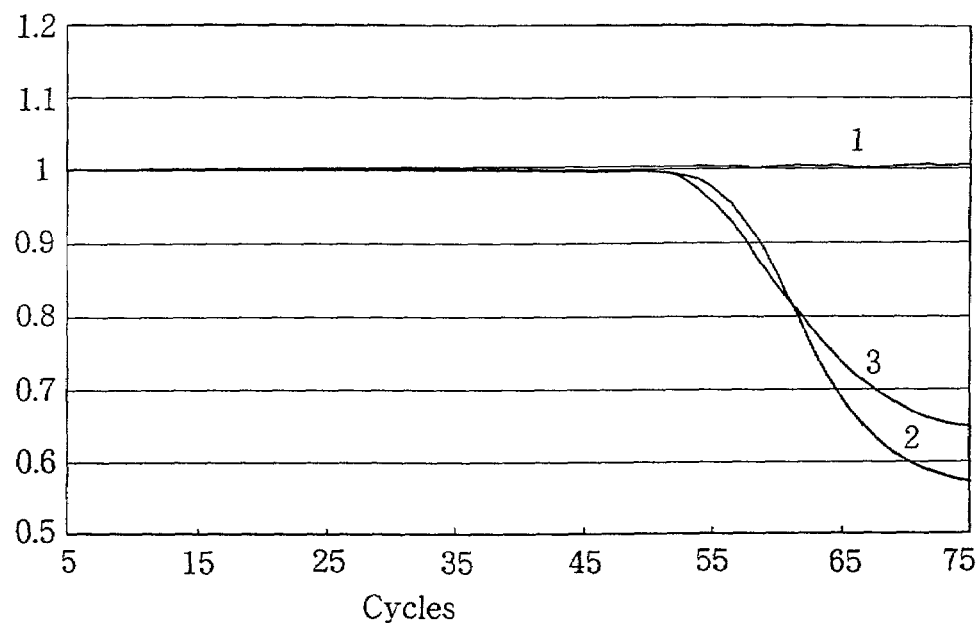
Figure 28:
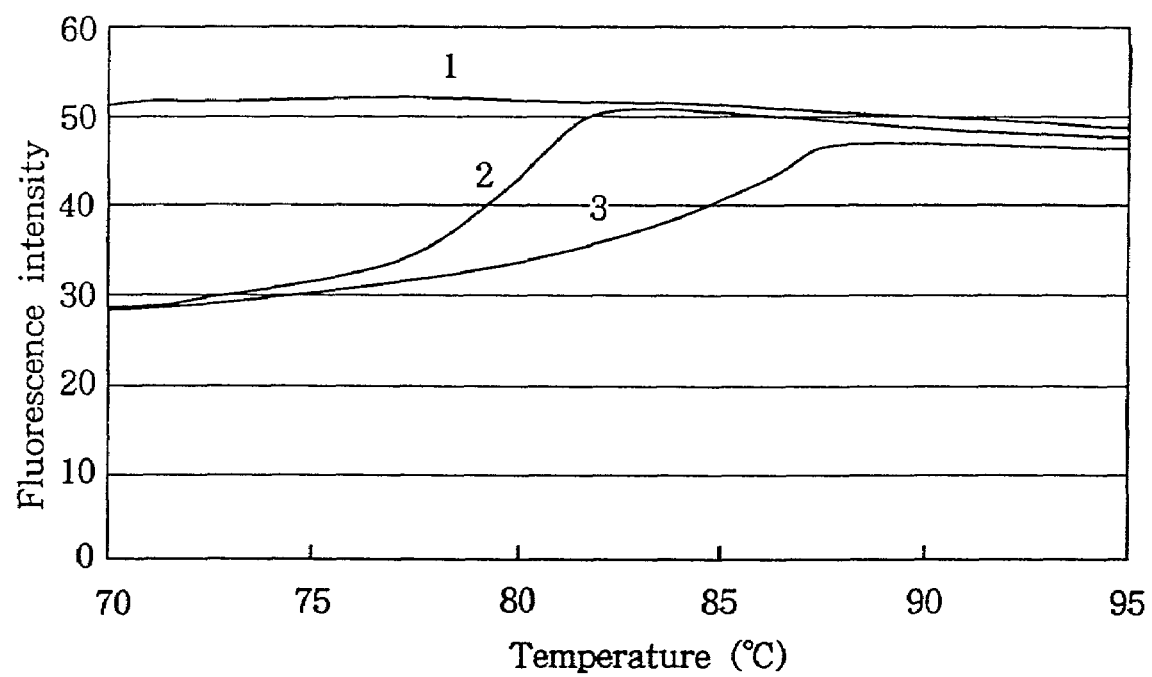
Figure 29:
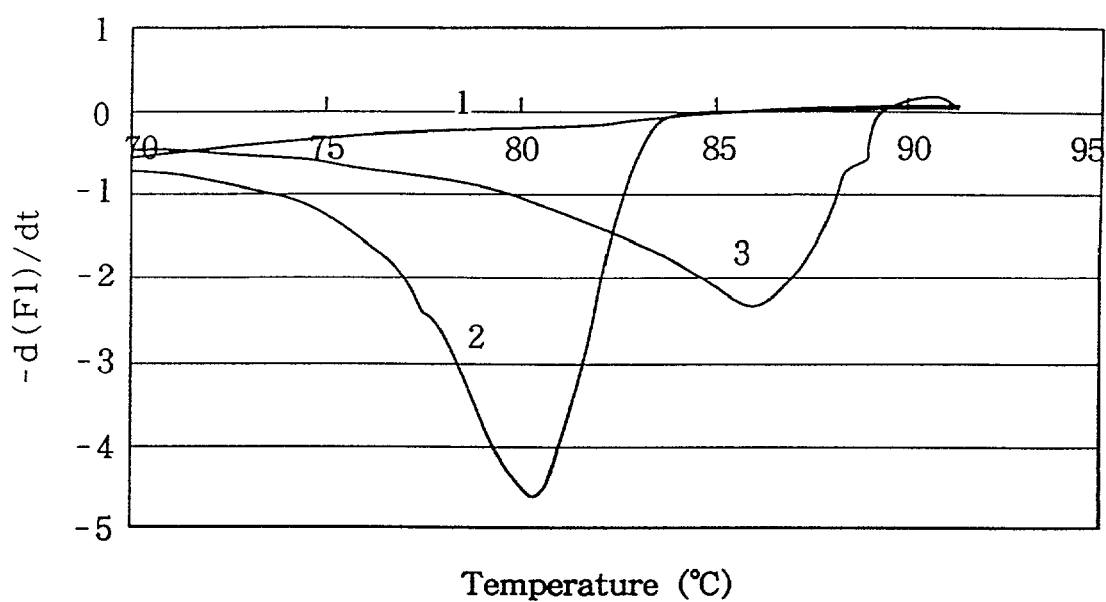
Figure 30:
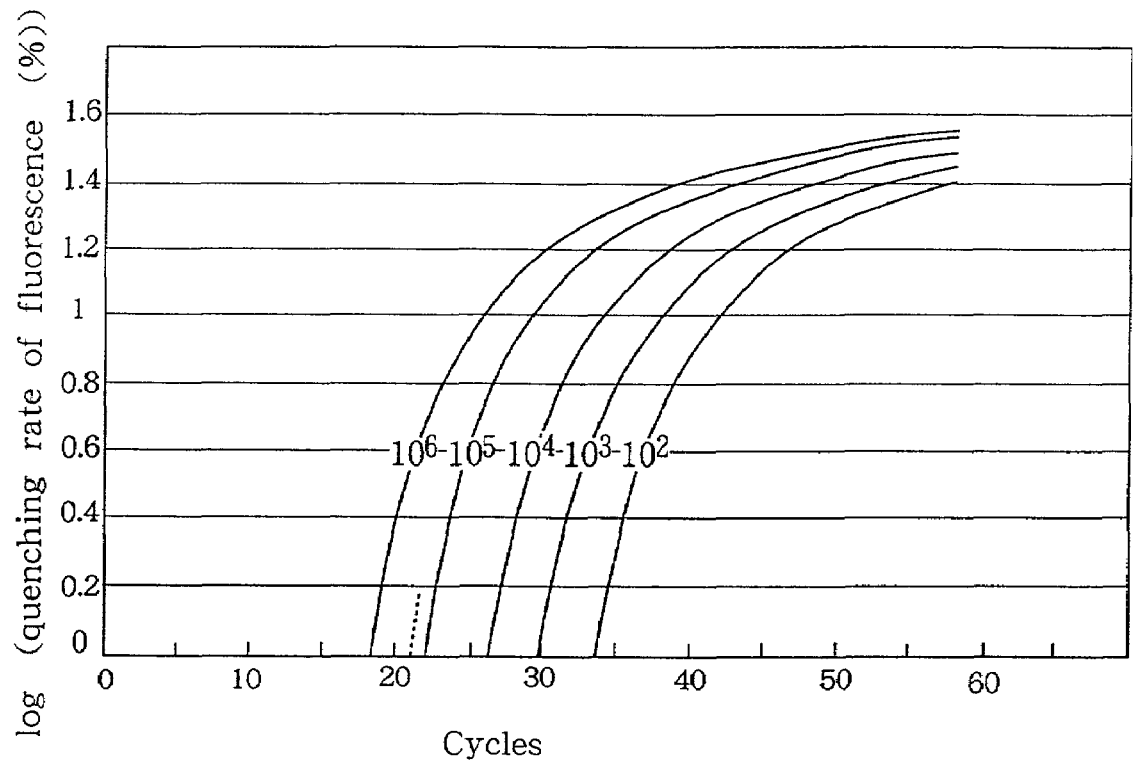
Figure 32:
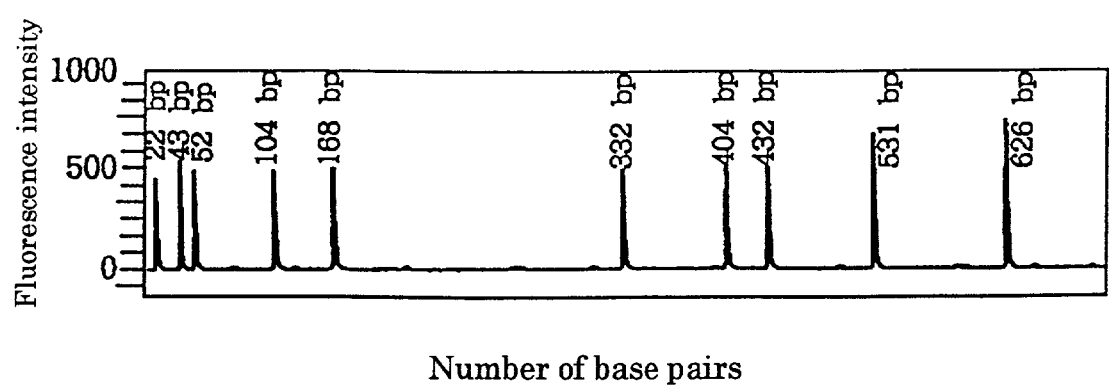
Figure 33:
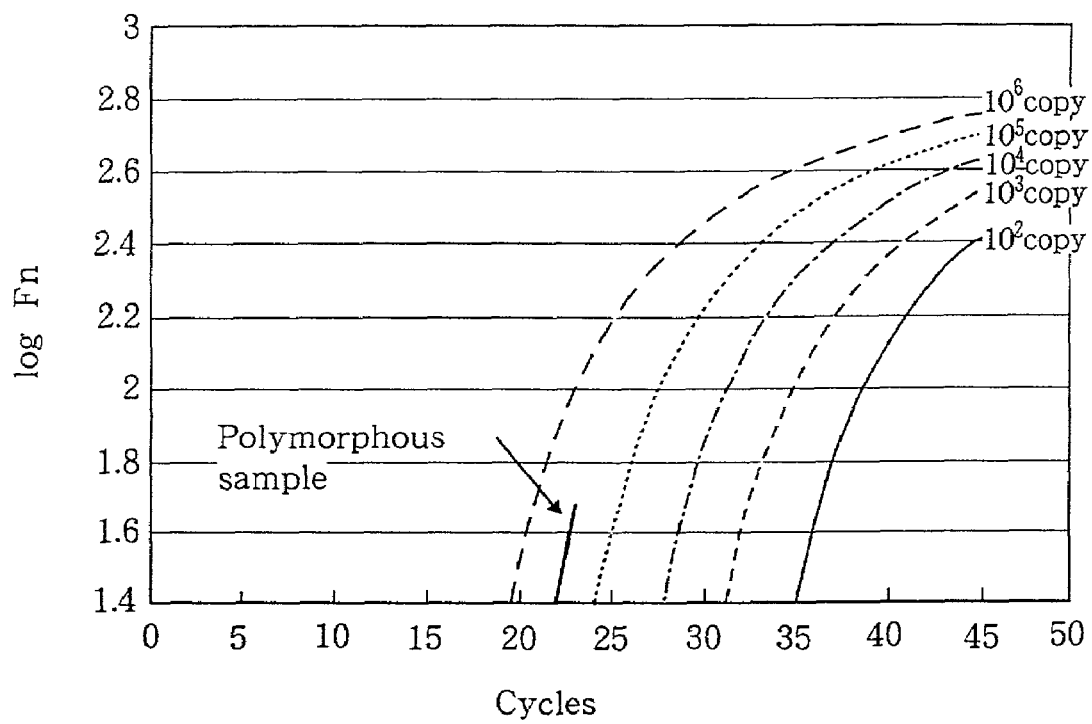
Figure 34:
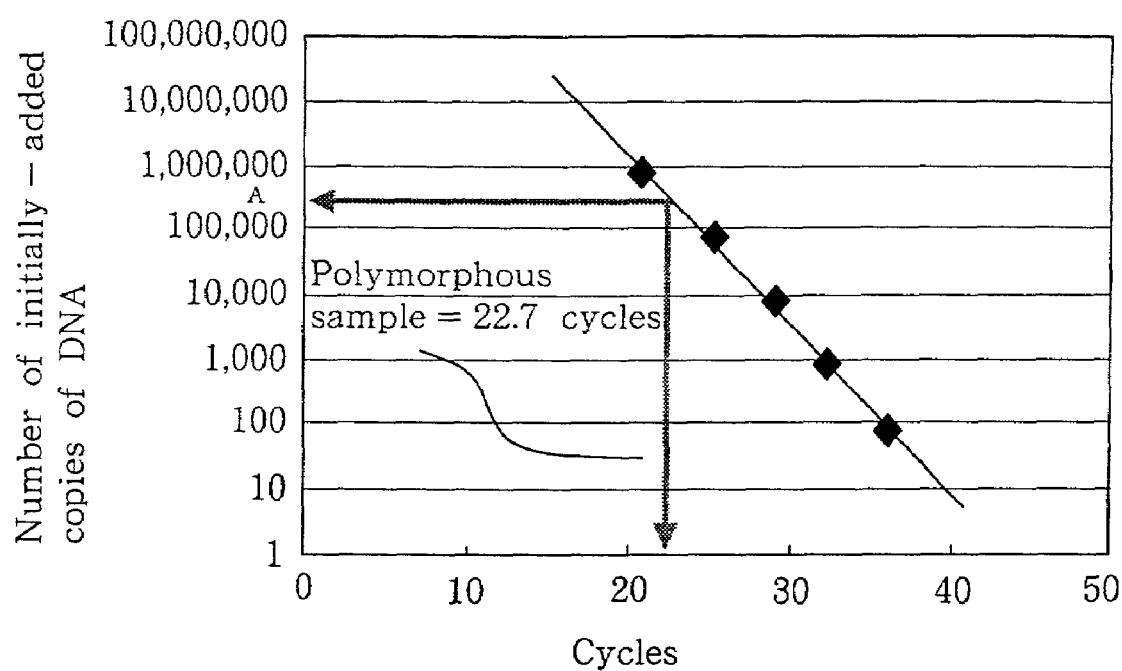
Figure 35:
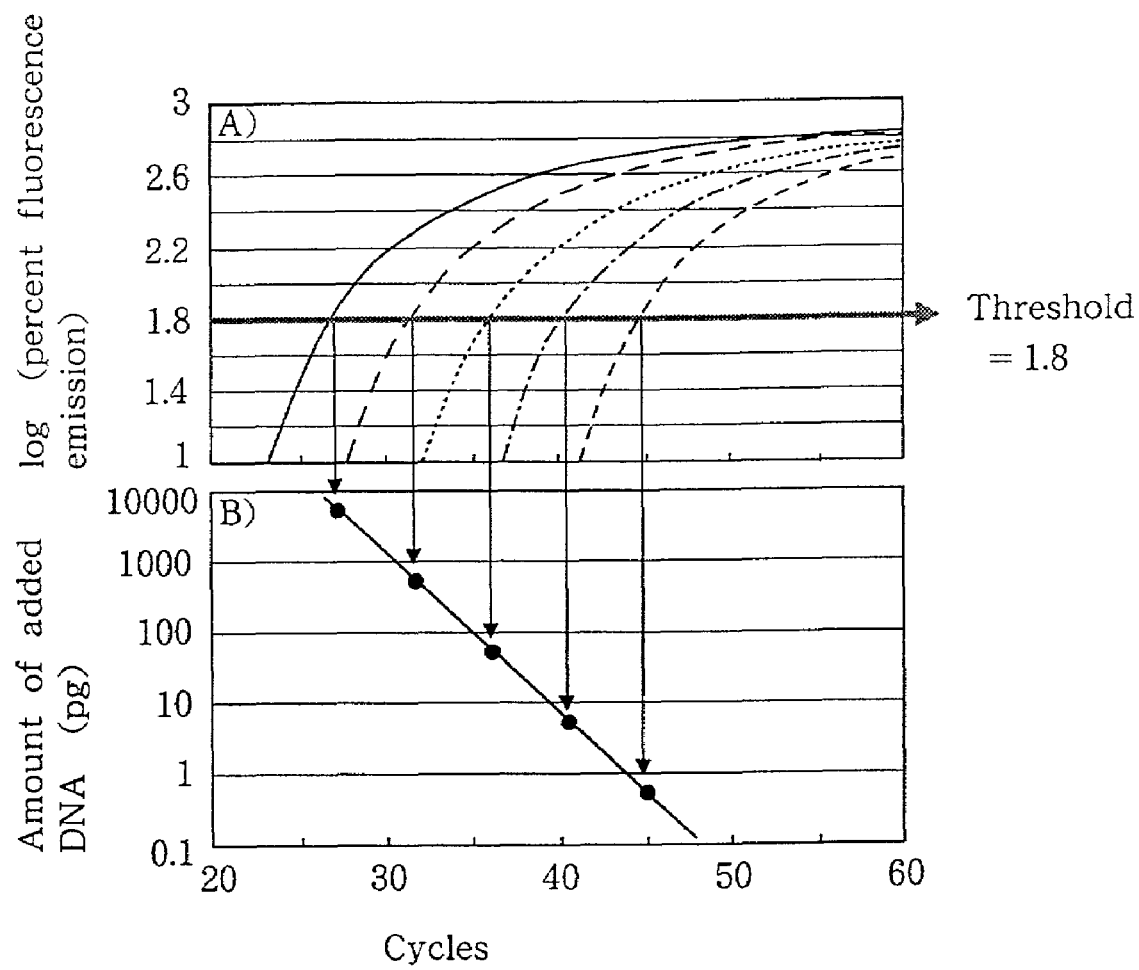
Figure 36:
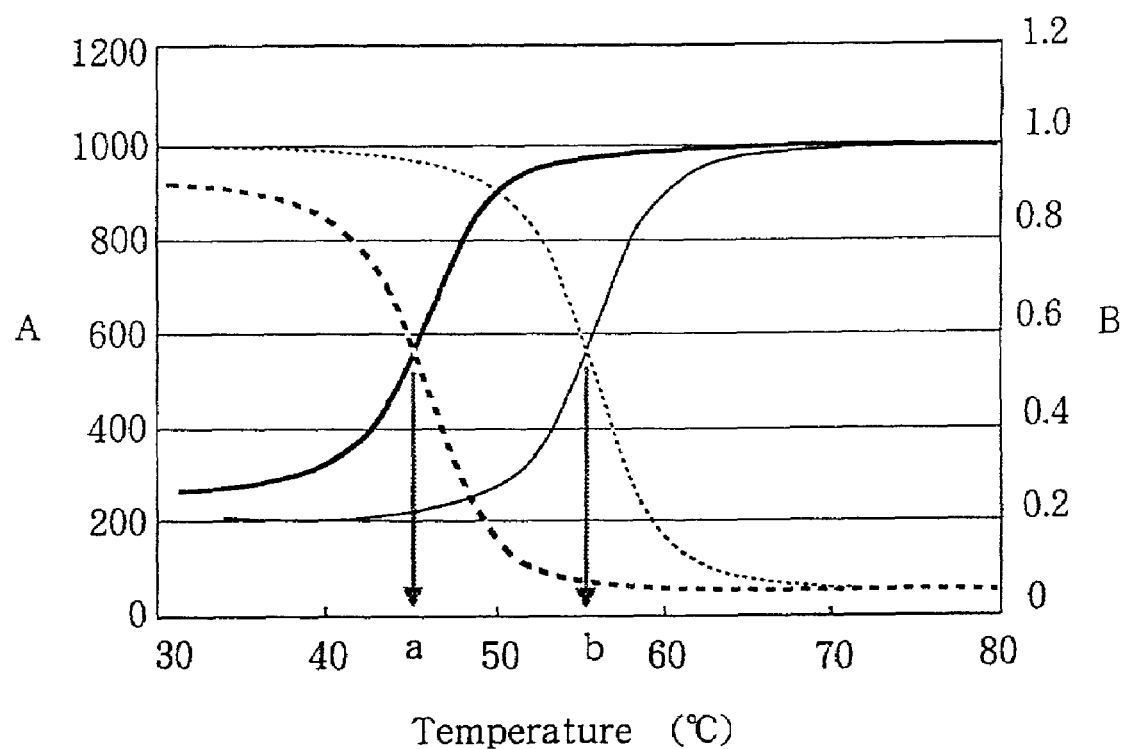
Figure 37:
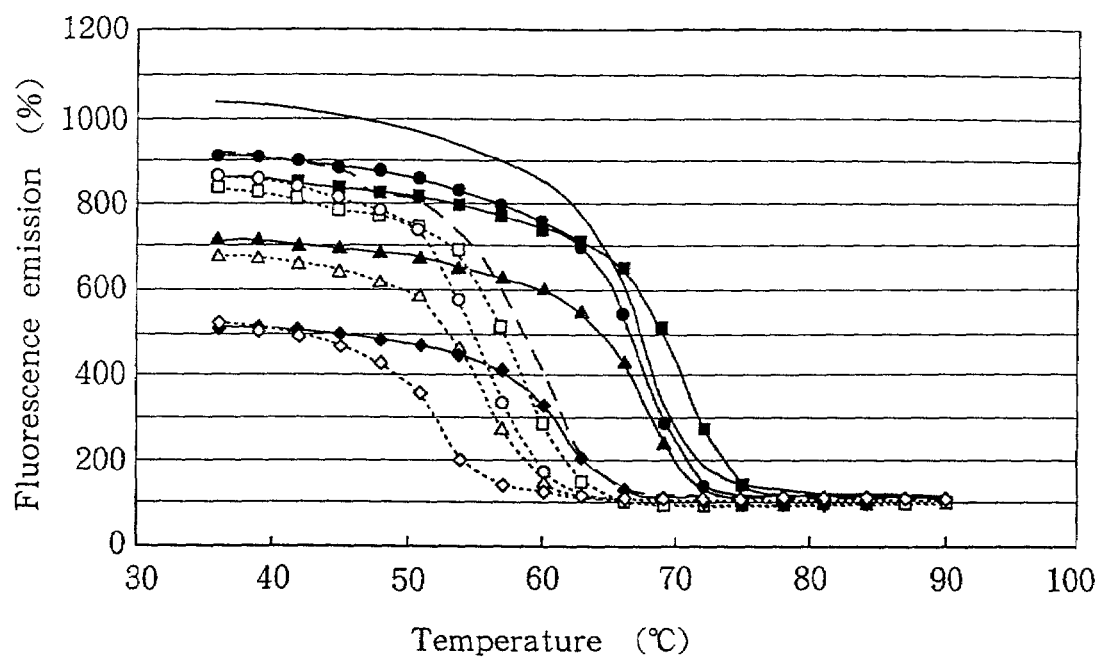
Figure 38:
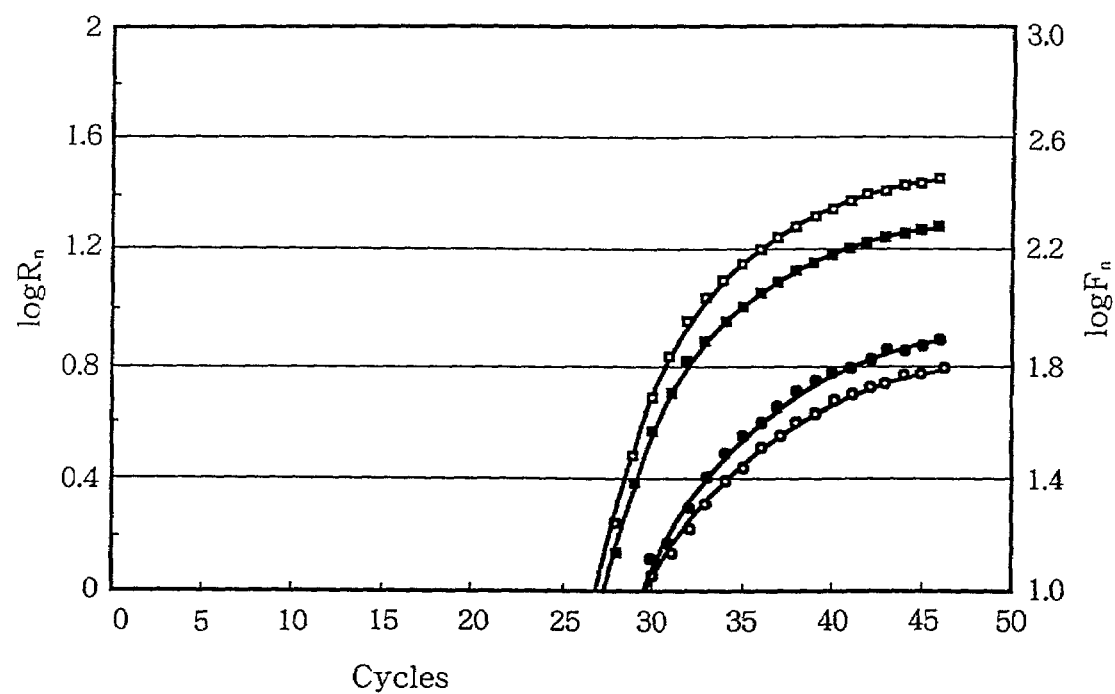
Figure 39:
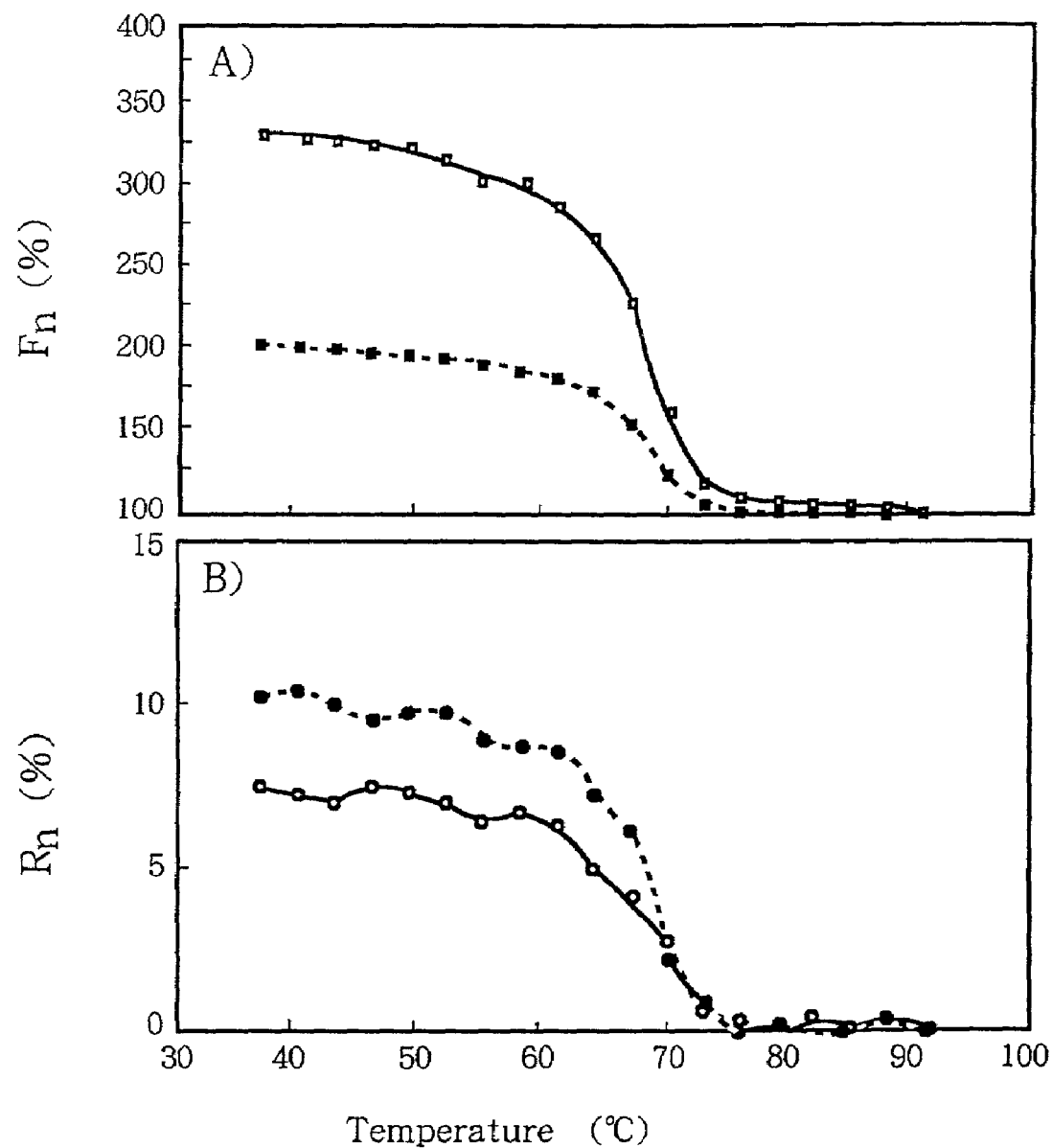

FIG. 27 depicts fluorescence decrease curves when real-time quantitative PCR was conducted on human genome DNA of 1 copy and 10 copies by using an invention primer labeled with "BODIPY FL/C6" and the correction processing of the formula (1) was applied, in which:
1: target nucleic acid=0 copy,
2: target nucleic acid=1 copy, and
3: target nucleic acid=10 copies;

FIG. 28 illustrates melting curves of nucleic acids when a melting curve analysis was conducted with respect to the PCR amplification products shown in FIG. 27, in which:
1: target nucleic acid=0 copy,
2: target nucleic acid=1 copy, and
3: target nucleic acid=10 copies;

FIG. 29 illustrates curves obtained by differentiating the curves of FIG. 28 and showing Tm values as valleys, in which:
2: target nucleic acid: 1 copy, and
3: target nucleic acid: 10 copies;

FIG. 30 shows amplification curves of 16S rRNA genes (cDNAs) obtained using quantitative PCT according to the present invention, in which:

Solid curves: cDNA of *Escherichia coli*
Dotted curve: Polymorphous cDNA
$10^2$, $10^3$, $10^4$, $10^5$, $10^6$: Numbers of copies;

FIG. 31 illustrates a working line for cDNA, which was prepared by a data analysis method according to the present invention, in which:
a: 288,000 copies;

FIG. 32 illustrates an analysis pattern by polymorphous T-RELP according to the present invention, in which
bp: Number of base pairs;

FIG. 33 diagrammatically illustrates results of quantitative PCR making use of a fluorescence emitting probe as a primer (fluorescence emitting primer) (exponential graph);

FIG. 34 shows a working line for 16S rRNA gene (fluorescence emitting primer: 0 µM), in which:
A: Number of copies in an artificial co-cultivation system of microorganisms (about 296,000 copies);

FIG. 35 (upper diagram) illustrates results of real-time monitoring on PCR amplification products obtained by real-time quantitative PCR making use of a fluorescence emitting primer;

FIG. 35 (lower diagram) shows a working line obtained by the real-time monitoring;

FIG. 36 diagrammatically shows results of an SNPs detection by a fluorescence emitting probe, in which:
.....: 100% matching target nucleic acid (denaturation curve from a fluorescence emitting probe),
-----: Target nucleic acid containing single nucleotide polymorphism (denaturation curve from a fluorescence emitting probe),
_____: 100% matching target nucleic acid (denaturation curve from a fluorescence quenching probe),
_____: Target nucleic acid containing single nucleotide polymorphism (denaturation curve from a fluorescence quenching probe),
A: Percent fluorescence emission—data of fluorescence emitting probe,
B: Relative value of fluorescence—data of fluorescence quenching probe,
a: About 46° C., and
b: About 46° C.;

FIG. 37 diagrammatically illustrates results of an SNPs detection by a DNA chips with fluorescence emitting probes fixed thereon, in which:
———≡———: No. 1 100% matching
....□....: No. 1 1 base mismatched
———▲———: No. 2 100% matching
....∆....: No. 2 1 base mismatched
———●———: No. 3 100% matching
....○....: No. 3 1 base mismatched
———♦———: No. 4 100% matching
....◊....: No. 4 1 base mismatched
_____: No. 5 100% matching
--------: No. 5 1 base mismatched;

FIG. 38 diagrammatically shows results of real-time monitoring of PCR reaction using a DNA array having fixed fluorescence emitting probes and fluorescence quenching probes, in which:
Closed square: WIAF-10600 (No. 1)
Open square: WIAF-10578 (No. 2)
Closed circle: WIAF-10600 (No. 3)
Open circle: WIAF-10578 (No. 4)
Fn: Relative fluorescence rate at n cycle
Rn: Fluorescent quenching rate at n cycle; and FIG. 39 depicts melting curves of PCR products using a DNA array having fixed fluorescence emitting probes and fluorescence quenching probes, in which:
Closed square: WIAF-10600 (No. 1)
Open square: WIAF-10578 (No. 2)
Closed circle: WIAF-10600 (No. 3)
Open circle: WIAF-10578 (No. 4)
Fn, Rn: Same meanings as defined above in connection with FIG. 38.

DETAILED DESCRIPTION OF THE INVENTION AND PREFERRED EMBODIMENTS

The present invention will next be described in further detail based on certain preferred embodiments.

The present invention has three aspects.

The present invention, in the first aspect thereof, relates to a novel nucleic acid probe for determining a concentration of a target nucleic acid, comprising:
a single-stranded oligonucleotide capable of hybridizing to the target nucleic acid, and
a fluorescent dye and a quencher substance, both of which are labeled on the oligonucleotide,
wherein the oligonucleotide is labeled with the fluorescent dye and the quencher substance such that an intensity of fluorescence in a hybridization reaction system increases when the nucleic acid probe is hybridized with the target nucleic acid; and the oligonucleotide forms no stem-loop structure between bases at positions where the oligonucleotide is labeled with the fluorescent dye and the quencher substance, respectively. For the sake of brevity, the nucleic acid probe according to the present invention may therefore be called a "fluorescence emitting probe" or a "nucleic acid probe according to the first aspect of the present invention" in the subsequent description.

The present invention, in the second aspect thereof, relates to a nucleic acid probe labeled with a fluorescent dye, which is characterized in that, when the nucleic acid probe hybridizes to a target nucleic acid, emission of fluorescence from the fluorescent dye decreases after the hybridization. It is to be noted that the nucleic acid probe according to the present invention may also be called a "fluorescence quenching probe" or a "nucleic acid probe according to the second aspect of the present invention" for the sake of brevity.

The present invention, in the third aspect thereof, relates to a variety of use of the fluorescence emitting probe and fluorescence quenching probe.

A description will now be made about technical terms employed in the present invention.

The term "probe-nucleic acid hybrid complex" as used herein means one (complex) in which a nucleic acid probe according to the present invention, which is labeled with a fluorescent dye, and a target nucleic acid are hybridized with each other. For the same of brevity, it will be called a "nucleic acid hybrid complex" in a shortened form.

Further, the term "fluorescent dye-nucleic acid conjugate" as used herein means a conjugate in which a fluorescent dye is bound with a target nucleic acid. Illustrative is a conjugate in which an intercalator is bound in a double-stranded nucleic acid.

The terms as used herein—such as to hybridize, hybridization, stem-loop structures, quenching, quenching effects, DNAs, RNAs, cDNAs, mRNAs, rRNAs, XTPs, dXTPs, NTPs, dNTPs, nucleic acid probes, helper nucleic acid probes (or nucleic acid helper probes, or simply helper probes), to hybridize, hybridization, intercalators, primers, annealing, extending reactions, thermal denaturing reactions, nucleic acid melting curves, PCR, RT-PCR, RNA-primed PCR, stretch PCR, reverse PCR, PCR using Alu sequence(s), multiple PCR, PCR using mixed primers, PCR using PNA, hybridization assays, FISH methods (fluorescent in situ hybridization assays), PCR methods (polymerase chain assays), LCR methods (ligase chain reactions), SD methods (strand displacement assays), competitive hybridization, DNA chips, nucleic acid detecting (gene-detecting) devices, SNP (single nucleotide polymorphism), and co-cultivation systems of plural microorganisms—have the same meanings as the corresponding terms generally employed these days in molecular biology, genetic engineering, bioengineering and the like.

The term "target gene" or "target nucleic acid" as used herein means a gene or a nucleic acid the quantitation or qualitative detection or mere detection of which is intended, irrespective whether it is in a purified form or not and further irrespective of its concentration. Various other nucleic acids may also exist together with the target nucleic acid. For example, the target nucleic acid may be a specific nucleic acid in a co-cultivation system microorganisms (a mixed system of RNAs or gene DNAs of plural microorganisms) or a symbiotic cultivation system of microorganisms (a mixed system of RNAs or gene DNAs of plural animals, plants and/or microorganisms), the quantitation or qualitative detection or mere detection of which is intended. Purification of the specific nucleic acid, if needed, can be conducted by a method known per se in the art. For example, purification can be effected using a purification kit or the like available on the market. Specific examples of the above-described nucleic acid can include DNAs, RNAS, PNAs, oligodeoxyribonucleotides, and oligoriboxynucleotides. Other examples can include chimera nucleic acids of the above-exemplified nucleic acids.

The expression "to determine a concentration of a target nucleic acid" as used herein means to quantitatively determine concentration(s), to perform qualitative detection, to simply detect, or to perform an analysis for polymorphism and/or mutation, all with respect to one or more nucleic acids in a measurement system. In the case of plural nucleic acids, quantitative detection of the plural nucleic acids at the same time, simple detection of the plural nucleic acids at the same time and an analysis for the polymorphism, mutation and/or the like of the plural nucleic acids at the same time obviously fall within the technical scope of the present invention.

The term "device for the measurement of a concentration of a target nucleic acid" as used herein mean various DNA chips. Specific examples of the device can obviously include a variety of DNA chips. The present invention include all DNA chips irrespective of their types insofar as the nucleic acid probe according to the present invention can be applied to them.

The expression "method for determining a concentration of a target nucleic acid by using a nucleic acid probe labeled with a fluorescent dye (hereinafter simply called a "nucleic acid probe according to the present invention" or a "probe according to the present invention" means to determine the concentration of the target nucleic acid by a hybridization assay, FISH method (fluorescent in situ hybridization assay), PCR method (polymerase chain assay), LCR method (ligase chain reaction), SD method (strand displacement assay), competitive hybridization or the like.

A description will first be made of the fluorescence emitting probes.

This probe is characterized in that, when the probe is not hybridized with a target nucleic acid, emission of fluorescence from the fluorescent dye is inhibited by the quencher substance but, when the probe is hybridized with the target nucleic acid, the inhibition is rendered ineffective to result in an increase in the intensity of fluorescence.

The term "fluorescent dye" as used herein means fluorescent dyes of the like, which are generally used for the determination or detection of nucleic acids by labeling nucleic acid probes. Illustrative of such fluorescent dyes are fluorescein and derivatives thereof [for example, fluorescein isothiocyanate (FITC) and its derivatives]; Alexa 488, Alexa 532, cy3, cy5, 6-joe, EDANS; rhodamine 6G (R6G) and its derivatives [for example, tetramethylrhodamine (TMR), tetramethylrhodamine isothiocyanate (TMRITC), x-rhodamine, Texas red, "BODIPY FL" (trade name, product of Molecular Probes, Inc. (Eugene, Oreg., U.S.A.), "BODIPY FL/C3" (trade name, product of Molecular Probes, Inc.), "BODIPY FL/C6" (trade name, product of Molecular Probes, Inc.), "BODIPY 5-FAM" (trade name, product of Molecular Probes, Inc.), "BODIPY TMR" (trade name, product of Molecular Probes, Inc.), and derivatives thereof (for example, "BODIPY TR" (trade name, product of Molecular Probes, Inc.), "BODIPY R6G" (trade name, product of Molecular Probes, Inc.), "BODIPY 564" (trade name, product of Molecular Probes, Inc.), and "BODIPY 581" (trade name, product of Molecular Probes, Inc.)]. Among these, FITC, EDANS, Texas red, 6-joe, TMR, Alexa 488, Alexa 532, " BODIPY FL/C3" and "BODIPY FL/C6" are preferred, with EDANS, Texas red, FITC, TMR, 6-joe, "BODIPY FL/C3" and "BODIPY FL/C6" being more preferred.

The term "quencher substance" means a substance which acts on the above-described fluorescent dye and inhibits or quenches emission of fluorescence from the fluorescent dye. Illustrative are Dabcyl, "QSY7" (Molecular Probes), "QSY33" (Molecular Probes), Ferrocene and its derivatives, methyl viologen, and N,N'-dimethyl-2,9-diazopyrenium, with Dabcyl and the like being preferred.

By labeling an oligonucleotide at specific positions thereof with such fluorescent dye and quencher substance as described above, the emission of fluorescence from the fluorescent dye is subjected to quenching effect by the quencher substance.

The expression "single-stranded oligonucleotide, which forms a nucleic acid probe according to the present invention and forms no stem-loop structure between bases at positions where the oligonucleotide is labeled with the fluorescent dye and the quencher substance, respectively" means an oligonucleotide which—owing to the complementation of base sequences at at least two positions between the bases at positions where the oligonucleotide is labeled with the fluorescent dye and the quencher substance, respectively—forms double strands in its own chain and forms no stem-loop structure.

To label an oligonucleotide useful in the practice of the present invention with a fluorescent dye and a quencher substance such that the intensity of fluorescence in a hybridization reaction system increases when the resulting nucleic acid probe according to the present invention is hybridized with a target nucleic acid, the labeling can be conducted as will be described hereinafter.

The distance between the bases at the positions where the single-stranded oligonucleotide is labeled with the fluorescent dye and the quencher substance, respectively, is zero (0) in terms of the number of bases, that is, the single-stranded oligonucleotide is labeled at the same position of the same nucleotide thereof with the fluorescent dye and the quencher substance. As an alternative, the distance is 1 to 20 or {(a desired integer of from 3 to 8)+10n} (n: an integer$\geq$0) in terms of the number of bases. More preferably, the single-stranded oligonucleotide can be labeled at the same position of the same nucleotide thereof or can be labeled with a distance of from 4 to 8. It is desired to label an oligonucleotide with a fluorescent dye and a quencher substance, respectively, as described above. However, the distance between the bases depends strongly upon the base sequence of the probe, the fluorescent dye and quencher substance to be used for modification, the lengths of linkers adapted to bind them to the oligonucleotide, and the like. It is, therefore, difficult to fully specify the base-to-base distance. It is to be noted that the above-described base-to-base distances are merely general examples and the distance between the bases includes many exceptions.

Concerning the labeling positions, it is preferred that, when a single-stranded oligonucleotide is labeled at the position of the same nucleotide thereof, one of a fluorescent dye and a quencher substance is labeled to a base and the other is labeled to a portion other than bases, specifically to a phosphate portion or to a ribose portion or deoxyribose portion. In this case, labeling to the 3' end portion or 5' end portion is preferred.

When it is desired to set the distance between the bases labeled with the fluorescent dye and quencher substance, respectively, at 1 to 20 or {(a desired integer of from 3 to 8)+10n} (n: an integer$\geq 0$), preferably at 4 to 8 or a number obtained by adding 10 to a desired number in this range, more preferably at 4 to 8 in terms of the number of bases, the oligonucleotide may be labeled in its chain with both of the fluorescent dye and quencher substance or may be labeled at the 5' end or 3' end thereof with one of the fluorescent dye and quencher substance and in the chain thereof with the other one. It is preferred to label the oligonucleotide at the 5' end or 3' end thereof with the fluorescent dye or the quencher substance and at a base, which is apart by the above-described number of bases from the end, with the quencher substance or the fluorescent dye. When it is desired to label the 3' end or 5' end in this case, the labeling can be effected to a base, a phosphate portion, a ribose portion or a deoxyribose portion, preferably to the phosphate portion, the ribose portion or the deoxyribose portion, more preferably to the phosphate portion. When it is desired to conduct the labeling into the chain, the labeling can be effected preferably to bases in the chain.

When the bases are modified in each of the above-described cases, the modification can be effected to any bases insofar as the modification is feasible. It is, however, preferred to effect the modification to the OH group, amino group, 2-N, 7-N and/or 8-C of a purine base or to the OH group, amino group, methyl group and/or 2-N of a pyrimidine base [ANALYTICAL BIOCHEMISTRY, 225, 32-38 (1998)].

The nucleic acid probe according to the present invention, which is to be hybridized to the target nucleic acid, may be formed of either an oligodeoxyribonucleotide or an oligoribonucleotide. The nucleic acid probe may be a chimeric oligonucleotide which contains both of them. These oligonucleotides may be in chemically-modified forms. Such chemically-modified oligonucleotides may be inserted in chimeric oligodeoxynucleotides.

Examples of the modified positions of the chemically-modified oligonucleotide can include an end hydroxyl group or end phosphate group of an end portion of an oligonucleotide, the position of a phosphate portion of an internucleoside, the 5-carbon of a pyrimidine ring, and the position of a saccharide (ribose or deoxyribose) in a nucleoside. Preferred examples are the positions of ribose or deoxyribose. Specific examples can include 2'-O-alkyloligoribonucleotides ("2'-O—" will hereinafter be abbreviated as "2-O—"), 2-O-alkyloligoribonucleotides, and 2-O-benzyloligoribonucleotides. The oligonucleotide is modified at the OH group(s) on the 2' carbon (s) of one or more ribose molecules at desired positions thereof with alkyl group(s), alkylene group(s) or benzyl group(s) (via ether bond(s)). Preferred examples useful in the present invention can include, among 2-O-alkyloligoribonucleotides, 2-O-methyloligoribonucleotide, 2-O-ethyloligoribonucleotide and 2-O-butyloligoribonucleotide; among 2-O-alkyloligoribonucleotides, 2-O-ethyleneoligoribonucleotide; and 2-O-benzyloligoribonucleotide. Particularly preferably, 2-O-methyloligoribonucleotide (hereinafter simply abbreviated s "2-O-Me-oligoribonucleotide") can be used. Application of such chemical modification to an oligonucleotide enhances its affinity with a target nucleic acid so that the efficiency of hybridization with a nucleic acid probe according to the present invention is improved. The improved efficiency of hybridization leads to a further improvement in the rate of a decrease in the intensity of fluorescence from the fluorescent dye of the nucleic acid probe according to the present invention. As a consequence, the accuracy of determination of the concentration of the target nucleic acid is improved further.

Incidentally, it is to be noted that the term "oligonucleotide" as used herein means an oligodeoxyribonucleotide or an oligoribonucleotide or both of them and hence, is a generic term for them.

2-O-alkyloligoribonucleotides, 2-O-alkyloligoribonucleotides and 2-O-benzyloligoribonucleotide can be synthesized by a known process [Nucleic Acids Research, 26, 2224-2229 (1998)]. As custom DNA synthesis services are available from GENSET SA, Paris, France, they can be readily obtained. The present inventors have completed the present invention by conducting experiments with the compounds furnished by this company pursuant to our order.

Incidentally, use of a nucleic acid probe according to the present invention with modified DNA, such as 2-O-methyloligoribonucleotide (hereinafter simply called "2-O-Me-oligoribonucleotide), inserted in an oligodeoxyribonucleotide primarily for the determination of RNA, especially for the determination of rRNA can provide preferred results.

Upon determination of RNA by the nucleic acid probe according to the present invention, it is preferred to subject an RNA solution as a sample to heat treatment at 80 to 100° C., preferably 90 to 100° C., most preferably 93 to 97° C. for 1 to 15 minutes, preferably 2 to 10 minutes, most preferably 3 to 7 minutes before hybridization with the probe such that the higher-order structure of RNA can be degraded, as this heat treatment makes it possible to improve the efficiency of hybridization.

It is also preferred to add a helper probe to a hybridization reaction mixture for raising the efficiency of hybridization of the nucleic acid probe of this invention to the hybridization sequence region. In this case, the oligonucleotide of the helper probe can be in an oiigodeoxyribonucleotide, an oligoribonucleotide or an oligonucleotide subjected to similar chemical modification as described above. Examples of the above-described oligonucleotides can include those having the base sequence of (5')TCCTTTGAGT TCCCGGC-CGG A(3') (SEQ ID NO: 52) as the forward type and those having the base sequence of (5')CCCTGGTCGT AAGGGC-CATG ATGACTTGAC GT(3') (SEQ ID NO: 53) as the backward type or the reverse type. Preferred examples of the chemically-modified oligonucleotide can include 2-O-alkyloligoribonucleotides, notably 2-O-Me-oligoribonucleotide.

Where the base strand of the nucleic acid probe according to the present invention is formed of 35 or fewer bases, use of a helper probe is particularly preferred. When a nucleic acid probe according to the present invention longer than a 35-base strand is used, however, it may only be necessary to thermally denature target RNA in some instances.

When the nucleic acid probe according to the present invention is hybridized to RNA as described above, the efficiency of hybridization is enhanced. The fluorescence intensity, therefore, decreases corresponding to the concentration of RNA in the reaction mixture so that RNA can be determined up to a final RNA concentration of about 150 pM.

Accordingly, the present invention also relates to a kit for determining a concentration of a target nucleic acid, which includes or is accompanied by the above-described helper probe in addition to a kit which is adapted to determine the concentration of the target nucleic acid the nucleic acid probe of the present invention and which includes or is accompanied by the nucleic acid probe of this invention.

In determination of RNA by a conventional hybridization assay making use of a nucleic acid probe, an oligodeoxyribonucleotide or oligoribonucleotide has been used as the nucleic acid probe. Because RNA itself has a higher-order solid structure, the efficiency of hybridization between the probe and the target RNA was poor, resulting in quantitation of low accuracy. The conventional methods, therefore, are accompanied by irksomeness that a hybridization reaction is conducted after denaturing RNA and immobilizing denatured RNA on a membrane. The method according to the present invention, on the other hand, uses a nucleic acid probe a ribose portion of which has been modified to have high affinity to a particular structural part of RNA, so that a hybridization reaction can be conducted at a higher temperature compared with the conventional methods. The above-mentioned adverse effects of the high-order structure of RNA can be overcome by simply conducting thermal denaturation as pretreatment and using a helper probe in combination. As a consequence, the efficiency of hybridization in the method according to the present invention is practically as high as 100%, leading to improvements in the accuracy of quantitation. Further, the method according to the present invention is far simpler and easier than the conventional methods.

The probe according to the present invention is formed of 5 to 50 bases, preferably 10 to 25 bases, most preferably 15 to 20 bases. A base number greater than 50 leads to lower permeability through a cell membrane when employed in the FISH method, thereby narrowing an applicable range of the present invention. A base number smaller than 5, on the other hand, tends to induce non-specific hybridization and, therefore, results in a large determination error.

The oligonucleotide in the nucleic acid probe in the present invention can be produced by a conventional production process for general oligonucleotides. It can be produced, for example, by a chemical synthesis process or by a microbial process which makes use of a plasmid vector, a phage vector or the like (Tetrahedron Letters, 22, 1859-1862, 1981; Nucleic Acids Research, 14, 6227-6245, 1986). Further, it is suitable to use a nucleic acid synthesizer currently available on the market (for example, "ABI 394", trade name, manufactured by Perkin-Elmer Corp., Norwalk, Conn., U.S.A.). Further, there are some enterprises which offer custom DNA synthesis services on commercial basis. It is, therefore, most convenient to conduct only the designing of base sequences and to order their synthesis to such enterprises. Illustrative of such enterprises are Takara Shuzo Co., ltd., Kyoto, Japan and Espec Oligo Service Corp., Ibaraki, Japan.

To label the oligonucleotide with the fluorescent dye and the quencher substance, desired one of conventionally-known labeling methods can be used (Nature Biotechnology, 14, 303-308, 1996; Applied and Environmental Microbiology, 63, 1143-1147, 1997; Nucleic Acids Research, 24, 4532-4535, 1996). To conjugate a fluorescent dye and a quencher substance to the 5' end, a linker or spacer, for example, $-(CH_2)_n-SH$ or $-(CH_2)_n-NH_2$ is first introduced into a phosphate group at the 5' end by a method known per se in the art. As such a linker- or spacer-introduced derivative is available on the market, a commercial product may be purchased (Midland Certified Reagent Company). In the above-mentioned example, n ranges from 3 to 8 with 6 or 7 being preferred. The oligonucleotide can be labeled by reacting a SH— or $NH_2$-reactive fluorescent dye or a quencher substance to the linker or spacer. Reversed phase chromatography or the like to provide a nucleic acid probe for use in the present invention can purify the thus-synthesized oligonucleotide, which is labeled with the fluorescent dye.

Further, to conjugate the fluorescent dye or quencher substance to the 3' end of the oligonucleotide, a linker, for example, $-(CH_2)_n-NH_2$ or $-(CH_2)_n-SH$ is introduced onto an OH group on the C atom at the 2'-position or 3'-position of ribose or onto an OH group on the C atom at the 3'-position of deoxyribose. As such a linker-introduced derivative is also available on the market like the above-described ones, a commercial product may be purchased (Midland Certified Reagent Company). As an alternative, a phosphate group may be introduced onto the OH group, followed by the introduction of a linker, for example, $-(CH_2)_n-SH$ or $-(CH_2)_n-NH_2$ onto the OH group of the phosphate group. In these cases, n ranges from 3 to 9, with 4 to 8 being preferred. The oligonucleotide can be labeled by reacting an $NH_2$— or SH-reactive fluorescent dye or a quencher substance to the linker.

For the introduction of the amino group, it is convenient to use a kit reagent [for example, "Uni-link Aminomodifier" (trade name, product of Clontech Laboratories, Inc., Palo Alto, Calif., U.S.A.), or "FluoReporter Kit F-6082, F-6083, F-6084 or F-1022C" (trade name, product of Molecular Probes, Inc.)]. In a manner known per se in the art, molecules of the fluorescent dye can then be conjugated to the oligoribonucleotide. It is also possible to introduce molecules of the fluorescent dye into strands of the probe nucleic acid (ANALYTICAL BIOCHEMISTRY, 225, 32-38, 1998).

When it is desired to introduce an amino group onto a ribose portion, deoxyribose portion, phosphate portion or base portion of an oligonucleotide, a linker, a fluorescent dye or a quencher substance to enhance its reactivity, use of a kit reagent (for example, "Uni-link Aminomodifier", "FluoReporter Kit F-6082, F-6083, F-6084 or F-10220" is convenient. The fluorescent dye and the quencher substance can then be bound to the oligoribonucleotide by a method known per se in the art.

In the above-described synthesis, the introduction of a protecting group to each function group and the elimination of the protecting group can be conducted by conventional, known methods.

The oligonucleotide labeled with the fluorescent dye and the quencher substance can he synthesized as described above. It is desired to purify intermediate synthesis products and the completed synthesis product by liquid chromatography such as reversed phase liquid chromatography. The nucleic acid probe according to the present invention can be obtained as described above.

As is appreciated from the foregoing, the nucleic acid probe according to the present invention can be designed by simply labeling an oligonucleotide, which has a base sequence hybridizable to a target nucleic acid, with a fluorescent dye and a quencher substance. Its designing is therefore simple.

The nucleic acid probe according to the present invention can also be readily obtained by ordering its synthesis like the synthesis of the oligonucleotide, provided that only the designing of the probe can be completed.

A description will next be made about the fluorescence quenching probe according to the second aspect of the present.

This probe is characterized in that it is an oligonucleotide labeled with a single fluorescence dye and, when hybridized with a target nucleic acid, the intensity of its fluorescence decreases, It, therefore, has a property opposite to the fluorescence emitting probe.

The oligonucleotide of the fluorescence quenching probe of this invention, which is hybridized to a nucleic acid, is similar to that in the above-described fluorescence emitting probe. Specifically, it can be a chimeric oligonucleotide or a chemically-modified oligonucleotide. As a still further alternative, an oligonucleotide with such a chimeric oligonucleotide or chemically-modified oligonucleotide inserted in its chain can also be used.

The position of the oligonucleotide, where the oligonucleotide is modified by a fluorescent dye, is the same as that of the above-described fluorescence emitting probe.

Similarly to the above-described invention, it is also possible to add a helper probe to a hybridization reaction mixture to further improve the efficiency of hybridization of the nucleic acid probe of this invention to the hybridization sequence region. Further, the base sequence and the number of base chains of the helper probe, the usability of a chemically-modified oligonucleotide, and the like are also as described above in connection with the above-described invention. When hybridized to RNA, the efficiency of hybridization is increased. The intensity of fluorescence is thus decreased corresponding to the amount of RNA in the reaction mixture, thereby making it possible to determine RNA up to a final concentration of about 150 pM.

The thermal modification of RNA and the addition of the helper probe in the determination method of RNA by using the fluorescence quenching probe of this invention are also similar to those described above in connection with the fluorescence emitting probe.

As a consequence, the efficiency of hybridization also reaches substantially 100% in this invention method, leading to an improvement in quantitativeness. In addition, the method is far simpler than the conventional methods.

The number of bases in the probe according to the present invention is similar to that in the above-described invention. No particular limitation is imposed on the base sequence of the probe insofar as it specifically hybridizes to the target nucleic acid. Preferred examples of the base sequence of the probe can include:

1) a base sequence designed such that at least one G (guanine) base exists in the base sequence of the target nucleic acid at a position 1 to 3 bases from the end base portion of the target nucleic acid hybridized to the-probe, (2) a base sequence designed such that plural base pairs of a nucleic acid hybrid complex forms at least one G (guanine) and C (cytosine) pair at an end portion of the probe, and (3) a base sequence designed such that in the probe modified with the fluorescent label at a portion other than the 5' end phosphate group or the 3' end OH group, base pairs in the fluorescence-labeled portion forms at least one G (guanine) and C (cytosine) pair, when the nucleic acid probe labeled with the fluorescent dye is hybridized with the target nucleic acid.

The preparation process of the oligonucleotide of the nucleic acid probe according to the present invention and the labeling method of the oligonucleotide with the fluorescent dye are similar to those described above in connection with the above-described invention.

Further, fluorescent dye molecules can also be introduced into the chain of the nucleic acid probe [ANALYTICAL BIOCHEMISTRY, 225, 32-38 (1998)].

The nucleic acid probe according to the present invention can be prepared as described above. A preferred probe form is one labeled with a fluorescent dye at the 3' or 5' end and containing G or C as the base at the labeled end. If the 5' end is labeled and the 3' end is not labeled, the OH group on the C atom at the 3'-position of the 3' end ribose or deoxyribose or the OH group on the C atom at the 2'-position of the 3' end ribose may be modified with a phosphate group or the like although no limitation is imposed in this respect.

In addition, a nucleic acid probe according to the present invention can also be prepared by modifying C or G in the chain of a probe.

The present invention, in the third aspect thereof, is an invention making use of such fluorescence emitting probes and fluorescence quenching probes as described above.

1) Determination Kits and Determination Devices

A target nucleic acid can be easily and accurately determined in a short time when a fluorescence emitting probe or a fluorescence quenching probe (hereinafter collectively called a "nucleic acid probe of the present invention" for the sake of brevity unless otherwise specifically indicated) is hybridized with the target nucleic acid and a change in the intensity of fluorescence after the hybridization (an increase in the intensity of fluorescence in the case of the fluorescence emitting probes; a decrease in the intensity of fluorescence in the case of the fluorescence quenching probes) is measured. Use of the nucleic acid probe of the present invention also makes it possible to determine RNA although its determination has heretofore been difficult.

Accordingly, the present invention also relates to a kit for measuring a concentration of a target nucleic acid, which includes or is accompanied by the nucleic acid probe according to the present invention.

Use of the nucleic probe according to the present invention is not limited to the determination of a nucleic acid, but it can also be suitably applied to methods for analyzing or determining polymorphism or mutation of a target nucleic acid. In particular, its application to a device for the determination of a concentration of a target nucleic acid {a DNA chip [Tanpakushitsu, Kakusan, Koso (Proteins, Nucleic Acids, Enzymes), 43, 2004-2011 (1998)]} provides a more convenient device for the determination of the concentration of the target nucleic acid. The method for analyzing or determining polymorphism and/or mutation of the target nucleic acid by using the device is an extremely convenient method. Described specifically, when the nucleic acid probe of this invention is a fluorescence quenching probe, the intensity of fluorescence upon its hybridization with the target nucleic acid varies depending on whether or not a GC pair is formed. It is, therefore, possible to analyze or determine polymorphism and/or mutation of a target nucleic acid by hybridizing the nucleic acid probe according to the present invention to the target nucleic acid and then measuring the intensity of fluorescence. Specific methods will be described in Examples. In this case, the target nucleic acid can be an amplified or extracted product obtained by desired one of nucleic acid amplification methods. Further, no particular limitation is imposed on the kind of the target nucleic acid. They are however required to contain a guanine base or cytosine base in strands thereof or at ends thereof, because the intensity of fluorescence would otherwise not decrease. The method of the present invention can, therefore, analyze or determine a mutation or substitution such as G→A, C←A, C→T, C←T, G→C or G←C, specifically, polymorphism such as single nucleotide polymorphism (SNP). Incidentally, it is the current practice to perform an analysis of polymorphism by determining the base sequence of a target nucleic acid in accordance with the Maxam-Gilbert method or the dideoxy method.

Inclusion of the nucleic acid probe according to the present invention in a kit for analyzing or determining polymorphism and/or mutation of a target nucleic acid, therefore, makes it possible to suitably use the kit as a kit for the analysis or determination of the polymorphism and/or mutation of the target nucleic acid.

When analyzing data obtained by the method of the present invention for the analysis or determination of polymorphism and/or mutation of a target nucleic acid, a processing step may be added to correct the intensity of fluorescence, which is emitted from the reaction system when the target nucleic acid is hybridized with the nucleic acid probe of the present invention by the intensity of fluorescence emitted from the reaction system when the target nucleic acid and the nucleic acid probe are not hybridized with each other. The data so processed are provided with high reliability.

Accordingly, the present invention also provides a data analysis method for the method which analyzes or measures polymorphism and/or mutation of a target nucleic acid.

The present invention also features a system for analyzing or determining polymorphism and/or mutation of a target nucleic acid, which has processing means for correcting a fluorescence intensity of a reaction system, in which the target nucleic acid is hybridized with the nucleic acid probe according to the present invention, in accordance with a fluorescence intensity of the reaction system in which the target nucleic acid is not hybridized with the nucleic acid probe according to the present invention.

The present invention further features a computer-readable recording medium with procedures recorded as a program therein for making a computer perform a processing step in which, when analyzing data obtained by the method for analyzing or determining polymorphism and/or mutation of a target nucleic acid, a fluorescence intensity of a reaction system, in which the target nucleic acid is hybridized with the nucleic acid probe according to the present invention, is corrected in accordance with a fluorescence intensity of the reaction system in which the target nucleic acid or gene is not hybridized with the nucleic acid probe according to the present invention.

The probe according to the present invention may be immobilized on a surface of a solid (support layer), for example, on a surface of a slide glass. In this case, the probe may preferably be immobilized on the end not labeled with the fluorescent dye. The probe of this form is now called a "DNA chip". These DNA chips can be used for monitoring gene expressions, determining base sequences, analyzing mutations or analyzing polymorphisms such as single nucleotide polymorphism (SNP). Needless to day, they can also be used as devices (chips) for determining nucleic acids.

To bind the probe of the present invention, for example, to a surface of a slide glass, a slide glass coated with polycations such as polylysine, polyethyleneimine or polyalkylamine, a slide glass with aldehyde groups introduced thereon, or a slide glass with amino groups introduced thereon is first provided. Binding can then be achieved, for example, by i) reacting phosphate groups of the probe to the slide glass coated with the polycations, ii) reacting a probe, in which amino groups have been introduced, to the slide glass on which aldehyde groups have been introduced or iii) reacting a probe, in which PDC (pyridinium dichlomate) residual groups, amino groups or aldehyde groups have been introduced, to the slide glass on which amino groups have been introduced (Fodor, P. A., et al , Science, 251, 767-773, 1991; Schena, W., et al., Proc. Natl. Acad. Sci., U.S.A., 93, 10614-10619, 1996; McGal, G., et al., Proc. Natl. Acad. Sci., U.S.A., 93, 13555-13560, 1996; Blanchad, A. P., et al., Biosens. Bioelectron., 11, 687-690, 1996).

A device having nucleic acid probes of the invention arranged and bound in an arrayed form on a surface of a solid support permits more convenient determination of a nucleic acid.

In this case, the formation of a device by individually binding many probes of this invention, the base sequences of which are different from each other, on a surface of the same solid support makes it possible to simultaneously detect and quantitate a variety of target nucleic acids.

Preferably, this device may be designed such that each probe is provided on a side of the solid support, said side being opposite to the side to which the probe is bound, with at least one temperature sensor and at least one heater at an area of the solid support, where the probe is bound, can be controlled to meet optimal temperature conditions.

For this device, probes other than nucleic acid probes of the present invention, for example, nucleic acid probes of a construction designed such that two different fluorescent dyes are contained per molecule and each of the probes either quenches or emits fluorescence owing to interaction between the two fluorescent dyes when the probe is not hybridized with its corresponding target nucleic acid but either emits fluorescence or quenches when the probe hybridizes to the target nucleic acid, specifically, a device with molecular beacons described above (Tyagi et al., Nature Biotech., 14, 303-308, 1996) or the like bound thereon can also be used suitably. These devices, therefore, are embraced within the technical scope of the present invention.

Fundamental operations in the determination method making use of the device according to the present invention are simply to place a solution, which contains a target nucleic acid such as mRNA, cDNA or rRNA, on the solid support on which the nucleic probes are bound and then to induce hybridization. As a result, a change in the intensity of fluorescence takes place corresponding to the concentration of the target nucleic acid, and the target nucleic acid can then be detected and quantitated from the change in the intensity of fluorescence. Further, binding of many nucleic acid probes of different base sequences on a surface of a single support makes it possible to determine concentrations of many target nucleic acids at the same time. As this device can be used for exactly the same application as a DNA chip, that is, for the determination of the concentrations of the target nucleic acids, it is a novel DNA chip. Under reaction conditions optimal for the target nucleic acid, the nucleic acids other than the target nucleic acid do not change the intensities of fluorescence emitted from the probe. No operation is, therefore, needed for washing off the unreacted nucleic acids. Further, independent temperature control of the individual nucleic acid probes according to the present invention by their corresponding microheaters makes it possible to control the probes under their optimal reaction conditions, respectively. Accurate determination of concentrations is therefore feasible. In addition, a denaturation curve between each nucleic acid probe of this invention and its corresponding target nucleic acid can be analyzed by continuously changing the temperature with the microheater and measuring the intensity of fluorescence during the changing of the temperature. From differences in such denaturation curves, it is possible to determine properties of the hybridized nucleic acid and also to detect SNP.

Further, the device also makes it possible to conduct amplification of a gene by PCR or the like and detection of the gene at the same time.

According to each conventional device for determining a concentration of a target nucleic acid, a nucleic acid probe not modified with a fluorescent dye is bound or fixed on a surface of a solid support and, subsequent to hybridization with the target nucleic acid labeled with the fluorescent dye, an unhybridized portion of the target nucleic acid is washed off, followed by the measurement of the intensity of fluorescence from the remaining fluorescent dye.

To label the target nucleic acid with the fluorescent dye, the following steps can be followed, for example, when specific mRNA is chosen as a target: (1) mRNA extracted from cells is extracted in its entirety, and (2) using a reverse transcriptase, cDNA is synthesized while inserting a nucleoside modified by the fluorescent dye. These operations are not needed in the present invention.

A number of various probes are applied in spots on the device. Optimal hybridization conditions, for example, temperatures or the like for nucleic acids to be hybridized to the individual probes are different from each other. Theoretically speaking, it is therefore necessary to conduct a hybridization reaction and a washing operation under optimal conditions for each probe (at each spot). This is however physically impossible. For all the probes, hybridization is conducted at the same temperature and further, washing is also carried out at the same temperature with the same washing solution. The device is, therefore, accompanied by a drawback that a nucleic acid does not hybridize although its hybridization is desired or that, even if its hybridization takes place, the nucleic acid is readily washed off as the hybridization is not strong. For these reasons, the accuracy of quantitation of the nucleic acid is low. The present invention does not have such a drawback because the above-mentioned washing operation is not needed. Further, a hybridization reaction can be conducted at an optimal temperature for each probe of the present invention by independently arranging a microheater at the bottom of each spot and controlling the hybridization temperature. Accordingly, the accuracy of quantitation has been significantly improved in the present invention.

2) Determination Method of a Target Nucleic Acid

In the present invention, use of the above-described nucleic acid probe, determination kit or device makes it possible to specifically determine a concentration of a target nucleic acid with ease in a short time. A description will hereinafter be made of the determination method.

In the determination method according to the present invention, the above-described nucleic acid probe is added to a measurement system and is caused to hybridize to a target nucleic acid. This hybridization can be effected by a conventionally-known method (Analytical Biochemistry, 183, 231-244, 1989; Nature Biotechnology, 14, 303-308, 1996; Applied and Environmental Microbiology, 63, 1143-1147, 1997). As conditions for hybridization, the salt concentration may range from 0 to 2 molar concentration, preferably from 0.1 to 1.0 molar concentration, and the pH may range from 6 to 8, preferably from 6.5 to 7.5.

The reaction temperature may preferably be in a range of the Tm value of the nucleic acid hybrid complex, which is to be formed by hybridization of the nucleic acid probe to the specific site of the target nucleic acid, ±10° C. This temperature range can prevent non-specific hybridization. A reaction temperature lower than Tm-10° C. allows non-specific hybridization, while a reaction temperature higher than Tm+10° C. allows no hybridization. Incidentally, a Tm value can be determined in a similar manner as in an experiment which is needed to design the nucleic acid probe for use in the present invention. Described specifically, an oligonucleotide which is to be hybridized with the nucleic acid probe of this invention (and has a complementary base sequence to the nucleic acid probe) is chemically synthesized by the above-described nucleic acid synthesizer or the like, and the Tm value of a nucleic acid hybrid complex between the oligonucleotide and the nucleic acid probe is then measured by a conventional method.

The reaction time may range from 1 second to 180 minutes, preferably from 5 seconds to 90 minutes. If the reaction time is shorter than 1 second, a substantial portion of the nucleic acid probe according to the present invention remains unreacted in the hybridization. On the other hand, no particular advantage can be brought about even if the reaction time is set excessively long. The reaction time varies considerably depending on the kind of the nucleic acid, namely, the length or base sequence of the nucleic acid.

In the present invention, the nucleic acid probe is hybridized to the target nucleic acid as described above. The intensity of fluorescence emitted from the fluorescent dye is measured both before and after the hybridization, and a decrease in fluorescence intensity after the hybridization is then calculated. As the decrease is proportional to the concentration of the target nucleic acid, the concentration of the target nucleic acid can be determined.

The concentration of the target nucleic acid in the reaction mixture may range from 0.1 to 10.0 nM, while the concentration of the probe in the reaction mixture may range from 1.0 to 25.0 nM. Upon preparation of a working curve, the nucleic acid probe of the present invention may desirably be used at ratios of from 1.0 to 2.5 relative to the target nucleic acid.

Upon actually determining the concentration of a target nucleic acid, the concentration of which is unknown, in a sample, a working curve is first prepared under the below-described conditions. A corresponding probe according to the present invention is added at plural concentrations to aliquots of the sample, respectively, followed by the measurement of changes in the intensity of fluorescence from the respective aliquots. The probe concentration, which corresponds to the greatest one of the change in fluorescence intensity so measured, is chosen as a preferred probe concentration. Based on the change in fluorescence intensity measured at the preferred probe concentration, a quantitated value of the target nucleic acid can be determined from the working curve.

A description has been made about the principle of the method of the present invention for the determination of a concentration of a nucleic acid. The present invention can be applied to various nucleic acid determination methods, for example, FISH methods, PCR methods, LCR methods, SD methods, competitive hybridizations, and TAS methods.

Examples of these applications will hereinafter be described.

① Application to FISH Methods

The method of the present invention can be applied to nucleic acids contained in cells of microorganisms, plants or animals or those contained in homogenates of the respective cells. The method of the present invention can also be suitably applied to nucleic acids in cells of a cultivation system of microorganisms (e.g., a co-cultivation system of microorganisms or a symbiotic cultivation system of microorganisms), in which various kinds of microorganisms are contained together or a microorganism and other animal- or plant-derived cells are contained together and cannot be isolated from each other, or in a homogenate or the like of the cells of the cultivation system. The term "microorganisms" as used herein means microorganisms in general sense, and no particular limitation is imposed thereon. Examples of such microorganisms can include eukaryotic microorganisms and prokaryotic microorganisms, and also mycoplasmas, virus and rickettsias. The term "a nucleic acid" as used in connection with such a microorganism system means a nucleic acid with a base sequence specific to cells of a cell strain which is desired to be investigated, for example, as to how it is acting in the microorganism strain. Illustrative examples can include 5S rRNAs, 16S rRNAs and 23S rRNAs of certain specific cell strains and particular sequences of their gene DNAs.

According to the present invention, a nucleic acid probe is added to a co-cultivation system of microorganisms or a symbiotic cultivation system of microorganisms and the concentration of 5S rRNA, 16S rRNA or 23S rRNA of a particular cell strain or its gene DNA, thereby making it possible to determine the viable count of the particular strain in the system. Incidentally, a viable count of a particular cell strain in a co-cultivation system of microorganisms or a symbiotic cultivation system of microorganisms can be determine by adding the nucleic acid probe to a homogenate of the system and then measuring a change in fluorescence emission from the fluorescent dye before hybridization relative to fluorescence emission from the fluorescent dye after the hybridization. It is to be noted that this method also falls within the technical scope of the present invention.

The above-described determination method can be carried out as will be described hereinafter. Before the addition of the nucleic acid probe of the present invention, the temperature, salt concentration and pH of the co-cultivation system of microorganisms or the symbiotic cultivation system of microorganisms are adjusted to meet the conditions described above. It is also preferable to adjust the concentration of the specific cell strain, which is contained in the co-cultivation system of microorganisms or the symbiotic cultivation system of microorganisms, to $10^7$ to $10^{12}$ cells/mL, preferably $10^9$ to $10^{10}$ cells/mL in terms of viable count. These adjustments can be achieved by dilution, centrifugal or like concentration, or the like. A viable count smaller than $10^7$ cells/mL results in low fluorescence intensity and greater determination error. A viable count greater than $10^{12}$ cells/mL, on the other hand, leads to excessively high fluorescence intensity, so that the viable count of the particular microorganism cannot be determined quantitatively. However, this range depends upon the performance of a fluorimeter to be used.

The concentration of the nucleic acid probe of the present invention to be added depends upon the viable count of the particular cell strain in the co-cultivation system of microorganisms or the symbiotic cultivation system of microorganisms and, at a viable count of $10^8$ cells/mL, may be in a range of from 0.1 to 10.0 nM, preferably in a range of from 0.5 to 5 nM, more preferably 1.0 nM. A probe concentration lower than 0.1 nM cannot provide any data which accurately reflects the viable count of the particular microorganism. The optimal probe concentration, however, cannot be specified in any wholesale manner because it depends upon the concentration of a target nucleic acid in cells.

Upon hybridizing the nucleic acid probe to the 5S rRNA, 16S rRNA or 23S rRNA of the particular cell strain or its gene DNA in the present invention, the reaction temperature may be set as described above. Further, the hybridization time may also be set as described above.

The nucleic acid probe is hybridized to the 5S rRNA, 16S rRNA or 23S rRNA of the particular cell strain or its gene DNA under such conditions as described above. Intensities of fluorescence from the fluorescent dye in the co-cultivation system of microorganisms or the symbiotic cultivation system of microorganisms before and after the hybridization are then measured.

In the present invention, no particular limitation is imposed on components other than the microorganisms in the co-cultivation system of microorganisms or the symbiotic cultivation system of microorganisms, insofar as the components do not interfere with the hybridization between the nucleic acid probe according to the present invention and the 5S rRNA, 16S rRNA or 23S rRNA or its gene DNA and further, do not inhibit the emission of fluorescence from the fluorescent dye or the action of the quencher substance labeled on the oligonucleotide. For example, phosphates such as $KH_2PO_4$, $K_2HPO_4$, $NaH_2PO_4$, and $Na_5HPO_4$, inorganic nitrogen compounds such as ammonium sulfate, ammonium nitrate and urea, various salts of metal ions such as magnesium, sodium, potassium and calcium ions, various salts such as the sulfates, hydrochlorides, carbonates and the like of trace metal ions such as manganese, zinc, iron and cobalt ions, and vitamins may be contained to adequate extent. If the above-described interference or inhibition is observed, it may be necessary to separate cells of the plural microorganisms from the cultivation system by an operation such as centrifugal separation and then to resuspend them in a buffer or the like.

Usable examples of the buffer can include various buffers such as phosphate buffer, carbonate buffer, Tris-HCl buffer, Tris-glycine buffer, citrate buffer, and Good's buffer. The buffer should be adjusted to a concentration not inhibiting the hybridization or the emission of fluorescence from the fluorescent dye. This concentration depends upon the kind of the buffer. The pH of the buffer may range from 4 to 12, with 5 to 9 being preferred.

② Application to PCR Methods

The present invention can be applied to any method insofar as it is a PCR method. A description will hereinafter be made of an application of the present invention to a real-time quantitative PCR method.

In the real-time quantitative PCR method, PCR is conducted using a specific nucleic acid probe according to the present invention, and a change in fluorescence emission from the florescent dye after a reaction relative to fluorescence emission from the fluorescent dye before the reaction is determined in real time.

The term "PCR" as used herein means a variety of PCR methods. Examples can include RT-PCR, RNA-primed PCR, stretch PCR, reverse PCR, PCR making use of an Alu sequence, multiple PCR, PCR making use of a mixed primer, and PCR making use of PNA. Further, the term "quantitative" means, in addition to quantitation in general sense, quantitation of such an extent as detection as described above.

As described above, the term "target nucleic acid" as used herein means a nucleic acid the existing amount of which is intended to be determined, irrespective whether it is in a purified form or not and further irrespective of its concentration. Various other nucleic acids may also exist together with the target nucleic acid. For example, the target nucleic acid may be a specific nucleic acid in a co-cultivation system microorganisms (a mixed system of RNAs or gene DNAs of plural microorganisms) or a symbiotic cultivation system of microorganisms (a mixed system of RNAs or gene DNAs of plural animals, plants and/or microorganisms), the amplification of which is intended. Purification of the target nucleic acid, if needed, can be conducted by a method known per se in the art. For example, purification can be effected using a purification kit or the like available on the market.

The conventionally-known quantitative PCR methods individually amplify, in the presence of Mg ions, a target nucleic acid by using dATP, dGTP, dCTP, dTTP or dUTP, a target nucleic acid (DNA or RNA), Taq polymerase, a primer, and a nucleic acid labeled with a fluorescent dye or an intercalator while repeatedly changing the temperature between low and high levels, and monitor increases in fluorescence emission from the fluorescent dye in real time in the course of the amplification [Jikken Igaku (laboratory Medicine), 15(7), 46-51, Yodosha (1997)].

On the other hand, the quantitative PCR method according to the present invention is characterized in that the target nucleic acid is amplified by using the nucleic probe of the present invention and a change in fluorescence emission from the fluorescent dye, specifically, an increase in fluorescence emission in the case of the fluorescence emitting probe or a decrease in fluorescence emission in the case of the fluorescence quenching probe is determined. The number of bases in a preferred probe of the present invention for use in the quantitative PCR according to the present invention may be from 5 to 50, preferably from 10 to 25, notably from 15 to 20. No particular limitation is imposed on the probe insofar as it hybridizes to amplification products of the target nucleic acid in PCR cycles. The probe may be designed in either a forward type or a reverse type.

For example, the following designs can be mentioned when the nucleic acid probe is a fluorescence emitting probe. The above-described fluorescence emitting probes are all usable. Most suitable ones are those not labeled at the 3' ends for the reasons to be mentioned next. As the probe is used as a primer, the amount of the target nucleic acid labeled with the fluorescent dye, namely, the quencher substance and fluorescent dye increases with the cycle of the reaction, so that the intensity of florescence in the reaction system at the time of the hybridization increases with the cycle of the reaction. Needless to say, those labeled at the 3' end can also be used sufficiently. In this case, they can be used as simple nucleic acid probes.

The followings can be mentioned as illustrative examples of the fluorescence quenching probe:

(1) A probe labeled, at an portion, preferably, an end thereof, with a fluorescent dye useful in the practice of the present invention. The base sequence of the probe is designed such that, when hybridizes to a target nucleic acid, at least one G (guanine) base exists in the base sequence of the target nucleic acid at a position 1 to 3 bases from the end base of the target nucleic acid hybridized on the end portion or end of the probe where the probe is labeled with the fluorescent dye.

(2) A probe similar to the probe (1) except that the probe is labeled at the 3' end thereof with the fluorescent dye.

(3) A probe similar to the probe (1) except that the 5' end thereof with the fluorescent dye.

(4) A nucleic acid probe the base sequence of which is designed such that, when the probe hybridizes to a target nucleic acid, plural base pairs in a probe-nucleic acid hybrid complex form at least one G (guanine) and C (cytosine) pair at the end portion.

(5) A probe similar to the probe (4), wherein the probe has G or C as a 3' end base and is labeled at the 3' end thereof with a fluorescent dye.

(6) A probe similar to the probe (4), wherein the probe has G or C as a 5' end base and is labeled at the 5' end thereof with a fluorescent dye.

(7) A probe similar to anyone of the probes (1)-(6) except that the OH group on the C atom at the 3'-position of ribose or deoxyribose at the 3' end or the OH group on the C atom at the 3'- or 2'-position of ribose at the 3' end has been phosphorylated.

(8) a nucleic acid probe labeled with the fluorescent dye at a modification portion other than the phosphate group on the 5' end or the OH group on the 3' end hand having a base sequence designed such that, when the probe hybridizes to a target nucleic acid, plural base pairs in a probe-nucleic acid hybrid complex form at least one G (guanine) and C (cytosine) pair at the modification portion.

(9) a nucleic acid probe similar to any one of the probe(s) (1)-(6) except that the oligonucleotide of the probe has been chemically modified.

(10) A nucleic acid probe the base sequence of which is designed such that, when the probe hybridizes to a target nucleic acid, plural base pairs in a probe-nucleic acid hybrid complex form at least one G (guanine) and C (cytosine) pair and the G or C forming the base pair is modified by a fluorescent dye at a position other than the phosphate group on the 5' end or the OH group on the 3' end.

In the case of the probe (6), the 3' or 5' end may not be designed to G or C due to the base sequence of a target nucleic acid. If this should be the case, 5'-guanylic acid or guanosine or 5'-cytidylic acid or cytidine may be added to the 5' end of an oligonucleotide designed as a primer from the base sequence of the target nucleic acid. The probe so obtained can still achieve the objects of the present invention adequately. The objects of the present invention can also be adequately achieved by adding 5'-guanylic acid or 5'-cytidylic acid to the 3' end. The expression "nucleic acid probe designed such that the 3' end or 5' end base thereof becomes G or C" as used herein is, therefore, defined to embrace not only probes designed based on the base sequence of the target nucleic acid but also probes added at the 5' end thereof with 5'-guanylic acid or 5'-cytidylic acid or guanosine or 5'-cytidylic acid or cytidine and probes added at the 5' end thereof with 5'-guanylic acid or 5'-cytidylic acid.

In particular, the above-described probe (7) of the present invention is designed such that it is not used as a primer. PCR is conducted by using a single probe of the present invention as opposed to two (fluorescent-dye-labeled) probes needed in a real-time quantitative PCR method making use of the FRET phenomenon. The probe is added to a PCR reaction system, and PCR is then conducted. During a nucleic acid extending reaction, the probe which has been in a form hybridized with the target nucleic acid or amplified target nucleic acid is degraded by polymerase and is dissociated off from the nucleic acid hybrid complex. The intensity of fluorescence of the reaction system at this time or the reaction system in which a nucleic acid denaturing reaction has completed is measured. Further, the intensity of fluorescence of the reaction system in which the target nucleic acid or amplified target nucleic acid has hybridized with the probe (i.e., the reaction system at the time of an annealing reaction or at the time of the nucleic acid extending reaction until the probe is eliminated from the nucleic acid hybrid complex by polymerase) is measured. By calculating a decrease in the former fluorescence intensity based on the latter fluorescence intensity, the concentration of the amplified nucleic acid is determined. The intensity of fluorescence is high when the probe has completely dissociated from the target nucleic acid or amplified target nucleic acid by the nucleic acid denaturing reaction or when the probe has been degraded out from the hybrid complex of the probe and the target nucleic acid or amplified nucleic acid at the time of extension of the nucleic acid. However, the intensity of fluorescence of the reaction system in which an annealing reaction has been completed and the probe has fully hybridized to the target nucleic acid or amplified target nucleic acid or of the reaction system until the probe is degraded out of the hybrid complex of the probe and the target nucleic acid or amplified target nucleic acid by polymerase at the time of a nucleic acid extending reaction is lower than the former. The decrease in the intensity of fluorescence is proportional to the concentration of the amplified nucleic acid.

In this case, the base sequence of the probe (7) may desirably be designed such chat the Tm of a nucleic acid hybrid complex, which is available upon hybridization of the probe with the target nucleic acid, falls within a range of the Tm value of the hybrid complex of the primer ±15° C., preferably ±5° C. If the Tm of the probe is lower than (the Tm value of the primer −5° C.), especially (the Tm value of the primer −15° C.), the probe does not hybridize so that no decrease takes place in the fluorescence emission from the fluorescent dye. If the Tm of the probe is higher than (the Tm value of the primer +5° C.), especially (the Tm value of the primer +15° C.), the probe also hybridizes to nucleic acid or acids other than the target nucleic acid so that the specificity of the probe is lost.

The probes other than the probe (7), especially the probe (6) is added as a primer to PCR reaction systems. Except for the PCR method according to the present invention, no PCR method is known to make use of a primer labeled further with a fluorescent dye. As the PCR reaction proceeds, the amplified nucleic acid is progressively labeled with the fluorescent dye useful in the practice of the present invention. Accordingly, the intensify of fluorescence of the reaction system in which the nucleic acid denaturing reaction has completed is high but, in the reaction system in which the annealing reaction has completed or the nucleic acid extending reaction is proceeding, the intensity of fluorescence of the reaction system is lower than the former intensity of fluorescence.

The PCR reaction can be conducted under similar conditions as in conventional PCR methods. It is, therefore, possible to conduct amplification of a target nucleic acid in a reaction system the concentration of Mg ions in which is low (1 to 2 mM). Needless to say, the present invention can also be conducted even in a reaction system in which Mg ions are contained at such a high concentration (2 to 4 mM) as that employed in the conventionally-known quantitative PCR methods.

In the PCR method according to the present invention, Tm value can be determined by conducting the PCR of the present invention and then analyzing the melting curve of the nucleic acid with respect to the amplification products. This method is a novel analysis method of a melting curve of a nucleic acid. In this method, the nucleic acid probe employed as a nucleic acid probe or primer in the PCR method of the present invention can be used suitably.

In this case, designing of the base sequence of the probe according to the present invention into a sequence complementary with a region containing SNP (single nucleotide polymorphism) makes it possible to detect SNP from a difference, if any, in a dissociation curve of the nucleic acid from the probe of the present invention by analyzing the dissociation curve after completion of PCR. If a base sequence complementary with an SNP-containing sequence is used as a sequence for the probe of the present invention, a Tm value available from a dissociation curve between the sequence of the probe and the SNP-containing sequence becomes higher than a Tm value available from a dissociation curve between the sequence of the probe and the SNP-free sequence.

③ Data Analysis Method

The present invention, in the third aspect thereof, relates to the method for analyzing data obtained by the above-described real-time quantitative PCR method.

A real-time quantitative PCR method is now practiced in real time by a system which is composed of a reactor for conducting PCR, an equipment for detecting fluorescence emission from a fluorescent dye, a user interface, namely, a computer-readable recording medium with various procedures of a data analysis method recorded as a program (also called "sequence detection software system"), and a computer for controlling them and analyzing data. Determination by the present invention is also conducted by such a system.

A description will first be made of an analyzer for real-time quantitative PCR. Any system can be used in the present invention insofar as it can monitor PCR in real time. Particularly suitable examples can include "ABI PRISM™ 7700 Sequence Detection System (SDS 7700)" (manufactured by Perkin-Elmer Applied Biosystems, Inc., U.S.A.) and "LightCycler™ System" (manufactured by Roche Diagnostics, Mannheim, Germany).

The above-described reactor is an apparatus for repeatedly conducting a thermal denaturing reaction of a target nucleic acid, an annealing reaction and an extending reaction of the nucleic acid (these reactions can be repeatedly conducted, for example, by successively changing the temperature to 95° C., 60° C. and 72° C. The detection system comprises a fluorescence emitting argon laser, a spectrograph and a CCD camera. Further, the computer-readable recording medium with the various procedures of the data analysis method recorded as the program is used by installing it in the computer, and contains a program recorded therein for controlling the above-described system via the computer and also for processing and analyzing data outputted from the detection system.

The data analysis program recorded in the computer-readable recording medium comprises the following steps: measuring the intensity of fluorescence cycle by cycle, displaying each measured fluorescence intensity as a function of cycles, namely, as a PCR amplification plot on a display of the computer, calculating a threshold cycle number (Ct) at which the intensity of fluorescence is begun to be detected, forming a working line useful in determining from Ct values the number of copies of the nucleic acid in the sample, and printing data and plot values in the respective steps. When PCR is exponentially proceeding, a linear relationship is established between the logarithm of the number of copies of the target nucleic acid at the time of initiation of PCR and Ct. It is therefore possible to calculate the number of copies of the target nucleic acid at the time of initiation of PCR by forming a working line based on known copy numbers of the target nucleic acid and detecting the Ct of a sample which contains the target nucleic acid the number of copies of which is unknown.

The PCR-related invention such as the above-described data analysis method is an invention for analyzing data obtained by such a real-time quantitative PCR method as described above. Its respective features will be described hereinafter. A first feature resides in a processing step for correcting a fluorescence intensity of a reaction system, which is measured when the nucleic acid amplified in each cycle is conjugated with the fluorescent dye or when the amplified nucleic acid hybridizes to a nucleic acid probe according to the present invention in the method for analyzing data obtained by the real-time quantitative PCR method, by a fluorescence intensity of the reaction system as obtained when the above-described conjugate of the fluorescent dye and the nucleic acid or the fluorescent dye-nucleic acid conjugate or the above-described hybrid complex of the nucleic acid probe of the present invention and the target nucleic acid or the nucleic acid hybrid complex has dissociated in each cycle, namely, the first feature resides in a correction-processing step.

As a specific example of "the reaction system . . . when the amplified target nucleic acid is conjugated with the fluorescent dye or when the amplified target nucleic acid hybridizes to a nucleic acid probe according to the present invention", a reaction system upon conducting a nucleic acid extending reaction or annealing at 40 to 85° C., preferably 50 to 80° C. in each cycle of PCR can be mentioned. The actual temperature depends upon the length of the amplified nucleic acid.

Further, "the reaction system . . . when the above-described fluorescent dye-nucleic acid conjugate or the above-described nucleic acid hybrid complex has dissociated" can be a reaction system upon conducting thermal denaturation of the nucleic acid in each cycle of PCR, specifically at a reaction temperature of from 90 to 100° C., preferably 94 to 96° C. Illustrative is a system in which the reaction has been completed.

Any correction processing can be used as the correction processing in the correction processing step insofar as it conforms with the objects of the present invention. Specifically, correction processing including a processing step by the following formula (1) or formula (2) can be exemplified.

$$f_n = f_{hyb,n}/f_{den,n} \quad (1)$$

$$f_n = f_{den,n}/f_{hyb,n} \quad (2)$$

where $f_n$: correction-processed value in an $n^{th}$ cycle as calculated in accordance with the formula (1) or formula (2), $f_{hyb,n}$: intensity value of fluorescence of the reaction system available after the amplified nucleic acid has conjugated to the fluorescent dye or the amplified nucleic acid has hybridized to the nucleic acid probe labeled with the fluorescent dye in the $n^{th}$ cycle, and $f_{den,n}$: intensity value of fluorescence of the reaction system available after the fluorescent dye-nucleic acid conjugate or the nucleic acid hybrid complex has dissociated in the $n^{th}$ cycle.

This step includes a sub-step in which correction-processed values obtained by the above-described processing are displayed on a computer display and/or the correction-processed values are likewise displayed and/or printed in the form of a graph as a function of cycles.

A second feature resides in a data analysis method, which comprises:

Introducing correction-processed values, which have been calculated in accordance with the formula (1) or formula (2) in individual cycles, into the following formula (3) or formula (4) to calculate rates or percentages of changes in fluorescence between samples in the individual cycles:

$$F_n = f_n/f_a \quad (3)$$

$$F_n = f_a/f_n \quad (4)$$

where $F_n$: rate or percentage of a change in fluorescence in an $n^{th}$ cycle as calculated in accordance with the formula (3) or formula (4), $f_n$: correction-processed value calculated in the $n^{th}$ cycle as calculated in accordance with the formula (1) or formula (2), and $f_a$: correction-processed value calculated in a given cycle before a change in $f_n$ is observed as calculated in accordance with the formula (1) or formula (2), and in general, a correction-processed value, for example, in one of $10^{th}$ to $40^{th}$ cycles, preferably one of $15^{th}$ to $30^{th}$ cycles, more preferably one of $20^{th}$ to $30^{th}$ cycles is adopted; and comparing the rates or percentages of changes in fluorescence.

This step includes a sub-step in which calculated values obtained by the above-described processing are displayed on a computer display and/or are printed or the calculated values are likewise displayed and/or printed in the form of a graph as a function of cycles. This sub-step may be applied or may not be applied to the correction-processed values obtained by the formula (1) or formula (2).

A third feature resides in a data analysis method, which comprises the following processing steps:

1) performing processing in accordance with the following formula (5), (6) or (7) by using data of rates or percentages of changes in fluorescence as calculated in accordance with said formula (3) or (4):

$$\log_b(F_n), \ln(F_n) \quad (5)$$

$$\log_b\{(1-F_n) \times A\}, \ln\{(1-F_n) \times A\} \quad (6)$$

$$\log_b\{(F_n-1) \times A\}, \ln\{(F_n-1) \times A\} \quad (7)$$

where

A,b: desired numerical values, preferably integers, more preferably natural numbers and, when A=100, b=10, $\{(F_n-1) \times A\}$ is expressed in terms of percentage (%), and $F_n$: rate or percentage of a change in fluorescence in an $n^{th}$ cycle as calculated in accordance with the formula (3) or formula (4), 2) determining a cycle in which said processed value of said processing step 1) has reached a constant value, 3) calculating a relational expression between cycle of a nucleic acid sample of a known concentration and the number of copies of said target nucleic acid at the time of initiation of a reaction, and 4) determining the number of copies of said target nucleic acid in an unknown sample upon initiation of PCR.

Preferably, these steps are performed in the order of 1)→2)→3)→4).

Each of these steps 1) to 3) may include a sub-step in which processed values obtained by the corresponding processing are displayed on a computer display and/or the processed values are likewise displayed and/or printed in the form of a graph as a function of cycles. The step 4) should include at least a printing sub-step as the processed values obtained in the step 4) have to be printed, although the processed values obtained in the step 4) may also displayed on a computer display.

Incidentally, the correction-processed values obtained by the formula (1) or (2) and the calculated values obtained by the formula (3) or (4) may be or may not be displayed on a computer display and/or printed in the form of graphs as a function of cycles, respectively. These displaying and/or printing sub-steps may, therefore, be added as needed.

The above-described data analysis method is particularly effective when decreases in fluorescence emission from the fluorescent dye are measured in the real-time quantitative PCR method, that is, when fluorescence quenching probes are used. As a specific example, the real-time quantitative PCR method according to the present invention, which makes use of a fluorescence quenching probe, can be mentioned.

A fourth feature resides in an analysis system for real-time quantitative PCR, which comprises processing and storing means for performing a data analysis method for the above-described real-time quantitative PCR method of the present invention.

A fifth feature resides in a computer-readable recording medium with individual procedures of a data analysis method, which is adapted to analyze PCR by using the analysis system for the real-time quantitative PCR, stored as a program therein, wherein the program is designed to make a computer perform the individual procedures of the data analysis method of the present invention.

A sixth feature resides in a novel method for determining a nucleic acid, which comprises using the data analysis method, determination and/or analysis system and/or recording medium of the present invention in the nucleic acid determination method.

A seventh feature resides in a method for analyzing data obtained by the above-described method of the present invention for the analysis of a melting curve of a nucleic acid, namely, data obtained by the method of the present invention in which the Tm value of the nucleic acid is determined by conducting PCR.

Specifically, the seventh feature resides in an analysis method, which comprises the following steps: gradually heating a nucleic acid, which has been amplified by the PCR method of the present invention, from a low temperature until complete denaturation of the nucleic acid (for example, from 50° C. to 95° C.; measuring an intensity of fluorescence at short time intervals (for example, at intervals equivalent to a temperature rise of from 0.2° C. to 0.5° C.) during the heating step; displaying results of the measurement as a function of time on a display, namely, a melting curve of the nucleic acid; differentiating the melting curve to obtain differentiated values (−dF/dT, F: intensity of fluorescence, T: time); displaying the differentiated values as derivatives on the display; and determining a point of a inflection from the derivatives. In the present invention, the intensity of fluorescence increases as the temperature rises. Preferable results can be obtained in the present invention by adding to the above-described step a further processing step in which in each cycle, the intensity of fluorescence at the time of the nucleic acid extending reaction, preferably at the time of completion of the PCR reaction is divided by the value of fluorescence intensity at the time of the thermal denaturing reaction.

A measurement and/or analysis system for the real-time quantitative PCR of the present invention, said real-time quantitative PCR including the method of the present invention for the analysis of the melting curve of a nucleic acid added to the above-described novel method of the present invention for the analysis of data obtained by a PCR method, also falls within the technical scope of the present invention.

A still further feature of the present invention resides in a computer-readable recording medium with the individual procedures of the method of the present invention for the analysis of the melting curve of a nucleic acid recorded therein as a program such that the procedures can be performed by a computer or a computer-readable recording medium with the individual procedures of the method of the present invention for the analysis of data obtained by a PCR method recorded therein as a program such that the procedures can be performed by a computer, wherein a program designed to make the computer perform the individual procedures of the method of the present invention for the analysis of the melting curve of the nucleic acid is additionally recorded.

The above-described data analysis methods, systems and recording media of the present invention can be used in a variety of fields such as medicine, forensic medicine, anthropology, paleontology, biology, genetic engineering, molecular biology, agricultural science and phytobreeding. They can be suitably applied to microorganism systems called "co-cultivation systems of microorganisms" or "symbiotic cultivation systems of microorganisms", in each of which various kinds of microorganisms are contained together or a microorganism and other animal- or plant-derived cells are contained together and cannot be isolated from each other. The term "microorganisms" as used herein means microorganisms in general sense, and no particular limitation shall be imposed thereon. Illustrative are eukaryotic microorganisms, prokaryotic microorganisms, mycoplasmas, virus and rickettsias.

The vial count of a particular cell strain in a co-cultivation system of microorganisms or a symbiotic cultivation systems of microorganisms can be determined by determining the number of copies of the 5S rRNA, 16S rRNA or 23S rRNA of the particular cell strain or its gene DNA in the system by using one or more of the above-described data analysis methods, systems and recording media of the present invention, because the number of copies of the gene DNA of 5S rRNA, 16S rRNA or 23S rRNA is specific to each cell strain. In the present invention, the vial count of a particular cell strain can also be determined by applying the real-time quantitative PCR of the present invention to a homogenate of a co-cultivation system of microorganisms or a symbiotic cultivation systems of microorganisms. It shall also be noted that this method also fails with the technical scope of the present invention.

④ Polymorphous Analysis Method

The feature of the polymorphous analysis method according to the present invention resides in the use of the nucleic acid probe of this invention in a conventional polymorphous analysis method to determine a nucleic acid. The term "polymorphous" or "polymorphism" as used herein means biological polymorphous or polymorphism. In the present invention, it means especially the polymorphism of a gene (RNA, DNA, gene) on which the polymorphism is brought about. It has the same meaning as commonly employed these days in molecular biology.

The term "polymorphous analysts" means to analyze and/or determine what polymorphism a gene has.

Currently-available examples of the conventional polymorphous method include SSOP (sequence specific oligonucleotide probe) method, RELP (restriction fragment length polymorphism) method, T-RFLP (terminal restriction fragment length polymorphism) method, SSCP (single strand conformation polymorphism analysis) method, MPH method, CFLP (cleavage fragment length polymorphism) method, SSP (sequence specific primer) method, PHFA (preferential homoduplex formation assay) method, SBT (sequence base typing) method [PCT Ho, Riyo no Tebiki (PCR Methods, Manual for Their Use), Chugai Medical Publishing Co., Ltd. (1998); Tanpakushitsu, Kakusan, Koso (Proteins, Nucleic Acids, Enzymes), 35(17), KYORITSU SHUPPAN CO., LTD. (1990); Jikken Igaku (Laboratory Medicine), 15(7) (special number), Yodosha (1997)]. T-RELP method or CFLP method can be especially suitably applied, although the methods currently used in polymorphous analyses are all usable in the present invention Features of the polymorphous analysis method will hereinafter be described specifically in order.

The first feature resides in a quantitative gene amplification method making use of the nucleic acid probe of this invention. Any quantitative gene amplification method can be adopted insofar as it has quantitativeness. For example, PCR methods can be adopted suitably. Among these, quantitative PCR methods and real-time monitoring, quantitative PCR methods are more preferred.

Examples of conventionally-known, quantitative PCR methods can include RT-PCR, RNA-primed PCR, Stretch PCR, reversed PCR, PCT making use of an Alu sequence, multiple PCR, PCR making use of a mixed primer, and PCR making use of PNA.

According to these conventionally-known, quantitative PCR methods, a target gene is amplified by cycling the temperature between a low temperature and a high temperature in the presence of Mg ions while using dATP, dGTP, dCTP and dTTP or dUTP, a target gene (DNA or RNA), Taq polymerase, a primer and a nucleic acid probe labeled with a fluorescent dye or an intercalator, and an increase in the emission of fluorescence from the fluorescent dye in the course of the amplification is monitored in a real-time manner [Jikken Igaku (Laboratory Medicine), 15(7), 46-51, Yodosha (1997)].

The quantitative PCR method according to the present invention, which makes use of the invention nucleic acid probe, is a method in which the probe labeled with the fluorescent dye is used. It is a quantitative PCR method that makes use of a probe designed such that the intensity of fluorescence from the fluorescent dye changes (specifically, increases in the case of a fluorescence emitting probe or decreases in the case of a fluorescence quenching probe) when the probe hybridizes to a target nucleic acid.

For example, as has been described in detail in connection with the second aspect of the invention, a fluorescence quenching probe is labeled at an end thereof with a fluorescent dye, and its base sequence is designed such that, when the probe hybridizes at the end portion thereof to a target gene, at least one G (guanine) base exists in a base sequence of the target gene at a position 1 to 3 bases from the portion of an end base pair of the target gene hybridized with the probe, whereby the fluorescent dye is reduced in fluorescence emission when the probe hybridizes to the target gene.

Preferably, the fluorescence quenching probe is labeled at the end thereof with the fluorescent dye, and its base sequence is designed such that, when the probe hybridizes to the target gene, base pairs of the hybrid complex of the probe and the target gene forms at least one G (guanine) and C (cytosine) pair (GC base pair) at the end thereof, whereby the fluorescent dye is reduced in the intensity of fluorescence when the probe hybridizes to the target gene.

If the 5' or 3' end cannot be designed to G or C due to the base sequence of a target gene, the objects of the present invention can also be adequately achieved by adding 5'-guanylic acid or 5'-cytidylic acid to the 5' end of an oligonucleotide designed as a primer from the base sequence of the target nucleic acid. The expression "fluorescence quenching probe" is, therefore, defined to embrace not only probes designed based on the base (sequence of the target nucleic acid but also probes added at the 3' or 5' ends thereof, preferably the 5' ends thereof with 5'-guanylic acid or 5'-cytidylic acid.

If it is inconvenient to form the end into C or G, similar fluorescence quenching effect can also be obtained by fluorescence labeling C or G in the chain of a probe or primer.

The nucleic acid probe of this invention to be used contains 5 to 50 bases, preferably 10 to 25 bases, especially preferably 15 to 20 bases. No particular limitation is imposed on its base sequence insofar as the probe hybridizes specifically to the target gene.

According to the quantitative PCR method making use of the fluorescence quenching probe, the target gene can be easily and specifically amplified in short time. When a fluorescence quenching probe labeled at the 5' end thereof with a fluorescent dye is used, a target gene labeled at the 5' end thereof with the fluorescent dye is amplified [Jikken Igaku (Laboratory Medicine), 15(7), Yodosha (1997)].

As a thermal cycler for use in the quantitative PCR method, any one of various equipment currently available on the market can be conveniently used no matter whether or not it permits real-time monitoring. Particularly preferred examples of equipment, which permit real-time monitoring, can include "ABI PRISM™ 7700 Sequence Detection System" (SDS 7700) (trade name; manufactured by Perkin-Elmer Applied Biosystem, Inc., CA, U.S.A.) and "Light-Cycler"™ System" (trade name; manufactured by Roche Diagnostic GmbH, Mannheim, Germany).

Amplification of a gene can be attained under amplifying reaction conditions known to date. It is generally desired to proceed with amplification to an amplification degree which is commonly used. In the course of the amplification of the target gene, the intensity of fluorescence is measured by a fluorimeter. Changes in the intensity of fluorescence are proportional with amplified amounts of the gene. Plotting of the changes in the intensity of fluorescence as a function of time (cycles in the case of PCR) on an ordinary graph paper gives an S-shaped (sigmoid) curve, whereas their plotting on a semilog graph paper gives a line, which linearly increases in the beginning like an exponential function but then forms a curve which reaches a gentle plateau.

As the degree of amplification of the target gene, in other words, the time to stop the amplifying reaction of the gene to improve the quantitativeness of the initial amount of the gene before starting PCR depends upon the purpose of the polymorphous analysis, no particular limitation is imposed thereon. Described specifically, when a polymorphous system is analyzed for only priority polymorphism, it is suited to amplify the target gene for a desired time from the initial observation of a change in the intensity of fluorescence until before the above-described plateau is reached. It is most preferable to stop the reaction in an exponential growth phase [i.e., before reaching a midpoint of the sigmoid curve (a point where a derivative of the curve becomes 0)]. When it is desired to analyze all polymorphous species contained in the polymorphous system, it is desired to conduct several experiments in a trial and error manner to determine a degree of amplification considered to be the best and then to amplify the gene to such extent that genes, which show polymorphism in the reaction system, can all be observed. A method in which amplification is conducted by dividing it in plural stages, in other words, an experiment is conducted at plural degrees of amplification and the results are analyzed as a whole—can also be adopted appropriately, because minor polymorphous species tend to draw a sigmoid curve having large time lags.

When the quantitative PCR method, especially the real-time monitoring quantitative PCR method is performed using the fluorescence quenching probe of this invention as a primer, the fluorescence quenching probe as the primer is used repeatedly for the amplification of the target gene so that the target gene labeled at the 5' end thereof with the fluorescent dye is amplified. The amplified target gene then hybridizes to the corresponding target gene. When this hybridization takes place, the intensity of fluorescence decreases. It is therefore only required to conduct the amplifying reaction to the best degree of amplification in a similar manner as described above while tracing decreases in the intensity of fluorescence. This quantitative PCR method can also be conducted under similar reaction conditions as the conventional PCR methods. Accordingly, amplification of a target gene can be conducted in a reaction system the Mg ion concentration of which is low (1 to 2 mM) or, as was known conventionally, is high (2 to 4 mM).

It is preferred to prepare a working line for the target gene by using an authentic target gene before the amplifying reaction of the target gene. A description will now be made about an illustrative case in which the above-described fluorescence quenching probe was used as a primer and the real-time monitoring quantitative PCR method was conducted.

Plotting of decreases in the intensity of fluorescence as a function of cycles on an ordinary graph paper gives an S-shaped (sigmoid) curve. An exponential relation exists between the number of cycles at a time point where the rate of decrease was the greatest and the initial number of copies of the target gene (the number of copies before the initiation of PCR), that is, the target gene in the initial stage. Advanced preparation of a target straight line, which represents the correlation between the number of cycles and the number of copies at that time point, makes it possible to determine the initial number of copies of the target gene in an unknown sample, namely, the initial amount of the target gene.

Incidentally, the above-described quantitative PCR method making use of the fluorescence quenching probe is a novel method developed by the present inventors.

As the second feature of the quantitative polymorphisms analysis method, it is an analysis method for analyzing data obtained by the quantitative PCR method.

As a matter of fact, it is nothing but a method for analyzing data obtained by the above-described quantitative PCR process. This analysis method is currently most suited for determining the initial amount of the target gene as accurately as possible.

This invention also relates to a reagent kit for use in the above-described quantitative gene amplification process and also to a computer-readable recording medium characterized in that a program for making a computer perform the above-described data analysis method is recorded.

Moreover, the present invention also relates to a data analysis system characterized in that the system is provided with means for conducting the above-described data analysis method.

The third feature of the present invention relates to a method for analyzing polymorphism with respect to genes amplified by the quantitative PCR method according to the present invention.

Now, this polymorphisms analysis method will be described specifically. Among various polymorphisms analysis methods, T-RFLP can be suitably used in the present invention. As an example of the present invention, a gene is amplified by a quantitative PCR method making use of a fluorescence quenching probe as a primer, especially by a real-time monitoring quantitative PCR method, and the initial amount of the gene before PCR is determined. Further, a detailed description will be made about a method for analyzing polymorphism of the amplification products by T-RFLP. Incidentally, the gene amplified by using the fluorescence quenching probe as a primer is labeled at the 5' end thereof with the fluorescent dye useful in the practice of the present invention.

(1) Firstly, the amplification products are digested by a restriction endonuclease. As this restriction endonuclease, the currently known restriction endonucleases are all usable. Illustrative are Bso FI, Hha I, Hph I, Mnl I, Rca I, Alu I and Msp I. Among these, preferred are Rca I, Alu I and Msp I, with Hha I being most preferred. As digesting reaction conditions, conditions generally employed for the currently known genes can be used. If Hha I is chosen as a restriction endonuclease, for example, it is reacted at 37° C. for 6 hours at a restriction endonuclease concentration of 10 units.

(2) Gene fragments digested as described above can preferably be thermally denatured into single-stranded forms. This denaturation treatment can be conducted under usual conditions known to the public. For example, they are treated at 97° C. for 5 minutes and then chilled in ice.

(3) Analysis and Determination of Gene Fragments

In the polymorphisms analysis method of the present invention, only the gene fragments labeled with the fluorescent dye are analyzed and determined by electrophoresis, HPLC, sequencer or the like.

Described specifically, individual bands and band peaks are detected based on fluorescence intensities. This detection can be conducted using an ordinary analyzer currently available on the market. Examples of the analyzer can include "ABI 373A" (trade name, a sequencer manufactured by Applera Corp-Applied Biosystems Group, CT, U.S.A.), "ABI 377" (trade name, a sequencer manufactured by Applera Corp-Applied Biosystems Group, CT, U.S.A.) and "Biofocus 3000" (trade name; manufactured by Bio-Rad Laboratories, Inc. CA, U.S.A.).

In the present invention, appearance of plural bands or plural peaks in the above-described analysis means existence of polymorphism. A single band or a single peak means non-existence of polymorphism. A fluorescence intensity ratio of individual bands or peaks obviously means a polymorphous ratio. As the amount of a target gene before PCR is determined in the quantitative PCR method of the present invention, multiplication of the determined value by the above-described polymorphous ratio makes it possible to determine the initial amounts of the individual species of the polymorphous gene.

A method for obtaining data with respect to polymorphism as described above has been successfully provided for the first time owing to the use of the quantitative PCR method making use of the fluorescence quenching probe of the present invention.

Further, a convenient reagent kit for quantitative polymorphous analysis can also be provided by either including or attaching a reagent kit for the quantitative PCR method.

In addition, additional recording of a program, which is adapted to make a computer perform an analysis of data of the above-described real-time monitoring quantitative PCR, in a computer-readable recording medium—in which a program for making the computer perform the analysis method of data obtained by the above-described polymorphous analysis method has already been recorded—can provide a more convenient, computer-readable recording medium for the analysis of data obtained by the quantitative polymorphous analysis method.

Moreover, combined arrangement of a data analyzer for PCR with a polymorphous analyzer equipped with means for performing the quantitative polymorphisms analysis method can provide a more convenient polymorphisms analyzer.

The present invention will next be described more specifically based on the following Examples and Comparative Examples. Examples 1-7 relate to fluorescence emitting probes according to the present invention.

EXAMPLE 1

Synthesis of Nucleic Acid Probe

Assuming that the base sequence of a target nucleic acid was (5')GGGGGGAAAAAAAAAA(3') (SEQ ID NO: 1) formed of an oligodeoxy-ribonucleotide, synthesis of a nucleic acid probe according to the present invention was conducted in the following order.

Designing of Nucleic Acid Probe

As the base sequence of the target nucleic acid was (5')GGGGGGAAAAAAAAAA(3') (SEQ ID NO: 1), it was possible to readily design the base sequence of the nucleic acid probe as (5')TTTTTTTTTCCCCCC(3') (SEQ ID NO: 48) formed of an oligodeoxyribonucleotide. The nucleic acid probe according to the present invention was designed further as will be described hereinafter. It was decided to label a fluorescent dye, Texas Red, to a phosphate group on the 5' end and a quencher substance, Dabcyl, to an OH group on the 6-C of a base ring of the $6^{th}$ thymine from the 5' end (Design of Texas Red-(5')TTTTTT(Dabcyl-)TTTCCCCCC (3')) (SEQ ID NO: 48).

Using "5'Amino-Modifier C6 Kit" (trade name, product of Glen Research Corporation, VA, U.S.A.), the phosphate group of thymidylic acid was modified with an amino linker (protecting group: MMT). Using "Amino-Modifier C2dT Kit" (trade name, product of Glen Research Corporation, VA, U.S.A.), the OH group on the 6-C of the base ring of thymidine was modified with an amino linker (protecting group: TFA). Using those modified thymidylic acid and thymidine, an oligonucleotide having the following base sequence was synthesized by a DNA synthesizer ("ABI 394") (trade name, manufactured by PerkinElmer Japan Co., Ltd., Japan). Specifically, it was a deoxyribooligonucleotide having the base sequence of (5')TTTTTTTTTCCCCCC(3') (SEQ ID NO: 48), the phosphate group on the 5' end was modified with the amino linker (protecting group MMT), and the Oil group on the 6-C of the base ring of the $6^{th}$ thymine from the 5' end was modified with the amino linker (protecting group: TFA). Incidentally, the synthesis of DNA was conducted by the β-cyanoethylphosphoramidate method. After the synthesis, elimination of the protecting groups was conducted with 28% aqueous ammonia at 55° C. for 5 hours.

Purification of Synthesized Product

The synthetic oligonucleotide obtained as described above was dried into a dry product. The dry product was dissolved in 0.5 M $NaHCO_3/Na_2CO_3$ buffer (pH 9.0). The solution was subjected to gel filtration through "NAP-25 Column" (trade name, product of Pharmacia AB, Uppsala, Sweden), whereby unreacted substances were removed.

Labeling with Quencher Substance

The filtrate was dried into solid, and dissolved in sterilized water (150 μL) (oligonucleotide A solution). "Dabcyl-NHS" (trade name, product of Molecular Probes, Inc., OR, U.S.A.) (1 mg) was dissolved in DMF (dimethylformamide) (150 μL), and the oligonucleotide A solution and 1 M $NaHCO_3/Na_2CO_3$ buffer (150 μL) were added. The resulting mixture was stirred, followed by a reaction overnight at room temperature.

Purification of Synthesized Product

The reaction product was subjected to gel filtration through "NAP-25" (trade name, product of Pharmacia AB, Uppsala, Sweden) to remove unreacted substances. Then, the protecting group (MMT) on the 5' end was eliminated with 2% TFA. Reversed phase HPLC was conducting using "SEP-PAC $C_{18}$ column" to fractionate the target product in which the quencher substance, Dabcyl" was bound to the linker —$(CH_2)_7$—$NH_2$ of the oligonucleotide. The fractionated product was subjected to gel filtration through ""NAP-10" (trade name, product of Pharmacia AB, Uppsala, Sweden).

Labeling with Fluorescent Dye

The gel filtrate was dried into solid, and dissolved in sterilized water (150 μL) (oligonucleotide B solution). "Sulforhodamine 101 Acid Chloride" (trade name, product of Dojindo Laboratories, Kumamoto, Japan) (1 mg) was dissolved in DMF (100 μL), and the oligonucleotide B solution and 1 M $NaHCO_3/Na_2CO_3$ buffer (150 μL) were added. The resulting mixture was stirred, followed by a reaction overnight at room temperature to have the fluorescent dye, Texas Red, bound to the amino liner on the 5' end.

Purification of Synthesized Product

The reaction product was subjected to gel filtration through ""NAP-25" (trade name, product of Pharmacia AB, Uppsala, Sweden) to remove unreacted substances. Reversed phase HPLC was conducted in a similar manner as described above, and a nucleic acid probe according to the present invention, which was an oligonucleotide with the quencher substance bound to the $7^{th}$ thymine base from the 5' end and also with the fluorescent dye, Texas Red, added to the 5' end, namely, an nucleic acid probe labeled with the fluorescent dye and the quencher substance was obtained. Incidentally, the invention nucleic acid probe was eluted with a lag from the oligonucleotide with the quencher substance bound thereon.

Quantitation of the invention nucleic acid probe conducted by measuring a value at 260 nM with a spectrophotometer. With respect to the probe, scanning of an absorbance over 650 nm to 220 nm was also conducted using the spectrophotometer. As a result, absorptions ascribed to Dabcyl, Texas Red and DNA, respectively, were confirmed. Further, the purity of the purified product was tested by similar reversed phase HPLC as in the above. As a result, it was confirmed that the purified product gave a single peak.

The invention nucleic acid probe synthesized as described above is free of any base sequence having complementation at at least two positions between the base chains at positions where the probe was labeled with Texas Red as a fluorescent dye and Dabcyl as a quencher substance, respectively. The invention nucleic acid probe, therefore, does not form any double-stranded chain in its own chain. In other words, the invention nucleic acid probe does not form any stem-loop structure.

The above-described reversed phase chromatography was conducted under the following conditions:

Eluting solvent A: 0.05 N TEAA 5% $CH_3CN$
Eluting solvent B (for gradient elution): 0.05 N TEAA 40% $CH_3CN$
Column: "SEP-PAK C18" (trade name), 6×250 mm
Elution rate: 1.0 mL/min
Temperature: 40° C.
Detection: 254 nm

EXAMPLE 2

Synthesis of Target Nucleic Acid

An oligonucleotide the base sequence of which was (5')GGGGGGAAAAAAAAA(3') (SEQ ID NO: 1) was synthesized in a similar manner as in the synthesis of the above-described oligonucleotide, and provided as a target nucleic acid to which the present invention is applicable.

EXAMPLE 3

Figure 1:
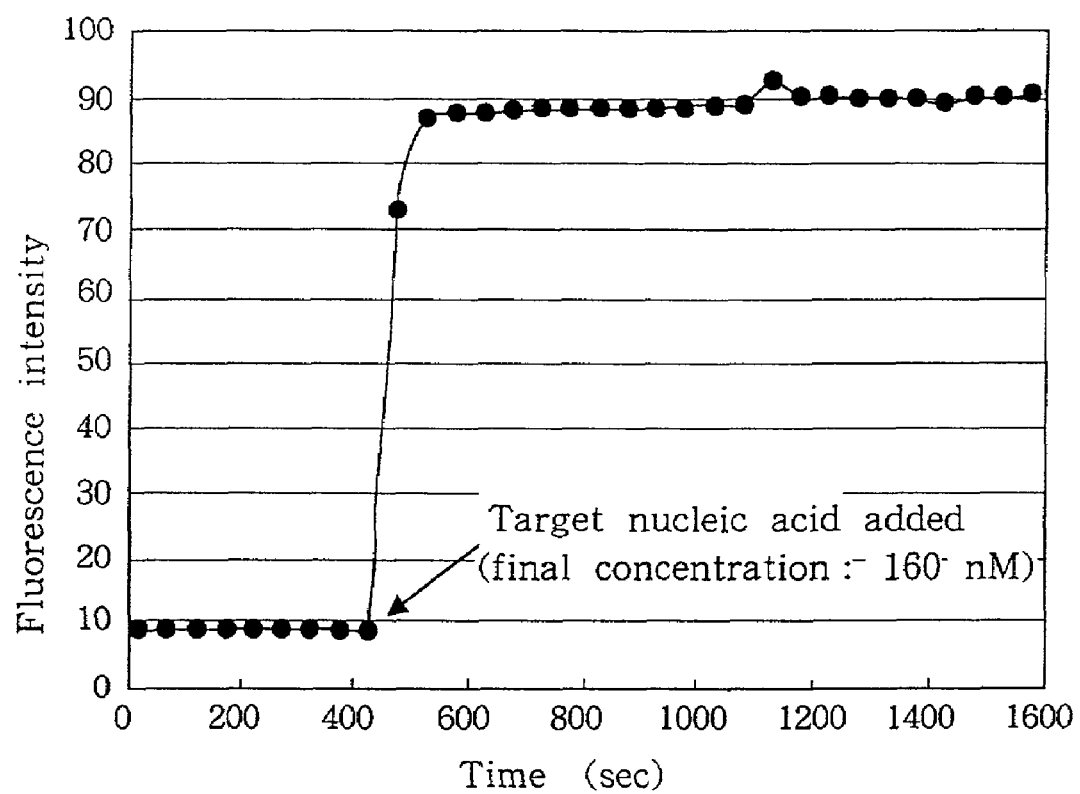
FIG. 1 diagrammatically shows changes in the intensity of fluorescence in a solution system with a nucleic acid probe according to the present invention contained therein when a target nucleic acid was added, in which time (sec) is plotted along the abscissa and intensities of fluorescence are plotted along the ordinate.

Measurement of the Intensity of Fluorescence from a Reaction System in which a Probe According to the Present Invention had been Hybridized with the Target Nucleic Acid Buffer (2 M NaCl, 200 mM Tris-HCl; pH 7.2) (500 µL) was added to a quartz cell (10 mm×10 mm) (capacity: 4 mL), followed by the addition of sterilized distilled water (1460 µL). The resulting mixture was then stirred. While maintaining the mixture at 35° C., the intensity of fluorescence was measured in the course of time [exciting wavelength: 581 nm (8 nm wide); wavelength of measuring fluorescence: 603 nm (8 nm wide)]. A target nucleic acid solution the concentration of which was 160 nM (32.0 µL) was then added, followed by stirring. The intensity of fluorescence was measured in the course of time under the same conditions as described above. The results are diagrammatically shown in FIG. 1. It is understood from the diagram that the addition of a target nucleic acid leads to an increase in the intensity of fluorescence and this increment is leveled off in an extremely short time, specifically in 100 seconds (1 minute and 40 seconds) [incidentally, about 15 minutes are required in the case of a molecule beacon: Nature Biotechnology, 14, 303-308 (1998)]. This indicates that the method of the present invention for the measurement of a nucleic acid can be performed in a short time.

EXAMPLE 4

Measurement of the Target Nucleic Acid

Figure 2:
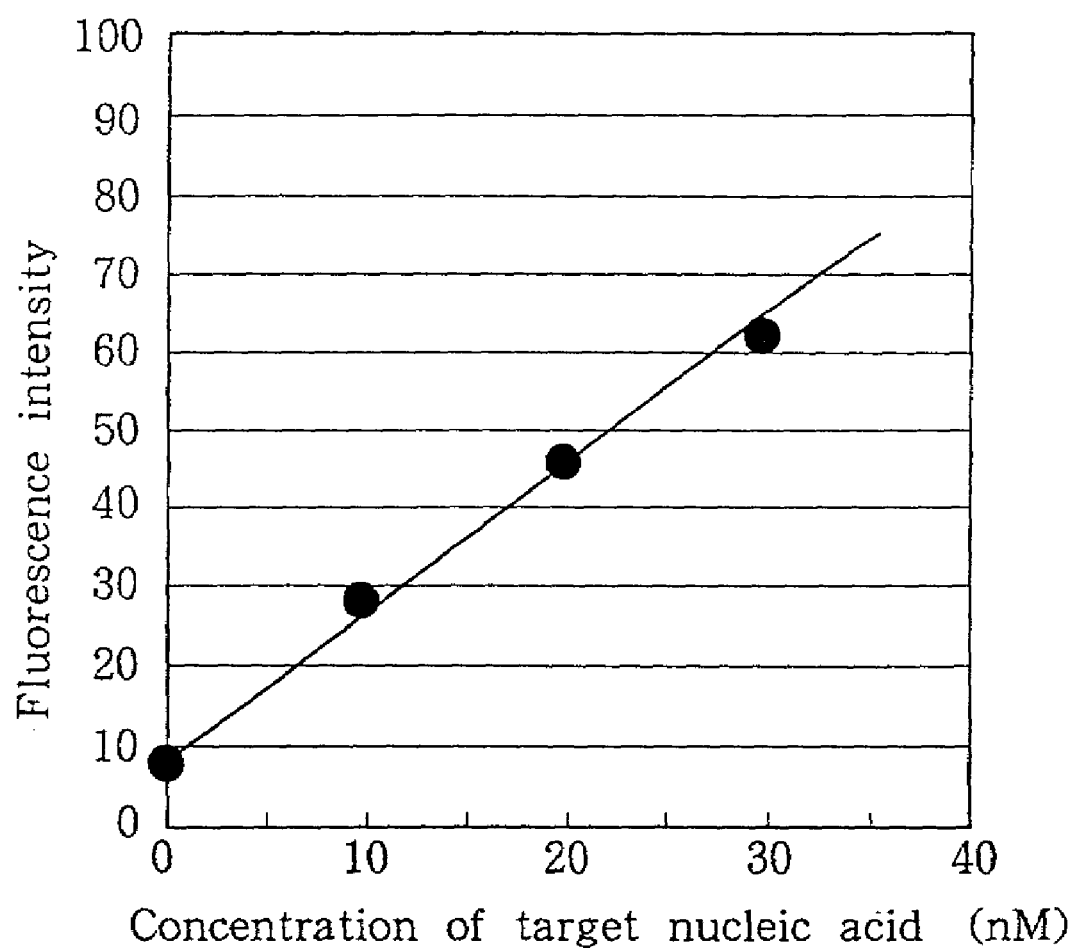
FIG. 2 shows a working curve for a target nucleic acid by a nucleic acid probe according to the present invention, in which concentrations of the target nucleic acid are plotted along the abscissa and intensities of fluorescence are plotted along the ordinate.

Under similar conditions as described above except that the concentration of the target nucleic acid were varied in various ways, the intensity of fluorescence was measured at the varied concentrations. The results are diagrammatically illustrated in FIG. 2. It has been found from the diagram that the intensity of fluorescence increases with the concentration of a target nucleic acid and their relationship is proportional.

From the foregoing results, it has been confirmed that the use of a nucleic acid probe according to the present invention permits measurement of a nucleic acid with good accuracy.

EXAMPLE 5

Effect of the Distance between a Fluorescent Dye and a Quencher Substance

Figure 3:
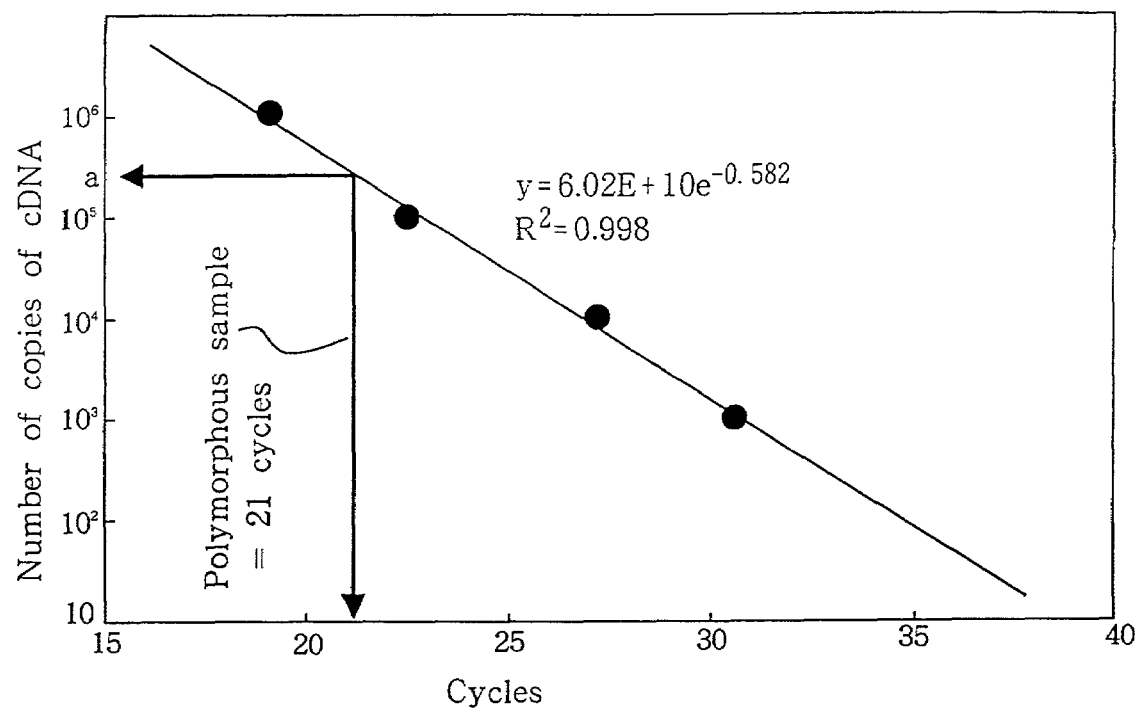
FIG. 3 illustrates probe designs and target nucleic acid designs for studying effects of the distance (the number of bases) between a fluorescent dye (Texas Red) and a quencher substance (Dabcyl) on the emission of fluorescence from a fluorescence emitting probe making use of interaction between the fluorescent dye and the quencher substance. In the top half of FIG. 3, the sequence (5'→3') is that of SEQ ID NO: 109. In the bottom half of FIG. 3, the sequence (5'→3') is that of SEQ ID NO: 110.

A deoxyribooligonucleotide the base sequence of which is shown in FIG. 3 was synthesized as in Example 1. In a similar manner as in Example 1, a probe was prepared by labeling a phosphate group at the 5' end of the deoxyribooligonucleotide with a fluorescent dye, Texas Red, and also by labeling an OH group on the C atom at the 6-position of the thymine base with a quencher substance, Dabcyl. The labeled thymine base was then shifted one base by one base toward the 3' end. In this manner, twenty (20) probes according to the present invention were synthesized. To those probes, complementary target deoxyribooligonucleotides were hybridized, respectively. Changes in the intensity of fluorescence through the hybridization were measured.

Tris buffer (2 M NaCl, 200 mM Tris-HCl; pH 7.2) (500 µL) was added to a quartz cell (the same cell as that used in Example 3), followed by the addition of sterilized distilled water (1460 µL). The resulting mixture was then stirred. A 10 µM solution of the probe according to the present invention (8.0 µL) was added to the mixture, followed by stirring (final concentration of the probe: 40 nM). While maintaining the mixture at 35° C., fluorescence was measured [exciting wavelength: 581 nm; wavelength of measuring fluorescence: 603 nm; slit width: 8 nm (both)]. As 10 µM solution of the target deoxyribooligonucleotide (32.0 µL) was then added, followed by stirring (final concentration of the target deoxyribooligonucleotide: 160 nM). Measurement of fluorescence was thereafter conducted in the course of time under the same conditions as described above.

Figure 4:
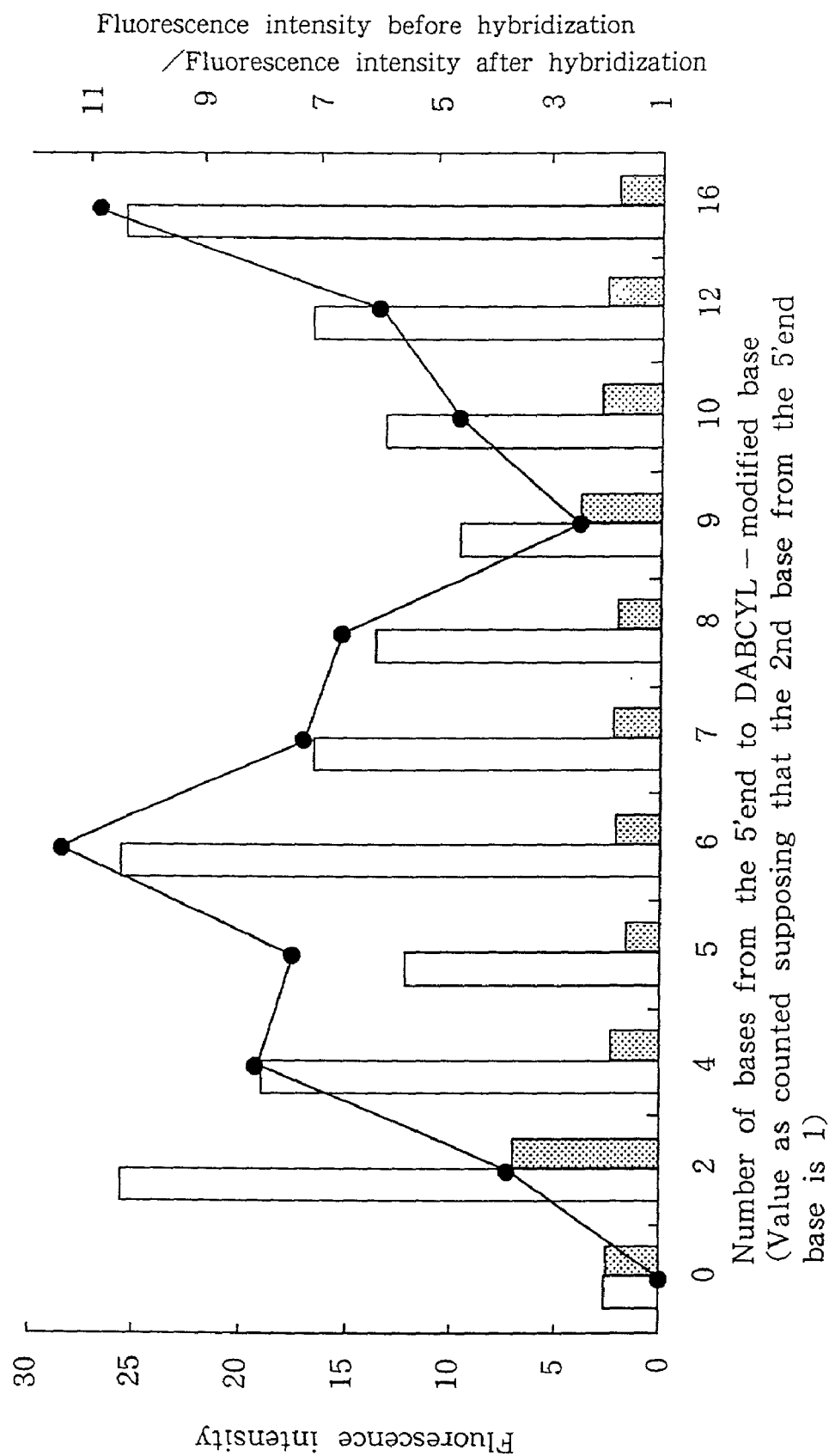

The results are diagrammatically shown in FIG. 4. As is appreciated readily from the diagram, it was observed that in most of the fluorescence emitting probes of the present invention dually modified by Dabcyl and Texas Red, hybridization with the target deoxyribooligonucleotide leads to an increase in the emission of fluorescence compared with the emission of fluorescence before the hybridization. Further, maximum emission of fluorescence was observed when the inter-base distance from the base having the phosphate group labeled with Texas Red to the Dabcyl-labeled base (when counted by assuming that the base number of the base labeled with Text Red was the $0^{th}$ base) was 6 bases long. The emission of fluorescence at that time was about 11 times higher compared with that before hybridization. When the inter-base distance was 16 bases long, large emission of fluorescence was also observed. The emission of fluorescence at that time was about 11 times as in the case of the 6 bases. As a DNA helix makes a turn with 10 bases, the $6^{th}$ and $16^{th}$ bases of a double-stranded DNA structure as observed from the 5' end base are located substantially on the opposite side of the helix. It is therefore considered that, when the $6^{th}$ and $16^{th}$ bases were labeled with the quencher substance, quenching of fluorescence took place based on transfer of electrons between Dabcyl and Texas Red when the deoxyribooligonucleotide is in the single-stranded form, but as a result of physical separation of Dabcyl and Texas Red from each other by the hybridization, the quenching of fluorescence based on the transfer of electrons was canceled and Texas Red emitted fluorescence.

EXAMPLE 6

Relationship between Fluorescent Dye and Intensity of Emitted Fluorescence

An investigation was conducted about the kinds of fluorescent dyes in fluorescent emitting probes according to the present invention. An experiment was carried out in a similar manner as in Example 5 except that the inter-base distance between each fluorescent dye and Dabcyl was set at 6 bases long and the width of a slit for fluorescence measurement was set at 5 nm in both excitation and measurement. The results are presented in Table 1.

An absorption of Dabcyl as a quencher appears at 400 to 500 nm. Many of probes with large emission of fluorescence, however, emitted fluorescence at wavelengths substantially shifted from the absorption of Dabcyl, that is, at wavelengths longer than 550 nm. In the case of a fluorescent dye which emits fluorescence at wavelengths longer than 550 nm, the mechanism of fluorescence quenching by Dabcyl is considered to be attributable primarily to transfer of photoexited electrons rather than FRET. Since Dabcyl and the fluorescent dye are physically separated from each other as a result of a change in the stereostructure of the double-stranded nucleic acids by hybridization, the fluorescence quenching phenomenon by the transfer of photoexcited electrons is cancelled. In the case of a fluorescent dye such as FITC which emits fluorescence at wavelengths close to the absorption of Dabcyl, it is considered that, even when Dabcyl and a fluorescent dye are physically separated as a result of a change in the stereostructure of the double-stranded nucleic acid and the fluorescence quenching phenomenon based on transfer of photoexcited electrons is hence cancelled, no substantial emission of fluorescence takes place from quenching of fluorescence by FRET because the quenching of fluorescence by FRET prevails. Accordingly, a dye capable of satisfying the following three conditions is desired as a fluorescent dye for use in a fluorescence emitting probe according to the present invention: (1) the fluorescence quenching phenomenon based on transfer of photoexcited electrons occurs between the fluorescent dye and Dabcyl; (2) Fluorescence of wavelengths substantially shifted from the absorption of Dabcyl is emitted; and (3) a strong interaction exists between the fluorescent dye and Dabcyl to reduce the intensity of fluorescence before hybridization (in other words, to further facilitate the occurrence of the fluorescence quenching phenomenon by transfer of photoexcited electrons).

TABLE 1

Relationship between Various Fluorescent Dyes and Intensity of Emitted Fluorescence

| Fluorescent dye | Exciting wavelength | Wavelength of fluorescence | Intensity of fluorescence before addition of target nucleic acid (A) | Intensity of fluorescence after addition of target nucleic acid (B) | A/B |
| --- | --- | --- | --- | --- | --- |
| FITC | 480 | 510 | 11.5 | 18.5 | 1.6 |
| TET | 500 | 530 | 36.8 | 48.0 | 1.3 |
| HEX | 520 | 540 | 3.9 | 7.4 | 1.9 |
| Cy3 | 540 | 560 | 2.0 | 7.4 | 3.7 |
| Bodipy 581/591 | 555 | 582 | 1.6 | 6.4 | 4.0 |
| Alexa531 | 500 | 539 | 7.3 | 26.0 | 3.6 |
| 6-ROX | 560 | 590 | 4.8 | 18.9 | 3.9 |
| Alexa594 | 575 | 603 | 2.2 | 15.22 | 6.9 |
| Bodipy TR | 585 | 615 | 2.4 | 9.6 | 4.0 |
| Texas Red | 585 | 603 | 2.1 | 21 | 10 |

EXAMPLE 7

Probe with Intra-Chain Bases Modified by Fluorescent Dye and Quencher

A probe with intra-chain bases modified by a fluorescent dye and a quencher and a target deoxyribooligonucleotide, such as those shown in FIG. 5, were synthesized in a similar manner as in Example 1 with the following exceptions: (1) using "Amino-Modifier C6 dT" (product of Glen Research Corporation, VA, U.S.A) in place of "5' Amino-Modider Cy Kit" (product of Glen Research Corporation, VA, U.S.A), the probe was modified with Texas Red; (2) Dabcyl was introduced directly into the base chain by using "Dabcyl dT" (product of Glen Research Corporation, VA, U.S.A) instead of modifying the probe with Dabcyl by means of "5' Amino-Modifier C6 Kit" (product of Glen Research Corporation, VA, U.S.A); and (3) the Dabcyl-modification step and the subsequent purification step were omitted accordingly.

An investigation was then conducted in a similar manner as in Example 5 to determine whether or not the probe so obtained would be actually usable. A further investigation was also made for possible effects of the distance between the bases labeled with the quencher (Dabcyl) and the fluorescent dye (Texas Red), respectively. The results are diagrammatically illustrated in FIG. 6. As is evident from the results, it has been found that even a probe with intra-chain bases modified with a fluorescent dye and a quencher, respectively, is actually usable. Like the probe with the 5' end phosphate group modified with Texas Red, maximum emission of fluorescence was observed when the inter-base distance between Texas Red and Dabcyl was 6 bases long or 16 bases long. The intensity of fluorescence emitted at that time was about 10 times higher compared with the fluorescence intensity before the hybridization.

Examples 8-31 and Comparative Example 1 relate to fluorescence quenching probes according to the present invention.

EXAMPLE 8

Preparation of a nucleic acid probe to be hybridized to the nucleic acid base sequence 16S rRNA of *Escherichia coli*, namely, having the base sequence of (3')CCGCTCACGC ATC(5') (SEQ ID NO: 111) was conducted as will be described hereinafter.

Preparation of Nucleic Acid Probe

A deoxynucleotide, which had the base sequence of (3')CCGCTCACGC ATC(5') (SEQ ID NO: 111) and contained —$(CH_2)_7$—$NH_2$ bonded to the OH group on the carbon atom at the 3' position of deoxyribose at the 3' end of the oligodeoxyribonucleotide, was purchased from Midland Certified Reagent Company, TX, U.S.A. From Molecular Probes, Inc., "FluoReporter Kit F-6082" (trade name) was also purchased, which contained not only "BODIPY FL" propionic acid succinimidyl ester but also a reagent for conjugating the compound to the amine derivative of the oligonucleotide. The kit was caused to act on the above-purchased oligonucleotide, whereby a nucleic acid probe labeled with "BODIPY FL" was synthesized for use in this Example.

Purification of Synthesized Product

The synthesized product was dried into a dry product. The dry product was dissolved in 0.5 M $NaHCO/Na_2CO_3$ buffer (pH 9.0). The solution was subjected to gel filtration through "NAP-25 Column" (trade name, product of Pharmacia AB, Uppsala, Sweden), whereby unreacted substances were removed. Further, reversed phase HPLC (B gradient: 15 to 65%, 25 minutes) was conducted under the below-described conditions. An eluted main fraction was collected. The collected fraction was lyophilized, whereby a nucleic acid probe was obtained with a yield of 23% as calculated relative to 2 mM of the starting oligonucleotide.

The above-described reversed phase chromatography was conducted under the following conditions:
Eluting solvent A: 0.05 N TEAA 5% $CH_3CN$
Eluting solvent B (for gradient elution): 0.05 N TEAA 40% $CH_3CN$
Column : "CAPCEL PAK C18" (trade name), 6×250 mm
Elution rate: 1.0 mL/min
Temperature: 40° C.
Detection: 254 nm

EXAMPLE 9

Using a 200-mL Erlenmeyer flask which had been sterilized and which contained sterilized nutrient broth (NB) (50 mL; product of Difco; composition: NB, 0.08 g/100 mL), *Escherichia coli* JM109 was cultured overnight at 37° C. under shaking. To the culture, an equivalent amount of 99.7% ethanol was then added. A 2-mL aliquot of the ethanol-added culture was centrifuged in a 2.0-mL Eppendorf centrifuge tube, whereby cells were obtained. The cells were washed once with 30 mM phosphate buffer (sodium salt) (100 µL; pH 7.2). The cells were suspended in the phosphate buffer (100 µL) which contained 130 mM NaCl. The suspension was ultrasonicated for 40 minutes under ice cooling (output: 33 W, oscillating frequency: 20 kHz, oscillation method: 0.5-second oscillation, followed by a 0.5-second pause), whereby a homogenate was prepared.

After the homogenate was centrifuged, the supernatant was collected and was then transferred into a cell of a fluorimeter. The cell with the supernatant placed therein was controlled at 36° C. A solution of the above-described nucleic acid probe, said solution having had been controlled to 36° C. beforehand, was added to the supernatant to give a final concentration of 5 nM. While controlling at 36° C., *E. coli* 16S rRNA and the nucleic acid probe were hybridized for 90 minutes. Intensity of fluorescence emission from the fluorescent dye was then measured by the fluorimeter.

As the intensity of fluorescence emission from the fluorescent dye before the hybridization, a value measured by using 30 mM phosphate buffer (sodium salt), which contained 130 mM NaCl, (pH: 7.2) instead of the above-described supernatant was adopted. Intensity of fluorescence emission was measured by changing the ratio of the amount of the nucleic probe to the amount of the supernatant (exciting light: 503 nm; measured fluorescence color: 512 nm). The results are shown in FIG. 7. As is appreciated from FIG. 7, the intensity of fluorescence emission from the fluorescent dye decreased as the ratio of the amount of the supernatant increased. Namely, it is understood that in the present invention, the magnitude of a decrease in fluorescence emission from a fluorescent dye becomes greater in proportion to the amount of a target nucleic acid to which a nucleic acid probe hybridizes.

EXAMPLE 10

Preparation of Nucleic Acid Probe

An oligonucleotide, which was to be hybridized to 23S rRNA of *Escherichia coli* JM109, had a base sequence of (5')CCCACATCGTTTTGTCTGGG(3') (SEQ ID NO: 4) and contained —$(CH_2)_7$—$NH_2$ bonded to the OH group on the carbon atom at the 3' position of the 5' end nucleotide of the oligonucleotide, was purchased from Midland Certified Reagent Company, U.S.A. as in Example 8. From Molecular Probes, Inc., "FluoReporter Kit F-6082" (trade name) was also purchased as in Example 8, which contained not only "BODIPY FL" propionic acid succinimidyl ester but also a reagent for conjugating the compound to the amine derivative of the oligonucleotide. The kit was caused to act on the above-purchased oligonucleotide, whereby a nucleic acid probe labeled with "BODIPY FL" was synthesized. The synthesized product so obtained was purified as in Example 8, whereby the nucleic acid probe labeled with "BODIPY FL" was obtained with a yield of 25% as calculated relative to 2 mM of the starting oligonucleotide.

EXAMPLE 11

With *Escherichia coli* JM109 cells obtained in Example 9, cells of *Pseudomonas paucimobilis* (now called "*Sphingomonas paucimobilis*) 421Y (FERM P-5122), said cells having have been obtained using the same culture medium and cultivation conditions as in Example 9, were mixed at the same concentration as *Escherichia coli* JM109 in terms of OD660 value, whereby a co-cultivation system of the microorganisms was prepared. From the resulting mixed system in which the cell concentration of *Escherichia coli* JM109 was the same as that in Example 9, a homogenate was prepared in the same manner as in Example 9. An experiment was conducted in a similar manner as in Example 9 except that the nucleic acid probe prepared in Example 10 was used, 543 nm exciting light was used, and 569 nm fluorescence was measured. The results were similar to those obtained in Example 9.

EXAMPLE 12

The base selectivity of a target nucleic acid in the quenching phenomenon fluorescence, that is, the base selectivity according to the present invention was investigated. Ten kinds of synthetic target deoxyribooligonucleotides (30 mer; poly a to poly j), which will be described subsequently herein, were prepared by a DNA synthesizer, "ABI 394" (trade name; manufactured by Perkin-Elmer Corp.)

Also prepared were the below-described probes according to the present invention, which were labeled with "BODIPY FL" at the 5' ends of deoxyribooligonucleotides corresponding to the above-described synthetic deoxyribooligonucleotides (target genes or target nucleic acids), respectively.

Primer deoxyribooligonucleotides, which corresponded to the above-described synthetic deoxyribooligonucleotides and contained —$(CH_2)_6$—$NH_2$ bonded to the phosphate groups at the 5' ends of the primer deoxyribooligonucleotides, were purchased from Midland Certified Reagent Company. From Molecular Probes, Inc., "FluoroReporter Kit F-6082" (trade name) was also purchased, which contained not only "BODIPY FL" propionic acid succinimidyl ester but also a reagent for conjugating the compound to the amine derivative of the deoxyribooligonucleotide. The kit was caused to act on the above-purchased primer deoxyribooligonucleotides, whereby invention nucleic acid probes labeled with "BODIPY FL" (probes a, b, c, d, f, g, h) were synthesized. An investigation was made under the below-described conditions to determine how much the fluorescence emission from the fluorescent dye would decrease when the probes were caused to hybridize to their corresponding synthetic deoxyribooligonucleotides, and the specificity of the invention probes was studied. Fundamentally, purification was conducted in a similar manner as in Example 8.

| Name | Target deoxyribooligonucleotide |
|---|---|
| poly a | 5'ATATATATTTTTTTGTTTTTTTTTTTT3' (SEQ ID NO: 5) |
| poly b | 5'ATATATATTTTTTTGTTTTTTTTTTTT3' (SEQ ID NO: 6) |
| poly c | 5'ATATATATTTTTTTTGTTTTTTTTTTTT3' (SEQ ID NO: 7) |
| poly d | 5'ATATATATTTTTTTTTGTTTTTTTTTTT3' (SEQ ID NO: 8) |
| poly e | 5'ATATATATTTTTTTTTTGTTTTTTTTTT3' (SEQ ID NO: 112) |
| poly f | 5'ATATATATTTTTTCTTTTTTTTTTTT3' (SEQ ID NO: 9) |
| poly g | 5'ATATATATTTTTTTCTTTTTTTTTTTT3' (SEQ ID NO: 10) |
| poly h | 5'ATATATATTTTTTTTCTTTTTTTTTTT3' (SEQ ID NO: 11) |
| poly i | 5'ATATATATTTTTTTTTCTTTTTTTTTT3' (SEQ ID NO: 12) |
| poly j | 5'ATATATATTTTTTTTTTCTTTTTTTTT3' (SEQ ID NO: 13) |

| Name | Invention probe |
|---|---|
| Probe a | 3'TATATATAAAAAAACAA5'-BODIPY FL/C6 (SEQ ID NO: 14) |
| Probe b | 3'TATATATAAAAAAAACA5'-BODIPY FL/C6 (SEQ ID NO: 15) |
| Probe c | 3'TATATATAAAAAAAAAC5'-BODIPY FL/C6 (SEQ ID NO: 16) |
| Probe d | 3'TATATATAAAAAAAAAA5'-BODIPY FL/C6 (SEQ ID NO: 17) |
| Probe f | 3'TATATATAAAAAAAGAA5'-BODIPY FL/C6 (SEQ ID NO: 18) |
| Probe g | 3'TATATATAAAAAAAAGA5'-BODTPY FL/C6 (SEQ ID NO: 19) |
| Probe h | 3'TATATATAAAAAAAAAG5'-BODIPY FL/C6 (SEQ ID NO: 20) |

(1) Components of hybridization mixture

| | |
|---|---|
| Synthetic DNA | 320 nM (final concentration) |
| Nucleic acid probe | 80 nM (final concentration) |
| NaCl | 50 nM (final concentration) |
| $MgCl_2$ | 1 nM (final concentration) |
| Tris-HCl buffer (pH 7.2) | 100 nM (final concentration) |
| "MiliQ" purified water | 1.6992 mL |
| Final whole volume | 2.0000 mL |

(2) Hybridization temperature: 51° C.

(3) Measuring conditions

| | |
|---|---|
| Exciting light: | 503 nm |
| Measured fluorescence color: | 512 nm |

TABLE 2

| Nucleic acid probe | Target nucleic acid | Decrease in Fluorescence intensity (%) |
|---|---|---|
| a | a | −10 |
| b | b | 2 |
| c | c | 75 |
| d | d | 48 |
| d | e | 18 |
| f | f | −8 |
| g | g | −2 |
| h | h | 70 |
| d | I | −6 |
| d | j | −5 |

The results are shown in Table 2. As is appreciated from Table 2, it is preferred to design the base sequence of a nucleic acid probe labeled with a fluorescent dye such that, when the nucleic acid probe hybridizes to a target DNA (deoxyribooligonucleotide), at least one G (guanine) base exists in the base sequence of the target DNA at a position 1 to 3 bases apart from an end base portion where the probe and the target DNA are hybridized with each other. From Table 2, it is also understood to be desired to design the base sequence of a nucleic acid probe labeled with a fluorescent dye such that, when the nucleic acid probe is hybridized with a target DNA, base pairs in the nucleic acid hybrid complex form at least one G (guanine) and C (cytosine) pair at the end portion.

EXAMPLE 13

Target nucleic acids and invention nucleic acid probes of the below-described base sequences were prepared. In a similar manner as in the preceding Example, an investigation was made about effects of the number of G(s) in each target nucleic acid and the number of G(s) in its corresponding invention nucleic acid probe.

| Name | Target deoxyribooligonucleotide |
|---|---|
| poly k | 5'TATATATATATTTTTGGGGG3' (SEQ ID NO: 21) |
| poly l | 5'TATATATATATTTTTGGGG3' (SEQ ID NO: 22) |
| poly m | 5'TATATATATTTTTTTGGG3' (SEQ ID NO: 23) |
| poly n | 5'TATATATATTTTTTTTGG3' (SEQ ID NO: 24) |
| poly o | 5'TATATATATTTTTTTTTG3' (SEQ ID NO: 25) |
| poly p | 5'TATATATATATTTTTCCCCC3' (SEQ ID NO: 26) |
| poly q | 5'TATATATATATTTTTCCCC3' (SEQ ID NO: 27) |
| poly r | 5'TATATATATTTTTTTCCC3' (SEQ ID NO: 28) |
| poly s | 5'TATATATATTTTTTTTCC3' (SEQ ID NO: 29) |
| poly t | 5'TATATATATTTTTTTTTC3' (SEQ ID NO: 30) |
| poly u | 5'TATATATATTTTTTTTTT3' (SEQ ID NO: 31) |

| Name | Invention probe |
|---|---|
| probe k | 3'ATATATATATAAAAACCCCC5'-BODIPY FL/C6 (SEQ ID NO: 31) |
| probe l | 3'ATATATATATAAAAACCCC5'-BODIPY FL/C6 (SEQ ID NO: 32) |
| probe m | 3'ATATATATATAAAAAACCC5'-BODIPY FL/C6 (SEQ ID NO: 33) |
| probe n | 3'ATATATATATAAAAAAACC5'-BODIPY FL/C6 (SEQ ID NO: 34) |
| probe o | 3'ATATATATATAAAAAAAAC5'-BODIPY FL/C6 (SEQ ID NO: 35) |
| probe p | 3'ATATATATATAAAAAGGGGG5'-BODIPY FL/C6 (SEQ ID NO: 36) |
| probe q | 3'ATATATATATAAAAAAGGGG5'-BODIPY FL/C6 (SEQ ID NO: 37) |
| probe r | 3'ATATATATATAAAAAAAGGG5'-BODIPY FL/C6 (SEQ ID NO: 38) |
| probe s | 3'ATATATATATAAAAAAAAGG5'-BODIPY FL/C6 (SEQ ID NO: 39) |
| probe t | 3'ATATATATATAAAAAAAAAG5'-BODIPY FL/C6 (SEQ ID NO: 40) |
| probe u | 3'ATATATATATAAAAAAAAAA5'-BODIPY FL/C6 (SEQ ID NO: 41) |

TABLE 3

| Nucleic acid probe | Target nucleic acid | Decrease in Fluorescence intensity (%) |
|---|---|---|
| k | k | 93 |
| l | l | 92 |
| m | m | 94 |
| n | n | 92 |
| o | o | 87 |
| p | p | 61 |
| q | q | 68 |
| r | r | 69 |
| s | s | 75 |
| t | t | 73 |
| u | u | 2 |

As is appreciated from Table 3, neither the number of G(s) in a target nucleic acid nor the number of G(s) in an invention probe substantially affects a decrease in fluorescence intensity.

EXAMPLE 14

Target nucleic acids and invention nucleic acid probes of the below-described base sequences were prepared in a similar manner as described above. The invention nucleic acid probes in this Example were each labeled at the 5' end portion of oligonucleotide with "BODIPY FL/C6". In a similar manner as in the preceding Example, an investigation was made about effects of the kind or bases in each target nucleic acid and the kind of bases in its corresponding invention nucleic acid probe.

| Name | Target deoxyribooligonucleotide |
|---|---|
| poly W | 5'CCCCCCTTTTTTTTTTTT3' (SEQ ID NO: 43) |
| poly X | 5'GGGGGGAAAAAAAAAAAA3' (SEQ ID NO: 44) |
| poly Y | 5'TTTTTTCCCCCCCCCCCC3' (SEQ ID NO: 45) |
| poly Z | 5'AAAAAAGGGGGGGGGGGG3' (SEQ ID NO: 46) |

| Name | Invention probe |
|---|---|
| probe w | BODIPY FL/C6-5'AAAAAAAAGGGGGG3' (SEQ ID NO: 47) |
| probe x | BODIPY FL/C6-5'TTTTTTTTTCCCCCC3' (SEQ ID NO: 48) |
| probe y | BODIPY FL/C6-5'GGGGGGGGGAAAAAA3' (SEQ ID NO: 49) |
| probe z | BODIPY FL/C6-5'CCCCCCCCCTTTTTT3' (SEQ ID NO: 50) |

TABLE 4

| Nucleic acid probe | Target nucleic acid | Fluorescence intensity from probe alone (A) | Fluorescence intensity after addition of target nucleic acid (B) | Decrease in fluorescence intensity, % (C)* |
|---|---|---|---|---|
| W | w | 330 | 380 | −15 |
| X | x | 440 | 430 | 2 |
| Y | y | 40 | 50 | 25 |
| Z | z | 360 | 30 | 92 |

*Decrease in fluorescence intensity, % (C) = {(A − B)/A} × 100

As is appreciated from Table 4 and the preceding Example, a substantial decrease takes place in fluorescence intensity (i) when an end of an invention probe labeled with a fluorescent dye is composed of C and hybridization of a target nucleic acid forms a G-C pair, or (ii) when an end of an invention probe labeled with a fluorescent dye is composed of a base other than C and at least one G exists on a side closer to the 3' end of a target nucleic acid than a base pair formed of a base at a location where the invention probe is labeled with the fluorescent dye and a base of the target nucleic acid.

EXAMPLE 15

Concerning the kinds of dyes usable for labeling nucleic acid probes of the present invention, an investigation was made in a similar manner as in the preceding Examples. As an invention probe, the probe z of Example 14 was used. As a target nucleic acid, on the other hand, the oligonucleotide z of Example 14 was employed.

The results are shown in Table 5. As is readily envisaged from this table, illustrative fluorescent dyes suitable for use in the present invention can include FITC, "BODIPY FL", "BODIPY FL/C3", "BODIPY FC/C6", 6-joe, and TMR.

TABLE 5

| Fluorescent dye | Decrease in fluorescence intensity (%) |
|---|---|
| FITC | 90 |
| "BODIPY FL" | 95 |
| "BODIPY FL/C3" | 98 |
| "BODIPY FL/C6" | 97 |
| 6-joe | 75 |
| TMR | 93 |

Incidentally, the decreases (%) in fluorescence intensity were calculated in a similar manner as in Example 14.

EXAMPLE 16

Experiment on Effects of Heat Treatment of Target Nucleic Acid (16S rRNA)

Preparation of Invention Nucleic Acid Probe

An oligonucleotide was purchased from Midland Certified Reagent Company, U.S.A. as in Example 8. The oligonucleotide had a base sequence of (5')CATCCCCACC TTCCT CCGAG TTGACCCCGG CAGTC(3') (35 base pairs; SEQ ID NO: 51) hybridizable specifically to the 16S rRNA base sequence of KYM-7 strain, said base sequence being equivalent to the base sequence ranging from the 1156$^{th}$ base to the 1190$^{th}$ base of the 16S rRNA of *Escherichia coli* JM109, contained deoxyribonucleotides at the 1$^{st}$ to 16$^{th}$ bases and the 25$^{th}$ to 35$^{th}$ bases, respectively, and a methyl-modified ribooligonucleotide at the 17$^{th}$ to 24$^{th}$ bases, said methyl-modified ribooligonucleotide being modified with a methyl group (modified with an ether bond) at the OH group on the carbon atom at the 2' position, and was modified with —(CH$_2$)$_7$—NH$_2$ at the OH group of the phosphate group at the 5' end. On the other hand, 2-O-Me-oligonucleotide for use in the 2-O-Me probe (a probe formed of a 2-O-Me-oligonucleotide will be simply called "2-O-Me probe") was obtained from GENSET SA, Paris, France by relying upon their custom DNA synthesis services.

From Molecular Probes, Inc., "FluoroReporter Kit F-6082" (trade name) was also purchased, which contained not only "BODIPY FL/C6" propionic acid succinimidyl ester but also a reagent for conjugating the compound to the amine derivative of the oligonucleotide. The kit was caused to act on the above oligonucleotide, whereby a nucleic acid probe labeled with "BODIPY FL/C6" was synthesized. The synthesized product so obtained was purified as in Example 8, whereby the nucleic acid probe according to the present invention labeled with "BODIPY FL/C6" was obtained with a yield of 23% as calculated relative to 2 mM of the starting oligonucleotide. This probe was named "35-nucleotides-chained 2-O-Me probe".

Using a DNA synthesizer, an oligoribonucleotide having a base sequence of (5')TCCTTTGAGT TCCCGGCCGG(3') (SEQ ID NO: 52) A was synthesized as in the above to provide it as a forward-type hepter probe. On the other hand, an oligoriboxynucleotide having a base sequence of (5') CCCTGGTCGT AAGGGCCATG ATGACTTGAC GT (3') (SEQ ID NO: 53) was synthesized by using a DNA synthesizer, in a similar manner as described above to provide it as a backward-type, in other words, reverse-type helper probe.

The 35-nucleotides-chained 2-O-Me probe, the forward-type helper probe and the reverse-type helper probe were dissolved in buffer of the below-described composition such that their concentrations reached 25 nM, respectively, and the solution so obtained was heated at 75° C. (probe solution).

The above-described 16S rRNA was subjected to heat treatment at 95° C. for 5 minutes, and was then added to the probe solution which had been maintained under the below-described reaction conditions. By a fluorescence measuring instrument "Perkin-Elmer LS-50B" (trade name), the intensity of fluorescence was measured. The results are shown in FIG. 8. Incidentally, data obtained by using 16S rRNA which was not subjected to the above-described heat treatment are plotted as a control. It is understood from FIG. 8 that substantial decreases in fluorescence intensity took place in the experimental group subjected to heat treatment. These results indicate that heat treatment of 16S rRNA at 95° C. induces stronger hybridization with the probe according to the present invention.

Reaction Conditions:

| | |
|---|---|
| 16S rRNA: | 10.0 nm |
| Probe: | 25 nM, each |
| Buffer: | 100 mM succinic acid, 125 mM lithilim hydroxide, 8.5% lithium dodecylsulfite, pH 5.1 |
| Temperature: | 75° C. |

EXAMPLE 17

Experiment on Contribution of 2'-O-Me-Oligonucleotide and Helper Probe to the Efficiency of Hybridization Various invention probes and helper probes, which were to be hybridized to the above-described 16S rRNA, were prepared in a similar manner as in Example 16. The 2-O-Me-oligonucleotides for use in 2-O-Me probes were all obtained by ordering their synthesis to GENSET SA, Paris, France. Under conditions to be described subsequently herein, an investigation was made about effects of the 2'-O-Me probes of the present invention, effects of the lengths of nucleotide chains in the probes and effects of helper probes in the experiment groups of diagrams A, B, C and D in FIG. 9 in a similar manner as in Example 16. The results are presented in FIG. 9.

It is appreciated from these diagrams that the 2-O-Me probes according to the present invention contribute to the efficiency of hybridization. It is also understood that these helper probes are effective in increasing the efficiency of hybridization when the base strands of the 2-O-Me probes are short.

1) 35-Nucleotides-chained 2-O-Me probe: Same probe as in Example 16.

2) 35-Nucleotides-chained DNA probe: A probe having the same base sequence as the 35-nucleotides-chained 2-O-Me probe described above under 1) except that the oligonucleotide is formed of a deoxyribose.

3) 17-Nucleotides-chained 2-O-Me probe: A probe having the same base sequence as the 35-nucleotides chained 2-O-Me probe described above under 1) except that the nucleotides ranging over 8 bases from the 5' end and 10 bases from the 3' end were removed.

4) 17-Nucleotides-chained DNA probe: A probe having the same base sequence as the 33-nucleotides-chained DNA probe described above under 2) except that a nucleotide ranging over 16 bases from the 3' end was removed.

5) Forward-type 2-O-Me-helper probe: A helper probe obtained by modifying (via an ether bond) the OH group on the carbon atom at the 2'-position of ribose over the central 8 bases (the $9^{th}$ base to the $16^{th}$ base counted from the 5' end) of the forward-type helper probe in Example 16 with a methyl group.

6) Reverse-type 2-O-Me-helper probe: A helper probe obtained by modifying (via an ether bond) the OH group on the carbon atom at the 2'-position of ribose over the central 8 bases (the $9^{th}$ base to the $16^{th}$ base counted from the 5' end) of the reverse-type helper probe in Example 16 with a methyl group.

7) Forward-type DNA helper probe: A helper probe having the same base sequence as the forward-type helper probe in Example 16 except that the oligonucleotide is formed of a deoxyribonucleotide.

8) Reverse-type DNA helper probe: A helper probe having the same base sequence as the reverse-type helper probe in Example 16 except that the oligonucleotide is formed of a deoxyribonucleotide.

9) 35-Base oligoribonucleotide: An oligoribonucleotide having a base sequence of (5')CATCCCCACC TTCCTCCGAG TTGACCCCGG CAGTC(3') (SEQ ID NO: 54).

10) 17-Base oligoribonucleotide: An oligoribonucleotide having a base sequence of (5')CCTTCCTCCG AGTTGAC (3') (SEQ ID NO: 55).

Reaction Conditions:

| | |
|---|---|
| Concentration of 16S rRNA: | 10 nM |
| Concentration of probe: | 25 nM |
| Helper probe concentration: | 1 µM |
| Buffer composition: | 100 mN succinic acid, 125 mM lithium hydroxide, 8.5% lithium dodecyl-sulfite, pH 5.1 |

Reaction Temperature:
75° C. (for 35-nucleotides-chained 2-O-Me probe)
70° C. (for 17-nucleotides-chained 2-O-Me probe)
75° C. (for 33-nucleotides-chained DNA probe)
60° C. (for 17-nucleotides-chained oligoribonucleotide probe)

Experiment System, FIG. 9A:
HP(M)⁺: 16S rRNA, 35-nucleotides-chained DNA probe, forward-type 2-O-Me helper probe, reverse-type 2-O-Me helper probe,
HP(D)⁺: 16S rRNA, 35-nucleotides-chained DNA probe, forward-type DNA helper probe, reverse-type DNA probe,
HP−: 16S rRNA, 35-nucleotides-chained DNA probe, and
Ref (Control): 35-nucleotides-chained DNA oligoribonucleotide, 35-nucleotides-chain.

Experiment System, FIG. 9B:
HP(M)⁺: 16S rRNA, 35-nucleotides-chained 2-O-Me probe, forward-type 2-O-Me helper probe, reverse-type 2-O-Me helper probe,
HP(D)⁺: 16S rRNA, 35-nucleotides-chained 2-O-Me probe, forward-type DNA helper probe, reverse-type DNA probe,
HP−: 16S rRNA, 35-nucleotides-chained 2-O-Me probe, and
Ref (Control): 35-nucleotides-chained DNA oligoribonucleotide, 35-nucleotides-chained 2-O-Me probe.

Experiment System, FIG. 9C:
HP+(M): 16S rRNA, 17-nucleotides-chained DNA probe, forward-type 2-O-Me helper probe, reverse-type 2-O-Me helper probe,
HP+(D): 16S rRNA, 17-nucleotides-chained DNA probe, forward-type DNA helper probe, reverse-type DNA probe,
HP−: 16S rRNA, 17-nucleotides-chained DNA probe, and
Ref (Control): 17-nucleotides-chained DNA oligoribonucleotide, 17-nucleotides-chain.

Experiment System, FIG. 9D:
HP+(M): 16S rRNA, 17-nucleotides-chained 2-O-Me probe, forward-type 2-O-Me helper probe, reverse-type 2-O-Me helper probe, HP+(D): 16S rRNA, 17-nucleotides-chained 2-O-Me probe, forward-type DNA helper probe, reverse-type DNA probe, HP−: 16S rRNA, 17-nucleotides-chained 2-O-Me probe, and Ref (Control): 17-nucleotides-chained DNA oligoribonucleotide, 17-nucleotides-chained 2-O-Me probe.

EXAMPLE 18

Preparation of Working Curve for rRNA Determination

At diverse concentrations within a range of from 0.1 to 10 nM, the above-described rRNA was heated at 95° C. for 5 minutes. The resulting nucleic acid solutions were added to aliquots of a reaction mixture, respectively. The reaction mixture had been prepared and maintained under the below-described reaction conditions. Upon elapsed time of 1,000 seconds, decreases in fluorescence intensity were measured using "Perkin-Elmer LS-50B". The results are plotted in FIG. 10. It is appreciated from the diagram that the working curve shows linearity in the range of from 0.1 to 10 nM. Incidentally, the following 35-nucleotides-chained 2-O-Me probe was the same probe as that prepared in Example 16.

Reaction Conditions:

| | |
|---|---|
| Concentrations of 35-nucleotides-chained 2-O—Me probe: | 1.0 to 25 nM |
| Buffer composition: | 100 mM succinic acid, 125 mM lithium hydroxide, 8.5% lithium dodecyl-sulfite, pH 5.1 |
| Reaction temperature: | 75° C. |

EXAMPLE 19

FISH Method

In a similar manner as described above, the below-described 35- and 36-nucleotides-chained oligodeoxyribonucleotide 2-O-Me probes according to the present invention were prepared for hybridization to the respective rRNAs of *Cellulomonas* sp. KYM-7 (FERM P-11339) and *Agrobacterium* sp. KYM-8 (FERM P-16806), respectively. Those probes had the following base sequences:

35-nucleotides-chained oligodeoxyribonucleotide 2-O-Me probe for assaying the rRNA of *Cellulomonas* sp. KYM-7:

(5')CATCCCCACC TTCCTCCGAGTTGACCCGG CAGTC(3') (SEQ ID NO: 56) (the underlined portion is modified with a methyl group)

36-nucleotides-chained oligodeoxyribonucleotide 2-O-Me probe for assaying the rRNA of *Agrobacterium* sp. KYM-8:

(5') CATCCCCACC TTCCTCTCGGCTTATCACCG GCAGTC (3') (SEQ ID NO: 57) (the underlined portion is modified with a methyl group)

*Cellulomonas* sp. KYM-7 and *Agrobacterium* sp. KYM-8 were co-cultured on a culture medium of the below-described composition under the below-described cultivation conditions. Co-cultures were sampled at various phases of the co-cultivation. From each of the co-cultures, rRNAs were prepared using "RNeasy Maxikit" (trade name; product of QIAGEN GmbH (Hilden, Germany). Those rRNAs were heated at 95° C. for 5 minutes, and then added to the reaction mixture which had been maintained under the reaction conditions. After they were reacted at 70° C. for 1,000 seconds, the intensity of fluorescence was measured using "Perkin-Elmer LS-50B". The results are plotted in FIG. 11. Incidentally, the total rRNA was measured using "RiboGreen Total RNA Quantification Kit" [trade name; product of Molecular Probe, Inc. (Eugene, Oreg., U.S.A.)].

As is appreciated from the diagram, the mobilizations of the rRNAs of the respective cell strains were consistent with that of the total rRNA. This indicates that the method of the present invention can be effectively used in the FISH method.

Composition of Culture Medium (g/L):

Starch, 10.0; aspartic acid, 0.1; $K_2HPO_4$, 5.0; $KH_2PO_4$, 2.0; $MgSO_4$ $7H_2O$, 0.2; NaCl, 0.1; $(NH_4)_2SO_4$, 0.1.

Aliquots (100 mL, each) of the culture medium were poured in 500-mL Erlenmeyer flasks, and were sterilized in an autoclave at 120° C. for 10 minutes.

Cultivation Conditions:

The above-described cell strains were cultivated beforehand on a slant medium. One roopful of cells was collected from the slant medium, and was then inoculated to the above-described sterilized nutrient broth (NB) in the Erlenmeyer flask. The strains were cultured at 30° C. and 150 rpm under shaking.

Reaction Conditions:

| | |
|---|---|
| Concentrations of 35-nucleotides-chained oligodeoxyribonucleotide 2-O—Me probe: | 1.0 to 10 nM |
| Buffer composition: | 100 mM succinic acid, 125 mM lithium hydroxide, 8.5% lithium dodecyl-sulfite, pH 5.1 |
| Reaction temperature: | 75° C. |

EXAMPLE 20

Example Directed to Intra-Chain Modified Fluorescence Quenching Probes

Target nucleic acids and invention nucleic acid probes, which had the below-described base sequences, were prepared.

To provide probes a), b), amino linkers were introduced into the corresponding base sequences by using "Amino-Modifier C6 dC" (trade name, product of Glen Research Corporation, VA, U.S.A.), and the amino linkers were labeled with BODIPY FL. Except for these, the probes a), b) were synthesized in a similar manner as in Example 8. Therefore, the probe a) was modified with the fluorescent dye on the C base at the 5' end rather than the phosphate group at the 5' end. Modification with BODIPY FL, purification and the like were conducted in a similar manner as described above.

```
Probe a):                       5'C(-BODIPY FL)TTTTTTTTCCCCCCCCC3'
                                (SEQ ID NO: 58)

Probe b):                       5'TTTC(-BODIPY FL)TTTTTTCCCCCCCCC3'
                                (SEQ ID NO: 59)

Target nucleic acid c) for Probe a): 5'GGGGGGGGAAAAAAAAAG3'
                                     (SEQ ID NO: 60)

Target nucleic acid d) for Probe b): 5'GGGGGGGGAAAAAGAAA3'
                                     (SEQ ID NO: 61)
```

Experimenting Method

An experiment was conducted in a similar manner as in Example 9.

Results of the Experiment

As is readily envisaged from the table described below, it has been found that the probe a) and the probe b) are both reduced in the intensity of fluorescence when they hybridize to the corresponding target nucleic acids. It has also been found from the results on the probe b) that modification of a cytosine base in a DNA chain at a position other than the 5' end or 3' end with a fluorescent dye also permits functioning as a fluorescence quenching probe. It has also been found from the results on the probe a) that, even in the case of an end cytosine, modification at a position other than the phosphate group at the 5' end or the OH group at the 3' end with a fluorescent dye makes it possible to obtain a fluorescence quenching probe.

TABLE 6

Results of Example 20

|  | Intensity of fluorescence before hybridization | Intensity of fluorescence after hybridization | Quenching rate of fluorescence (%) |
|---|---|---|---|
| Probe a) + Target nucleic acid c) | 410 | 75 | 81.7 |
| Probe b) + Target nucleic acid d) | 380 | 82 | 78.4 |

A method for analyzing or determining polymorphism and mutation of target nucleic acids will hereinafter be described in Example 21.

EXAMPLE 21

Four oligonucleotides with the below-described base sequences were synthesized using the same DNA synthesizer as that employed in Example 12. Further, an invention nucleic acid probe having the below-described base sequence was also synthesized in a similar manner as in Example 12. The target oligonucleotides were separately hybridized with the probe in solutions. An investigation was then made as to whether or not a single base substitution can be determined from a change in fluorescence intensity. The base sequence of the nucleic acid probe according to the present invention is designed such that, if G exists at the 3' end of any one of the target oligonucleotides, it matches 100% with the base sequence of the particular oligonucleotide. The hybridization temperature was set at 40° C. at which all base pairs between the probe and the target oligonucleotide can hybridize 100%. The concentrations of the probe and target oligonucleotides, the concentration of a buffer solution, a fluorimeter, fluorescence measuring conditions, experimental procedures, and the like were set or chosen as in Example 12.

```
Invention probe:        3'TTTTTTTTGGGGGGGGC5'BODIPY FL/C6
                        (SEQ ID NO: 62)

Target nucleotide No. 1: 5'AAAAAAAACCCCCCCCA3'
                         (SEQ ID NO: 63)

Target nucleotide No. 2: 5'AAAAAAAACCCCCCCCC3'
                         (SEQ ID NO: 64)

Target nucleotide No. 3: 5'AAAAAAAACCCCCCCCI3'
                         (I: hypoxanthine)
                         (SEQ ID NO: 65)

Target nucleotide No. 4: 5'AAAAAAAACCCCCCCCG3'
                         (SEQ ID NO: 66)
```

The results are shown in Table 7. As is appreciated from the table, no change in fluorescence intensity was observed in the case of the target oligonucleotides Nos. 1 to 3, but in the case of the target oligonucleotide No. 4, a decrease as much as 84% was observed.

TABLE 7

| Target oligo-nuceotide | Initial fluorescence intensity (A) | Fluorescence intensity after hybridization (B) | (A–B)/A |
|---|---|---|---|
| No. 1 | 340 | 350 | −0.03 |
| No. 2 | 332 | 328 | 0.01 |
| No. 3 | 343 | 336 | 0.02 |
| No. 4 | 345 | 52 | 0.84 |

In the method of the present invention for analyzing data (for example, the data in columns A and B in Table 7) obtained by the method for analyzing or determining polymorphism and/or mutation of a target nucleic acid (for example, the target oligonucleotide No. 1, 2, 3 or 4), the processing to correct a fluorescence intensity of a reaction system, said fluorescence intensity being obtained when a target nucleic acid is hybridized with a nucleic acid probe according to the present invention (for example, the above-described nucleic acid probe), by a fluorescence intensity of the same reaction system when the target nucleic acid is not hybridized with the nucleic acid probe means the calculation of (A–B)/A in Table 4.

From the above results, it has been found that, when a target nucleic acid is a double-stranded nucleic acid, substitutions of G→A, G←A, C→T, C←T, G→C and G←C can be detected.

EXAMPLE 22

One example of a DNA chip model according to the present invention is illustrated in FIG. 12. Firstly, a modified probe and a surface-treated slide glass were provided. The modified probe had been prepared by introducing an amino group onto the OH group on the carbon atom at the 3' position of ribose at the 3' end of the invention probe, 3'TTTTTTTTGGGGGGGGC5'BODIPY FL/C6 (SEQ ID NO: 62), prepared in Example 21. On the other hand, the surface-treated slide glass had been prepared by treating a slide glass on a surface thereof with a silane coupling agent which contained epoxy groups as reactive groups. A solution with the modified probe contained therein was applied in spots onto the surface-treated slide glass by a DNA chip production apparatus, "GMS" 417 ARRAYER" (manufactured by TAKARA SHUZO CO., LTD., Kyoto, Japan). As a result, the modified probes were bound at the 3' end onto the surface of the slide glass. The slide glass was then placed for 4 hours or so in a closed vessel to bring the reaction to completion. The slide glass was alternately dipped in 0.2% SDS solution and water, twice in each of the solution and water, for about 1 minute each time. Further, the slide glass was immersed for about 5 minutes in a boron solution, which had been prepared by dissolving NaBH$_4$ (1.0 g) in water (300 mL). Shortly after the slide glass was placed for 2 minutes in water of 95° C., the slide glass was alternately dipped in 0.2% SDS solution and water, twice in each of the solution and water, for about 1 minute each time, so that reagents were washed off. The slide glass was-then dried. As a result, a DNA chip according to the present invention was prepared.

Further, arrangement of a minute temperature sensor and a microheater on the lower opposite side of the slide glass at a position corresponding to each spot of the modified probe makes it possible to provide the DNA chip of the present invention with high performance.

A description will next be made of determination of a target nucleic acid by the DNA chip. No change takes place in fluorescence intensity where the target nucleic acid is not hybridized with the probe, where no G-C pair is formed at the fluorescent-dye-labeled end, or where at least one G (guanine) or C (cytosine) base does not exist in the base sequence of the target nucleic acid at a position 1 to 3 bases from an end base portion where the probe and the target nucleic acid are hybridized with each other. However, the intensity of fluorescence decreases conversely where the target nucleic acid is hybridized with the probe, where a G-C pair is formed at the fluorescent-dye-labeled end even if they are hybridized together, or where at least one G (guanine) or C (cytosine) base exists in the base sequence of the target nucleic acid at a position 1 to 3 bases from an end base portion where the probe and the target nucleic acid are hybridized with each other. This fluorescence intensity can be measured by using a DNA chip analyzer, "GMS™ 418 Array Scanner" (manufactured by Takara Shuzo Co., Ltd., Kyoto, Japan).

EXAMPLE 23

Experimental Detection of Single Nucleotide Polymorphism (SNPs)

I) Preparation of Target Nucleic Acid

An oligodeoxyribonucleotide having the base sequence of (5')<u>AAACGATGTGGGAAGGCCCAGACAG</u>CCAGG ATGTTGGCTT AGAAGCAGCC(3') (SEQ ID NO: 67) was synthesized using a DNA synthesizer "ABI 394" (trade name; manufactured by Perkin-Elmer Inc., MA, U.S.A.), and was provided as a target nucleic acid.

II) Preparation of Nucleic Acid Probes

The following six oligodeoxyribonucleotides, which had base sequences hybridizable to a sequence of 15 bases (underlined portion) from the 5' end of the target nucleic acid, were synthesized using the DNA synthesizer "ABI 394" (trade name; manufactured by Perkin-Elmer Inc., MA, U.S.A.). Using "3'-Amino-Modifier CY CPG" (trade name, product of Glen Research Corporation, VA, U.S.A, Catalog No. 20-2957), the OH group at the 3'-position of deoxyribose at the 3' end was aminated. Further, the phosphate group at the 5' end was labeled with BODIPY FL in a similar manner as in Example 12.

1) Probe 100 (100% matched):     (5') CCTTCCCACA TCGTTT (3'), (SEQ ID NO: 68),

2) Probe-T (1 base mismatched):     (5') CCTTCCCATA TCGTTT (3'), (SEQ ID NO: 69), -continued

```
3)  Probe-A (1 base mismatched):     (5') CCTTCCCAAA TCGTTT (3'),
                                     (SEQ ID NO: 70), 4)  Probe-G (1 base mismtached):     (5') CCTTCCCAGA TCGTTT (3'),
                                     (SEQ ID NO: 71), 5)  Probe-TG (2 bases mismatched):   (5') CCTTCCCTGA TCGTTT (3'), and
                                     (SEQ ID NO: 72), and 6)  Probe-TGT (3 bases mismatched):  (5') CCTTCCCTGT TCGTTT (3')
                                     (SEQ ID NO: 73).
```

III) Preparation of DNA Chip

All the DNA probes were dissolved in aliquots of 0.1 M MES (2-morpholinoethanesulfonic acid) buffer (pH 6.5) to give solutions of 500 nM in concentration. Using a DNA microarrayer [a manual chip arrayer composed of "DNA Microarrayer No. 439702" (32-pin type) and "DNA Slide Index No. 439701"; manufactured by Greiner GmbH, Frickerhausen, Germany], the above-described probe solutions were applied in spots onto a DNA chip slide glass (black silylated slide, product of Greiner GmbH, Frickerhausen, Germany). Subsequent to completion of the application in spots, the DNA probes and the slide glass were reacted for 60 minutes at room temperature in a humidity chamber to fix the probes on the slide glass. The slide glass with the DNA probes fixed thereon was then washed with 50 mM THE buffer (pH 7.2). Incidentally, the probe solutions were applied four spots by four spots, respectively. Subsequent to the fixing, the slide glass was washed once with 0.1% SDS (sodium dodecylsulfate), washed twice with distilled water, and then immersed for 5 minutes in a solution of sodium borohydrate (2.5 mg NaBH$_4$/mL-25% ethanol solution). The slide glass was immersed for 3 minutes in a water batch heated at 95° C., and then dried.

A schematic illustration of the DNA chip according to the present invention is shown in FIG. 12. In each probe of the present invention fixed on the slide glass, BODIPY FL develops its color when the probe is not hybridized with a target nucleic acid but, when it is hybridized, its color development is less, namely, reduced than the color developed when it is not hybridized. The slide glass is designed to be heated by microheaters [in the present invention, the experiment was conducted on a transparent warming plate for microscope ("MP-10MH-PG", trade name; product of KITAZATO SUPPLY Co., Ltd., Shizuoka, Japan) as will be described below].

IV) Detection or Determination of SNPs

A target nucleic acid solution of 100 μM in concentration [50 mM THE buffer (pH 7.2) was used] was placed on the DNA chip prepared as described above. A cover glass was placed over the solution, and was sealed with a nail varnish to avoid leakage of the target nucleic acid. A schematic illustration of equipment for detection or determination is shown in FIG. 13. Firstly, a transparent warming plate for microscope ("MP-10MH-PG", trade name; manufactured by KITAZATO SUPPLY Co., Ltd., Shizuoka, Japan) was placed on a stage of an Olympus erect focal laser microscope (Model: AX80). The DNA chip according to the present invention, which had been prepared as described above, was placed on the plate, and the temperature of the plate was changed 3° C. by 3° C. from 95° C. to 33° C. such that the target nucleic acid and the probes were reacted for 30 minutes. Changes in the intensity of fluorescence at each spot in the course of the reaction were measured in an image-inputting manner by a cooled CCD camera ("C4880-40 Model", trade name; manufactured by Hamamatsu Photonics K.K., Shizuoka, Japan).

Inputted images were analyzed by an image analyzer [specifically, an NEC personal computer with image analysis software ("TPlab Spectrum", trade name; available from Signal Analytics, VA, U.S.A.) installed therein] to calculate the luminance values of the individual spots and further to determine a temperature-luminance relationship.

The results of the experiment are diagrammatically shown in FIG. 14. It is appreciated from the diagram that the intensity of luminance was decreased in all the probes. The method of the present invention, therefore, makes it possible to easily monitor a denaturation curve between a probe according to the present invention and a target nucleic acid. As the difference in Tm value between Probe 100, which matches 100% with the target nucleic acid, and a probe, which mismatches by 1 base with the nucleic acid, is as much as 10° C. or greater, they can be easily identified from their denaturation curves. It is therefore understood that an analysis of SNPs can be conducted with ease by using a DNA chip according to the present invention.

PCR methods according to the present invention will hereinafter be described in Examples 24-27.

EXAMPLE 24

Using as a target nucleic acid the 16S rRNA gene in the genome DNA of Escherichia coli, a primer labeled with "BODIPY FL/C6" (a nucleic acid probe according to the present invention) was prepared for the amplification of the nucleic acid.

Preparation of Primer 1 (Eu800R: Reverse Type)

An oligodeoxyribonucleotide having a base sequence of (5')CATCGTTTAC GGCGTGGAC(3') (SEQ ID NO: 74) was synthesized using a DNA synthesizer, "ABI 394" (trade name; manufactured by Perkin-Elmer, Corp.). An oligonucleotide, which had been prepared by treating the phosphate group at the 5' end of the oligodeoxyribonucleotide with phosphatase to form cytosine and then bonding —(CH$_2$)$_9$—NH$_2$, to the OH group on the carbon atom at the 5'-position of the cytosine, was purchased from Midland Certified Reagent Company. From Molecular Probes, Inc., "FluoroReporter Kit F-6082" (trade name) was also purchased, which contained not only "BODIPY EL/C6" propionic acid succinimidyl ester but also a reagent for conjugating the compound to the amine derivative of the oligonucleotide. The kit was caused to act on the above-purchased oligonucleotide, whereby Primer 1 of the present invention labeled with "BODIPY FL/C6" was synthesized.

Purification of Synthesized Product

The synthesized product was dried into a dry product. The dry product was dissolved in 0.5 M $Na_2CO_3/NaHCO_3$ buffer (pH 9.0). The solution was subjected to gel filtration through "NAP-25 Column" (trade name, product of Pharmacia AB, Uppsala, Sweden), whereby unreacted substances were removed. Further, reversed phase HPLC (B gradient: 15 to 65%, 25 minutes) was conducted under the below-described conditions. An eluted main fraction was collected. The collected fraction was lyophilized, whereby Primer 1 of the present invention was obtained with a yield of 50% as calculated relative to 2 mM of the starting oligonucleotide.

The above-described reversed phase chromatography was conducted under the following conditions:

Eluting solvent A: 0.05 N TEAA 5% $CH_3CN$
Eluting solvent B (for gradient elution): 0.05 N TEAA 40% $CH_3CN$
Column: CAPCEL PAK C18 (trade name), 6×250 mm
Elution rate: 1.0 mL/min
Temperature: 40° C.
Detection: 254 nm

EXAMPLE 25

Preparation of Primer 2 (Eu500R/Forward: Forward Type)

Primer 2 composed of an oligodeoxyribonucleotide, which had a base sequence of (5')CCAGCAGCCG CGG-TAATAC(3') (SEQ ID NO: 75), and a fluorescent dye ("BODIPY FL/C6") labeled to the 5' end of the oligodeoxyribonucleotide, was prepared with a yield of 50% in a similar manner as in Example 24.

EXAMPLE 26

Using a test tube containing a liquid culture medium (5 mL; composition: NB, 0.08 g/100 mL) of sterilized nutrient broth (NB) (product of Difco Laboratories Ltd., Surrey, Great Britain), Escherichia coli JM109 was cultivated overnight at 37° C. under shaking. A 1.5-mL aliquot of the culture was centrifuged in a 1.5-mL centrifuge tube, whereby cells were obtained. From the cells, genome DNA was extracted using "DNeasy Tissue Kit" (trade name, product of QIAGENE GmbH, Hilden, Germany). The extraction was conducted following the protocol of the kit. As a result, a 17-ng/µL DNA solution was obtained.

EXAMPLE 27

Using the genome DNA of the above E. coli strain, Primer 1 and/or Primer 2;, PCR reactions were conducted by a method known per se in the art while using "LightCycler™ System" (trade name) marketed from Roche Diagnostics, Mannheim, Germany. Operations were conducted following the manual of the system.

In the above system, PCP was conducted as specified in the manual except that Primer 1 and/or Primer 2 of the present invention were used in place of nucleic acid probes (two nucleic acid probes making use of the FRET phenomenon) and a general primer (a general primer not labeled with any fluorescent dye), both of which are listed in the manual).

PCR was conducted in a hybridization mixture of the following components:
E. coli genome DNA solution 3.5 µL
(final concentration: 0 to 6 ng/20 µL)
(final copy number: 0 to $2.4 \times 10^6$ copies)
Primer solution 0.8 µL
(final concentration: 0.08 µM)
Taq solution 10.0 µL
"MiliQ" purified water 5.7 µL
Final whole volume 20.0 µL Incidentally, the experiments were conducted by using the target nucleic acid, E. coli 16S rDNA, at the concentrations of the respective experiment groups shown in the brief description of FIG. 15 and also by using the primers in the combinations of Primer 1 and/or Primer 2 also shown in the brief description of FIG. 15.

The above Taq solution is a mixed solution of the following reagents:

| | |
|---|---|
| Taq solution | 96.0 µL |
| "MiliQ" purified water | 68.2 µL |
| Taq DNA polymerase solution | 24.0 µL |
| Taq start | 3.8 µL |

Incidentally, these Taq solution and Taq DNA polymerase solution were both included in the "DNA Master Hybridization Probe Kit" (trade name; product of Roche Diagnostics, Mannheim, Germany). Specifically, as the Taq DNA polymerase solution, the 10× conc. solution (red cap) was used by diluting it tenfold. Further, Taq start is an antibody for the Taq DNA polymerase and is marketed by Clontech Laboratories, Inc., CA, U.S.A. Addition of Taq start to a reaction mixture can suppress activity of Taq DNA polymerase up to 70° C. This means that "hot-start" PCR can be performed.

The following reaction conditions were used.
Denaturation Initial: 95° C., 120 seconds
Second and onwards: 95° C., 10 seconds
Annealing 57° C., 5 seconds Measurements were conducted using "LightCycler™ System" (manufactured bid Roche Diagnostics, Mannheim Germany). For each measurement, the detector F1 was used out of the detectors F1-F3 included in the system, and the gain and excitation level of the detector were set at 10 and 75, respectively.

The results are shown in FIG. 15 and FIG. 16. It is appreciated from FIG. 15 and FIG. 16 that the number of cycles at the time of observation of a decrease in fluorescence emission from the fluorescent dye and the number of copies of E. coli 16S rDNA as the target nucleic acid are proportional to each other. In these diagrams, decreases in fluorescence emission from the fluorescent dye are expressed in terms of decreases in the intensity of fluorescence.

FIG. 17 shows a working line for E. coli 16S rDNA, in which the number of copies of E. coli 16S rDNA is expressed as a function of cycles. The correlation coefficient was 0.9973, so that an extremely good correlation was exhibited.

As is understood from the above results, use of the quantitative PCR method of the present invention makes it possible to count the initial number of copies of a target nucleic acid. This means that the concentration of the target nucleic acid can be determined.

EXAMPLE 28

In Example 27, PCR was conducted using the invention probes as primers. In this example, however, PCR according to the present invention was conducted under the following conditions by using a primer of the present invention as opposed to two probes required in the conventional method making use of the FRET phenomenon.

a) Target nucleic acid: 16S rDNA of *Escherichia coli*
b) Primers:
Forward primer E8F: (5')AGAGTTTGAT CCTGGCT-CAG(3') (SEQ ID NO: 76)
Reverse primer E1492R: (5')GGTTACCTTG TTAC-GACTT(3') (SEQ ID NO: 77)
c) Probe: BODIPY FL-(5')CGGGCGGTGT GTAC(3') (SEQ ID NO: 78) (with the 3' end phosphorylated)
d) PCR apparatus: "LightCycler™ System" (trade mark, manufactured by Roche Diagnostics GmbH, Mannheim, Germany)
e) Conditions for PCR:
Denaturation: 95° C. for 10 seconds (95° C. for 60 seconds in the first cycle only)
Annealing: 50° C. for 5 seconds
Extension: 72° C. for 70 seconds
Total cycle number: 70 cycles
f) Fluorescence assay (measurement):
Assay (measurement) was performed once after each of denaturation and extension in each cycle.
g) Composition of reaction mixture:
Total volume: 20 μL
Amount of DNA polymerase ("TaKaRa Ex taq"): 0.5 U
Amount of TaqStart (antibody): 0.3 μL
Concentration of primer: 0.2 μM (common to both primers)
Concentration of probe: 0.05 μM
Concentration of $MgCl_2$: 2 mM
Conc. of BSA (bovine serum albumin): 0.25 mg/mL
Concentration of dNTPs: 0.2 mM (for each nucleotide)

The results are shown in FIG. 18. It is understood from the diagram that the number of cycles at the time of observation of a decrease in fluorescence emission from the fluorescent dye and the number of copies of *E. coli* 16S rDNA as the target nucleic acid are proportional to each other.

As is understood from the above results, use of the quantitative PCR method of the present invention makes it possible to count the initial number of copies of a target nucleic acid. This means that the concentration of the target nucleic acid can be determined.

In the subsequent Examples, the data analysis method of the present invention for analyzing data obtained by using the above-described quantitative PCR method of the present invention will be described.

EXAMPLE 29

Using, as a target nucleic acid, human genome DNA (human β-globin) (TaKara Catalog Product No. 9060) (product of TAKARA SHUZO CO., LTD., Kyoto Japan) (hereinafter called "the human genome DNA"), a primer labeled with "BODIPY FL/C6" was prepared for the amplification of the nucleic acid.

Preparation of Primer KM38+C (Reverse Type)

An oligodeoxyribonucleotide having a base sequence of (5') CTGGTCTCCT TAAACCTGTC TTG (3') (SEQ ID NO: 79) was synthesized using a DNA synthesizer, "ABI 394" (trade name; manufactured by Perkin-Elmer, Corp.) An oligonucleotide, which had been prepared by treating the phosphate group at the 5' end of the oligodeoxyribonucleotide with phosphatase to form cytosine and then bonding —$(CH_2)_9$—$NH_2$, to the OH group on the carbon atom at the 5'-position of the cytosine, was purchased from Midland Certified Reagent Company. From Molecular Probes, Inc., "FluoroReporter Kit F-6082" (trade name) was also purchased, which contained not only "BODIPY FL/C6" propionic acid succinimidyl ester but also a reagent for conjugating the compound to the amine derivative of the oligonucleotide. The kit was caused to act on the above-purchased oligonucleotide, whereby Primer KM38+C of the present invention labeled with "BODIPY FL/C6" was synthesized.

Purification of Synthesized Product

The synthesized product was dried into a dry product. The dry product was dissolved in 0.5 M $Na_2CO_3$/$NaHCO_3$ buffer (pH 9.0). The solution was subjected to gel filtration through "NAP-25 Column" (trade name, product of Pharmacia AB, Uppsala, Sweden), whereby unreacted substances were removed. Further, reversed phase HPLC (B gradient: 15 to 65%, 25 minutes) was conducted under the below-described conditions. An eluted main fraction was collected. The collected fraction was lyophilized, whereby Primer KM38+C of the present invention was obtained with a yield of 50% as calculated relative to 2 mM of the starting oligonucleotide.

The above-described reversed phase chromatography was conducted under the following conditions:
Eluting solvent A: 0.05 N TEAA 5% $CH_3CN$
Eluting solvent B (for gradient elution): 0.05 N TEAA 40% $CH_3CN$
Column: "CAPCEL PAK C18" (trade name), 6×250 mm
Elution rate: 1.0 mL/min
Temperature: 40° C.
Detection: 254 nm

EXAMPLE 30

Preparation of Primer KM29 (Forward Type)

An oligodeoxyribonucleotide having a base sequence of (5')GGTTGGCCAA TCTACTCCCA GG(3') (SEQ ID NO: 80) was synthesized in a similar manner as in Example 26.

Comparative Example 1

This Comparative Example is directed to use of a data analysis software which did not include the processing step that an intensity of fluorescence during an extending reaction of a nucleic acid is divided using an intensity of fluorescence at the time of a thermal denaturing reaction [i.e., the processing of the formula (1)].

Using the above-described human genome DNA, Primer KM38+C and Primer KM29, PCR reactions were conducted by "LightCycler™ System". The intensity of fluorescence was measured in each cycle.

Incidentally, the PCR in this Comparative Example employed the above-described primers labeled with the fluorescent dye, and is a novel real-time quantitative PCR method in which a decrease in fluorescence emission is measured rather than an increase in fluorescence emission. An analysis of data was conducted using the software of the system itself. The PCR in this Comparative Example was conducted following the manual of the system except that the invention primers KM38+C and KM29 were used instead of the nucleic acid probes listed in the manual (two probes making use of the FRET phenomenon) or an ordinary primer (an ordinary primer not labeled with any fluorescent dye).

PCR was conducted in a hybridization mixture of the following components:

| | |
|---|---|
| Human genome DNA (final concentration: 1 to 10,000 copies) | 1.0 µL |
| Primer solution (final concentration: 0.1 µM) | 4.0 µL |
| Taq solution | 10.0 µL |
| "MiliQ" purified water | 5.0 µL |
| Final whole volume | 20.0 µL |

Incidentally, the experiments were conducted by using the human genome DNA at the concentrations of the respective experiment groups shown in the brief description of FIG. 19. The final concentration of $MgCl_2$ was 2 mM.

The above-described "Taq solution" is a liquid mixture of the following reagents:

| | |
|---|---|
| Taq solution | 96.0 µL |
| "MiliQ" purified water | 68.2 µL |
| Taq DNA polymerase | 24.0 µL |
| Taq start | 3.8 µL |

Incidentally, the "Taq solution" and the "Taq DNA polymerase solution" are included in "DNA Master Hybridization Probes" (trade name) marketed by Roche Diagnostic GmbH, Mannheim, Germany. Specifically, the "Taq DNA polymerase solution" was used by diluting "10× conc." (red cap) tenfold. Further, the "Taq start" is an antibody to Taq DNA polymerase, and is marketed by Clontech laboratories, Inc., CA, U.S.A. Its addition to the reaction mixture makes it possible to inhibit the activity of Taq DNA polymerase up to 70° C. In other words, "hot-start" PCR can be performed.

The following reaction conditions were used.

Denaturation Initial: 95° C., 60 seconds Second and onwards: 95° C., 10 seconds

Annealing 60° C., 5 seconds

DNA extending reaction: 72° C., 17 seconds

Measurements were conducted using "LightCycler™ System". For each measurement, the detector F1 was used out of the detectors F1-F3 included in the system, and the gain and excitation level of the detector were set at 10 and 75, respectively.

PCR was conducted as described above, during which the intensities of fluorescence in individual cycles were measured. The results are shown in FIG. 19. Described specifically, with respect to each of the human genome DNAs of the respective copy numbers, the intensity of fluorescence was measured at the time of a denaturing reaction and also at the time of a nucleic acid extending reaction, both in each cycle, and was printed. It is observed that the intensity of fluorescence remained constant at the time of the denaturing reaction irrespective of the cycle but a decrease in fluorescence took place from the 25th cycle at the time of the nucleic acid extending reaction. It is also understood that this decrease occurs earlier as the number of copies of the human genome DNA increases.

As is shown in FIG. 19, the intensities of fluorescence in initial cycles were not constant irrespective of the number of copies of the human genome DNA. The following steps (b)-(j) were, therefore, added to the data analysis method for use in this Comparative Example.

(b) Assuming that the intensity of fluorescence in the $10^{th}$ cycle is 1, the intensity of fluorescence in each cycle is converted, namely, calculation is conducted in accordance with the following formula (8):

$$C_n = F_n(72)/F_{10}(72) \qquad (8)$$

where $C_n$: a converted value of the intensity of fluorescence in each cycle, $F_n(72)$: the intensity of fluorescence at 72° C. in each cycle, and $F_{10}(72)$: the intensity of fluorescence after extending reaction at 72° C. in the $10^{th}$ cycle.

(c) Each converted value obtained in step (b) is displayed on a display and/or printed as a function of cycle.

(d) From the converted value in each cycle as obtained in step (b), the rate of a change in fluorescence intensity (decrease or quench, %) is calculated in accordance with the following formula (9):

$$F_{dn} = \log_{10}\{100 - C_n \times 100)\} \qquad (9)$$

$$F_{dn} = 2 \log_{10}\{1 - C_n\} \qquad (9)$$

where $F_{dn}$: the rate of a change in fluorescence intensity (decrease or quench, %), and $C_n$: the value obtained in accordance with the formula (8).

(e) Each converted value obtained in step (d) is displayed on a display and/or printed as a function of cycle.

(f) Data processed in step (d) are compared with 0.5 as a threshold, and the number of cycles the data of which reach the threshold is counted.

(g) A graph is prepared by plotting values, which have been counted in step (f), along X-axis and the numbers of copies before the initiation of the reaction along Y-axis.

(h) The graph prepared in step (g) is displayed on a display and/or printed.

(i) A correlation coefficient or relational formula of the line drawn in step (h) is calculated.

(j) The correlation coefficient or relational formula calculated in step (i) is displayed on a display and/or printed.

Using the above-described data analysis software, the data obtained in FIG. 19 were then processed as will be described hereinafter.

FIG. 20 is a print-out of the data processed in step (b) [process (c)]. Namely, assuming that the intensity of fluorescence in the $10^{th}$ cycle was 1, the fluorescence intensities in the individual cycles were converted, and the converted values were plotted against the corresponding cycles.

FIG. 21 is a print-out of the data processed in step (d) [process (e)]. Namely, decreases (%) (quenches, %) of the respective fluorescence intensities were calculated from the plotted values in FIG. 20, and the values so calculated were plotted against the corresponding cycles.

FIG. 22 is a print-out of the graph prepared in step (g) based on the data processed in step (f) [step (h)]. Namely, it is a graph obtained by using a decrease of 0.5 in fluorescence intensity as a threshold, plotting along X-axis the number of cycles in which the threshold was reached, and also plotting along Y-axis the numbers of copies of the human genome DNA before the initiation of the respective reactions. The correlation coefficient (R2) of the line in this graph was calculated in step (i), and was then printed [step (j)]. The correlation coefficient was 0.9514. As is understood, it was hardly possible, with this correlation coefficient, to determine an accurate number of copies this correlation coefficient was

EXAMPLE 31

This Example is Directed to an Experiment in which Processing of Data was Performed by Using the Data Analysis Method of the Present Invention PCR was conducted in a similar manner as in Comparative Example 1. The processing of the data was performed through similar steps as in Comparative Example 1 except that the following step (a) was added before the step (b) and the steps (b), (d) were modified as will be described below.
(a) The intensity of fluorescence in each cycle in a reaction system in which an amplified nucleic acid hybridized to a nucleic acid primer labeled with a fluorescent dye as a nucleic acid probe of the present invention [namely, the intensity of fluorescence at the time of a nucleic acid extending reaction (72° C.)] was corrected in a correction processing step such that the intensity of fluorescence was divided by the intensity of fluorescence in the reaction system measured at the time of dissociation of the nucleic acid hybrid complex (the hybrid complex formed by hybridization of the amplified nucleic acid and the nucleic acid primer [namely, the intensity of fluorescence at the time of completion of the thermal denaturing reaction of the nucleic acid (95° C.)], that is, the actually-measured intensities of fluorescence were corrected in accordance with the following formula (1):

$$f_n = f_{hyb,n} / f_{den,n} \quad (1)$$

where
$f_n$: a correction value for the intensity of fluorescence in each cycle,
$f_{hyb,n}$: the intensity of fluorescence at 72° C. in each cycle, and
$f_{den,n}$: the intensity of fluorescence at 95° C. in each cycle.
It is FIG. 23 that was obtained by plotting the thus-obtained values against the corresponding cycles.
(b) A processing step that the values correction-processed by formula (1) in the respective cycles were introduced into the formula (3) to calculate the rates of changes (decreases or quenches, %) in fluorescence between the samples in the respective cycles, namely, a step for performing processing in accordance with the following formula (10):

$$F_n = f_n / f_{25} \quad (10)$$

where
$F_n$: a processed value in each cycle,
$f_n$: a value of each cycle as obtained in accordance with formula (1), and
$f_{25}$: a value of the $25^{th}$ cycle as obtained in accordance with formula (1).
Formula (10) is similar to formula (3) except for a=25.
(d) A step that the processed value of each cycle as obtained in step (b) was subjected to processing in accordance with formula (6) to obtain the logarithm of the rate of a change (decrease or quench, %) in fluorescence intensity, namely, a step for performing processing in accordance with the following formula (11):

$$\log_{10}\{(1-F_n) \times 100\} \quad (11)$$

where
$F_n$: value obtained in accordance with formula (10).
Formula (11) is similar to formula (6) except for b=10 and A=100.
The above results are shown in FIGS. 24 and 25.
FIG. 24 is a print-out obtained by plotting the values, which have been processed in steps (a) and (b), against the corresponding cycles.
FIG. 25 is a print-out obtained by processing the values, which have been obtained in FIG. 24, in a similar manner as in step (d) and then plotting the thus processed values against the corresponding cycles.
Next, based on the graph of FIG. 25, processing was performed through steps (f), (g) and (h). Described specifically, as in Comparative Example 1, 0.1, 0.3, 0.5, 0.7, 0.9 and 1.2 were chosen as thresholds for $\log_{10}$ (rates of changes in fluorescence intensity, %) on the basis of the graph of FIG. 25. The numbers of cycles in which the logarithms reached the thresholds were plotted along X-axis, while the numbers of copies of the human genome DNA before the initiation of reactions were plotted along Y-axis, whereby working lines were drawn. The results are shown in FIG. 26. Correlation coefficients ($R^2$) determined by conducting processing in steps (i) and (j) with respect to those working lines were 0.998, 0.999, 0.9993, 0.9985, 0.9989 and 0.9988, respectively. From those correlation coefficients, it was able to confirm that adoption of 0.5 as a threshold (correlation coefficient: 0.9993) is desired. It is understood that, with a working line having this correlation coefficient, the number of copies before initiation of a reaction can be accurately determined with respect to a nucleic acid sample the number of copies of which is unknown.

EXAMPLE 32

This Example is directed to an analysis of a melting curve of a nucleic acid and also to an analysis of a Tm value.
A software comprising the following steps was created:
1) with respect to a nucleic acid amplified by the novel PCT method of the present invention, gradually heating the amplified nucleic acid from a low temperature until the nucleic acid is completely denatured (for example, from 50° C. to 95° C.), or gradually lowering it; 2) in step 1), measuring the intensity of fluorescence at short time intervals (for example, at intervals equivalent to temperature rises of from 0.2° C. to 0.5° C.); 3) displaying the measurement results of step 2) on a display as a function of time, namely, displaying a melting curve of the nucleic acid; 4) differentiating the melting curve obtained in step 3); 5) displaying, on a display, derivatives (−dF/dT, F: fluorescence intensity, T: time) obtained in step 4); and 6) determining a point of inflection from the derivatives obtained in step 5). The software was combined with the above-described data analysis software of the present invention. Using "LightCycler™ System" in which a computer-readable recording medium with the data analysis software recorded therein had been installed, the novel real-time quantitative PCR reaction of the present invention was conducted to analyze the melting curve of the nucleic acid. In the present invention, the intensity of fluorescence increases with the temperature.
With respect to 1 copy and 10 copies of the same human genome DNA as in Example 31, PCR was conducted in a similar manner as in Example 29. FIG. 27 is a print-out of data obtained by processing data of the PCR in steps 1), 2), 3), 4) and 5). Concerning 75th amplification products of the 1 copy and 10 copies, data were processed in steps 1), 2 and 3) of this Example. The nucleic acid melting curves so obtained are shown in FIG. 28. Those curves were differentiated in step 4), and points of inflection (Tm values) were determined in steps 5) and 6). The differentiated curves with the points of inflection are illustrated in FIG. 29. It was ascertained from FIG. 29 that the amplification products of the 1 copy and 10 copies were different products as their Tm values were different from each other.

The following Examples relate to quantitative polymorphous analysis methods.

EXAMPLE 33

Preparation of Fluorescence Quenching Probes According to the Present Invention, Probe Eu47F and Eu1392R (1) Synthesis of the Fluorescence Quenching Probe Eu47F The fluorescence quenching probe Eu47F, which was composed of a deoxyribooligonucleotide having the base sequence of (5')CITAACACATGCAAGTCG(3') (I: inosine) (SEQ ID NO: 81) and labeled on the phosphate group at the 5' end thereof with "BODIPY FL" as will be described below, was synthesized by a DNA synthesizer "ABI 394" (trade name, manufactured by Perkin-Elmer Inc., MA, U.S.A.).

(2) Synthesis of Eu1392R

A deoxyribooligonucleotide the base sequence of which was (5')TTGTACACACCGCCCGTCA(3') (SEQ ID NO: 82) was synthesized.

The deoxyribooligonucleotide with —$(CH_2)_6$—$NH_2$ bound on the phosphate group at the 5' end thereof was purchased from Midland Certified Reagent Company, TX, U.S.A. From Molecular Probes, Inc., "FluoroReporter Kit F-6082" (trade name) was also purchased, which contained not only "BODIPY FL" propionic acid succinimidyl ester but also a reagent for conjugating the compound to the amine derivative of the oligonucleotide. The kit was caused to act on the above-purchased oligonucleotide to synthesize the above-described invention fluorescence quenching probe labeled with "BODIPY FL".

Incidentally, purification of each of the above-described synthesized products was conducted as will be described hereinafter.

Each synthesized product was dried into a dry product. The dry product was dissolved in 0.5 M $Na_2CO_3$/$NaHCO_3$ buffer (pH 9.0). The solution was subjected to gel filtration through "NAP-25 Column" (trade name, product of Pharmacia AB, Uppsala, Sweden), whereby unreacted substances were removed. Further, reversed phase HPLC (B gradient: 15 to 65%, 25 minutes) was conducted under the below-described conditions. An eluted main fraction was collected. The collected fraction was lyophilized, whereby the target product was obtained with a yield of 50% as calculated relative to 2 mM of the starting oligonucleotide.

Conditions for Reversed Phase Chromatography;
  Eluting solvent A: 0.05 N TEAA 5% $CH_3CN$
  Eluting solvent B (for gradient elution): 0.05 N TEAA 40% $CH_3CN$
  Column: "CAPCEL PAK C18" (trade name), 6×250 mm
  Elution rate: 1.0 mL/min
  Temperature: 40° C.
  Detection: 254 nm

EXAMPLE 34

(1) Cultivation of *Escherichia coli* JM109

Using Medium 53 (composition: casein peptone (tripsin digest of casein), 10 g; yeast extract, 5 g; glucose, 5 g; salt, 5 g; distilled water, 1000 mL), *Escherichia coli* JM109 was cultivated (culture medium 50 mL/250 mL Erlenmeyer flask, 37° C., 12 hours, shaking culture). Cells were collected from the culture (centrifugation under 10,000 rpm for 5 minutes, washed twice with distilled water).

(2) Preparation of DNA of 16S rRNA

Using "SOGEN Kit" (trade name, product of NIPPON GENE CO., LTD., Tokyo, Japan), whole RNAs were extracted from the cells in accordance with the protocol of the kit.

Using "BcaBEST™ RNA PCR Kit" (product of Takara Shuzo Co., Ltd., Kyoto, Japan), the extract was subjected with respect to 16s RNA to amplification and reverse transcription reaction (RT-PCR) under known usual conditions in accordance with the protocol of the kit. Upon these amplification and reverse transcription reaction (RT-PCR), the above-described fluorescence quenching probe EU1392R according to the present invention was used as a primer. Subsequently, RNA was cleaved by RNase H (30° C., 20 minutes), and pure cDNA of the 16S rRNA gene was obtained. The concentration of cDNA was determined using "OliGreen$^R$ssDNA Quantitation Kit" (trade name; product of Molecular Probes, Inc., OR, U.S.A.).

EXAMPLE 35

(1) Quantitative PCR, Data Analysis, and Preparation of Working Curves for cDNA

With respect to the above-described cDNA solution, a real-time monitoring quantitative PCR reaction was conducted using the invention fluorescence quenching probe EU47F as a forward primer and the invention fluorescence quenching probe Eu1392R as a reverse primer.

Using "LightCycler™ System" (trade name, manufactured by Roche Diagnostic GmbH, Mannheim, Germany) as a real-time monitoring quantitative PCR system, a reaction was conducted in accordance with the procedures described in the manual. Incidentally, "TaKaRaTaq™" (product of Takara Shuzo Co., Ltd., Kyoto, Japan) was used as DNA polymerase.

PCR was conducted with the following components:

| | |
|---|---|
| E. coil cDNA | 3.5 µL |
| (final concentration: $10^2$ to copies) | |
| Primer solution | 4.0 µL |
| (final concentration: 0.1 µM) | |
| TaKaRaTaq ™ | 10.0 µL (0.5 unit) |
| "MiliQ" purified water | 5.0 µL |
| Final whole volume | 20.0 µL |

Incidentally, the experiment was conducted using the cDNA in the copy numbers specified in the brief description of FIG. 30. The final concentration of $MgCl_2$ was 2 mM.

The reaction was conducted under the following conditions:
  Denaturation Initial: 95° C., 60 seconds Second and onwards: 96° C., 10 seconds
  Annealing 50° C., 5 seconds
  DNA extension: 72° C., 60 seconds Measuring conditions were set as follows:
Exciting light: 488 nm
Measuring fluorescent color: 530 nm Real-time monitoring quantitative PCR was conducted under similar conditions as described above, and the intensities of fluorescence in individual cycles was actually measured. The actually measured values were analyzed in accordance with the data analysis method of the present invention. Specifically, the data were processed through the following steps:

(a) The intensity of fluorescence in each cycle in the reaction system in which the amplified nucleic acid hybridized to the nucleic acid primer labeled with the fluorescent dye [namely, the intensity of fluorescence at the time of the nucleic acid extending reaction (72° C.)] was corrected in a correction processing step such that the intensity of fluorescence was divided by the intensity of fluorescence in the reaction system measured at the time of complete dissociation of the nucleic acid hybrid complex (the hybrid complex formed by hybridization of the amplified nucleic acid and the nucleic acid primer [namely, the intensity of fluorescence at the time of completion of the thermal denaturing reaction of the nucleic acid (96° C.)], that is, the actually-measured intensities of fluorescence were corrected in accordance with the following formula (1):

$$f_n = f_{hyb,n}/f_{den,n} \quad (1)$$

where
  $f_n$: a correction value for the intensity of fluorescence in each cycle,
  $f_{hyb,n}$: the intensity of fluorescence at 72° C. in each cycle, and
  $f_{den,n}$: the intensity of fluorescence at 96° C. in each cycle.

(b) A processing step that the values correction-processed by formula (1) in the respective cycles were introduced into the formula (3) to calculate the rates of quenches (%) in fluorescence between the samples in the respective cycles, namely, a step for performing processing in accordance with the following formula (10):

$$F_n = f_n/f_{25} \quad (10)$$

where
  $F_n$: a processed value in each cycle,
  $f_n$: a value of each cycle as obtained in accordance with formula (1), and
  $f_{25}$: a value of the 25$^{th}$ cycle as obtained in accordance with formula (1).

Formula (10) is similar to formula (3) except for a=25.

(c) A step that the processed value of each cycle as obtained in step (b) was subjected to processing in accordance with formula (6) to obtain the logarithm of the rate of a change (decrease or quench, %) in fluorescence intensity, namely, a step for performing processing in accordance with the following formula (11):

$$\log_{10}\{(1-F_n) \times 100\} \quad (11)$$

where
  $F_n$: value obtained in accordance with formula (10).
  Formula (11) is similar to formula (6) except for b=10 and A=100.

The above results are shown in FIG. 30.
FIG. 30 is a print-out obtained by plotting the values, which have been calculated in steps (a), (b) and (c), against the corresponding cycles.

Next, based on the graph of FIG. 30, processing was performed through the following steps (d) and (e).

d) A step that data processed in step (c) are compared with 0.2 as a threshold, and the number of cycles the data of which reach the threshold is counted.

(e) A step that a graph is prepared by plotting values, which have been calculated in step (d), along X-axis and the numbers of copies before the initiation of the reaction along Y-axis, that is, a working line (FIG. 31) for *Escherichia coli* cDNA is prepared.

FIG. 31 shows the final results obtained when data obtained by the quantitative PCR method of the present invention were processed by the data analysis method of the present invention, namely, through steps (a), (b), (c), (d) and (e)

EXAMPLE 36

(1) Construction of a Polymorphisms System (a Co-Cultivation System of Microorganisms)

Ten (10) bacteria strains shown in Table 5 were purchased from DSMZ (Deutsche Sammlung von Mikroorganismen und Zellkulturen GmbH, Braunschweig, Germany). Using Medium 53 described above, they were separately cultured. Culture conditions were similar to the above-described conditions for *Escherichia coli*. From each culture, cells were collected (centrifugal separation at 10,000 rpm for 10 minutes; washed twice with distilled water). From each sample of cells, whole RNAs were extracted in a similar manner as described above by using "SOGEN Kit" (trade name; product of NIPPON GENE CO., LTD., Tokyo, Japan).

TABLE 8

| | Strain No. | DSMZ No. | HhaI fragment (bp) | Molar fraction % determined from T-RFLP | Number of quantitated copies | Number of quantitated copies/ number of initially added copies |
|---|---|---|---|---|---|---|
| 1 | *Paracoccus pantotrophus* | 65 | 22 | 9.5 | 27400 | 0.91 |
| 2 | *Sphingomonas natatoria* | 3138T | 43 | 10.9 | 31400 | 1.05 |
| 3 | *Bdellovibrio stolpii* | 12778 | 52 | 9.7 | 27900 | 0.93 |
| 4 | *Microbacterium imperiale* | 20530 | 104 | 9.4 | 27100 | 0.90 |
| 5 | *Pseudomonas fluorescens* | 50108 | 168 | 10.4 | 30000 | 1.00 |
| 6 | *Agromyces medislanum* | 20152 | 332 | 9.3 | 26800 | 0.89 |
| 7 | *Cellulomonas cellulans* | 43879 | 404 | 9.7 | 27900 | 0.93 |

TABLE 8-continued

| Strain No. | DSMZ No. | HhaI fragment (bp) | Molar fraction % determined from T-RFLP | Number of quantitated copies | Number of quantitated copies/ number of initially added copies |
|---|---|---|---|---|---|
| 8 *Brevibacterium liquefaciens* | 20579 | 432 | 9.9 | 28500 | 0.95 |
| 9 *Leminorella grimontii* | 5078 | 531 | 10.4 | 30000 | 1.00 |
| 10 *Rhodococcus luteus* | 43673 | 626 | 10.8 | 31100 | 1.04 |

In a similar manner as in the above-described case of *Escherichia coli*, pure cDNAs of the 16S rRNA genes of the respective strains were obtained. The respective concentrations of the thus-obtained cDNAs of the 10 strains were determined in a similar manner as in the above-described case of *Escherichia coli*. The solutions the cDNA concentrations of which had been ascertained were diluted with distilled water to 300,000 copies/μL. Concerning the 10 strains, the diluted solutions were mixed in equal amounts to provide a co-cultivation system of microorganisms, in other words, a polymorphous system (hereinafter called a "polymorphisms system"). As the cDNAs of the 10 strains are each contained at the concentration of 300,000 copies/μL in the polymorphous system, the cDNAs are contained as a whole at a concentration of 3,000,000 copies/μL.

(2) Real-Time Monitoring Quantitative PCR

With respect to the cDNAs in the above-described polymorphous system, real-time monitoring quantitative PCR was conducted in a similar manner as in the above-described *Escherichia coli* by using the fluorescent quenching probes Eu47F and Eu1392R of the present invention as primers common to the strains.

A polymorphous sample was added to a reaction mixture to give a concentration of 300,000 copies/20 μL in terms of absolute count. In real-time monitoring quantitative PCR of the polymorphous system, the reaction was terminated in the 22$^{nd}$ cycle in which a decrease in the intensity of fluorescence was observed and which was an exponential growth phase of the genes (see FIG. 30). The number of copies of cDNAs in the reaction mixture of real-time monitoring quantitative PCR conducted on the polymorphous system was 288,000 copies (see FIG. 31). Since the initially-added amount, that is, the calculated count was 300,000 copies, the working line prepared by the method of the present invention has been confirmed to show good quantitativeness.

EXAMPLE 37

Polymorphous Analysis (1) Analysis by T-RFLP

After a PCR reaction was conducted as described above, amplified products were purified using a column ("Microcon PCR", trade name; product of Millipore Corporation, Bedford, Mass., U.S.A.). Purified products were treated overnight with a restriction endonuclease HhaI (recognition site: GCG/C, /: cleaved site). After completion of the treatment, only cleaved fragments were purified through columns ("Microcon" and "Micropure-Ez", trade names; products of Millipore Corporation, Bedford, Mass., U.S.A.). The sizes of cDNA fragments of the respective strains after the treatment with the restriction endonuclease are shown in Table 8.

The cDNA solution, to which the column chromatographic purification had been applied, was subjected to thermal denaturation, followed by a T-RFLP analysis by a sequencer ("ABI PRISMTH 310", trade name; manufactured by Perkin Elmer—Applied Biosystems Inc., CA, U.S.A.). A peak pattern of the T-RFLP analysis is shown in FIG. 32. Each peak was quantitated using a standard "BODIPY FL"-modified fragment the concentration of which was known. The molar fractions (%) of the individual peaks were determined. As a result, the molar fractions (%) all fell within a range of from 9.4 to 10.8 and no substantial difference was observed in the efficiencies of PCR amplification of the cDNA fragments of the respective strains see Table 8). The ratio of the number of quantitated copies to the number of initially added copies ranged from 0.89 to 1.04 (see Table 8). It has hence been found that the numbers of initial copies of cDNAs of the individual strains in a polymorphous system can be accurately quantitated by this method.

EXAMPLE 38

Example Directed to a Real-Time Quantitative PCR Method Making Use of Fluorescence Emitting Probes as Primer (Hereinafter Called "Fluorescence Emitting Primers") and a Quantitative Polymorphisms Analysis Method Making Use of the Real-Time Quantitative PCR Method A description will be made about an Example directed to a real-time quantitative PCR method making use of fluorescence emitting probes and a quantitative polymorphous analysis method making use of the real-time quantitative PCR method.

1 Experimental Procedures and Conditions

Preparation of an Artificial Co-Cultivation System of Microorganisms (Template)

An artificial co-cultivation system of microorganisms was prepared. Using it as a model system, effectiveness of a quantitative polymorphous analysis method was proven. For the experiment, 10 kinds of microorganisms shown in Table 9 were purchased from DSMZ. The individual strains were separately cultivated using Medium 53. From the cultures, cells were collected, and total DNAs were extracted with a kit reagent "ISOGEN" (trade name, product of NIPPON GENE CO., LTD., Tokyo, Japan) in accordance with its protocol. Using Eu47F (CITAACACATGCAAGTCG, I: inosine) (SEQ ID NO: 81) and Eu1392R (TTGTACACAC- CGCCCGTCA) (SEQ ID NO: 82) as primers, a PCR reaction was conducted on 16s RNA genes as amplification targets. The thus-amplified products of the 10 kinds of 16S rRNA genes were quantitated by "PicoGreen.sup.RdsDNA Quantitation Kit" (trade name, product of Molecular Probes, Inc., OR, U.S.A.), and were then separately diluted with sterilized distilled water to give a concentration of 300,000 copies/mL. The thus-diluted solutions were mixed in equal amounts to provide an artificial co-cultivation system model of microorganisms. This artificial co-cultivation system model of microorganisms contained amplified products of 16S rRNA genes of The 10 microorganisms at concentrations of 30,000 copies/mL, respectively. The total concentration of the amplified products of the 16S rRNA genes was, therefore, 330,000 copies/mL.

Procedures of a Real-Time Quantitative PCR Experiment Making Use of Fluorescence Emitting Primers According to the Present Invention Using the above-described artificial co-cultivation system of microorganisms (the mixed 16S rRNA gene sample) as a target, quantitative PCR was conducted using fluorescence emitting primers dually modified with Texas Red and Dabcyl. Employed as common primers were Euq7F-modi (CIT-AACACATGCAAGTCG, I:inosine) (SEQ ID NO: 81) and Eu1392R(TTGTACACACCGCCCGTCA) (SEQ ID NO: 82). Eu47F-modi had similar base sequence as Eu47F, but the $9^{th}$ T from the 5' end was modified with Texas Red and the $9^{th}$ T was modified with Dabcyl. The modifications with Texas Red and Dabcyl were conducted in a similar manner as in Example 7. As a quantitative PCR apparatus, "cycler" (trade mark, manufactured by Bio-Rad laboratories, Inc., CA, U.S.A.) was used. The first denature as carried out at 95° C. for 60 seconds, and PCR cycles were Conducted under the following conditions: denature: 95° C./60 seconds, annealing: 50° C./60 seconds and extension: 72° C./70 seconds. The PCR reaction was terminated in an exponential growth phase such that the initial composition of the genes would not be altered (no PCR bias would be applied). As the concentrations of the primers, Eu47F and Eu1932R were both set at 0.1 µM, respectively, in terms of final concentration. As a DNA polymerase, "TaKaRa Taq™" (trade name, product of Takara Shuzo Co., Ltd., Kyoto, Japan) was used at a concentration of 0.5 unit/20 µL. The concentration of Mg ions was set at 2 mM. dNTP was added to give a final concentration of 2.5 mM, respectively. Using "AntiTaq body" (trade name, product of Clontech Laboratories, Inc., CA, U.S.A.), "hot-start" PCR was conducted following the maker's instruction manual. As a standard sample for the preparation of a working line, an amplified product of the 16S rDNA gene of E. coli was used. The preparation of the amplified product of the 16S rDNA gene of E. coli was conducted in a similar manner as the above-described artificial co-cultivation system of microorganisms. Subsequent to the preparation of the working line, quantitation of the artificial co-cultivation system of microorganisms was conducted. The gene concentration of the artificial co-cultivation system of microorganisms was adjusted to give a concentration of 300,000 copies/20 µL in terms of absolute count (20 µL: total amount). Measurement of fluorescence was conducted once after denature and once after annealing in each cycle. Similarly to the quenching rate of fluorescence (%), the emitting race of fluorescence (%) was determined by correcting the hntensity of fluorescence after annealing (at the time of hybridization) with the intensity of fluorescence after denaturation (at the time of dissociation).

A specific calculation formula can be expressed as:

$$F_n: \{(f_{hyb'n}/f_{den'n})/(f_{hyb'n}/f_{den'n})\} \times 100$$

where
$F_n$: Emitting rate of fluorescence (%) in the nth cycle,
$f_{hyb/n}$: Intensity of fluorescence during extension (hybridization) in the $n^{th}$ cycle,
$f_{den'n}$: Intensity of fluorescence during denaturation (dissociation) in the $n^{th}$ cycle,
$f_{hyb'n}$: Intensity of fluorescence after extension (hybridization) in a cycle ($n'^{th}$ cycle) preceding occurrence of an emission of fluorescence from an amplified product, and
$f_{den'n}$: Intensity of fluorescence after denaturation (dissociation) in the cycle ($n'^{th}$ cycle) preceding the occurrence of the emission of fluorescence from the amplified product.

Analysis by T-RFLP

After completion of the real-time quantitative PCR reaction, purification of the amplified products was conducted through a column ("Microcon PCR", trade name; product of Millipore Corporation, Bedford, Mass., U.S.A.). Purified products were treated overnight with a restriction endonuclease HhaI (recognition site: GCG/C, /: cleaved site). After completion of thermal denaturation, a solution which contained restriction fragments was subjected to a T-RFLP analysis by a sequencer ("ABI PRISMTH 310", trade name; manufactured by Perkin Elmer—Applied Biosystems Inc., CA, U.S.A.). After the individual restriction fragments were quantitated using fluorescence emitting probes of the same chain lengths as standards, respectively, the molar fractions (%) of the individual peaks were determined.

2) Results

Results of Real-Time Quantitative PCR Making Use of Fluorescence Emitting Primers The results are shown in FIG. 33 and FIG. 34. As is appreciated from FIG. 33, it has been confirmed that monitoring of amplified products is feasible by using fluorescence emitting primers. Further, a relationship between the number of cycles required to reach a threshold [log $F_n$ (emitting rate of fluorescence, %)=1.6] and the count of DNA copies added initially is illustrated in FIG. 34. As is readily appreciated from this diagram, it is understood that the number of cycles and the number of copies added initially is in a linear relationship. Accordingly, it is indicated from this diagram that the quantitation of initial copies of a target gene can be accurately achieved from the $n^{th}$ number of a cycle in which the threshold is reached. In the artificial co-cultivation system of microorganisms, the PCR reaction was terminated in a cycle ($23^{rd}$ cycle) in which logarithmic growth was observed (see FIG. 33). From the working line shown in FIG. 34, the number of copies of the 16S rRNA in the artificial co-cultivation system of microorganisms was quantitated to be about 296,000 copies. Since the count of the initially added copies was 300,000 copies, the good quantitativeness of this method was confirmed.

Results of the Analysis by T-RFLP

The amplified products of the real-time quantitative PCR were analyzed by the T-RFLP method to quantitate restriction fragments of the 16S rRNAs genes of the respective strains. As a result, the molar fractions (%) of all the peaks fell within a range of from 9.5 to 10.6, and no difference was observed in the efficiency of PCR amplification depending on the kind of 16S rNA gene (see Table 9). The number of initial copies of 16S rRNA gene of each constituent microorganism was determined by multiplying the total number of copies of 16S rRNA gene, which had been determined by the quantitative PCR, with the corresponding molar fraction (see Table 9). Concerning the 16S rRNA gene of each strain, the ratio of the number of quantitated copies to the number of initially added copies fell in a range of from 0.94 to 1.05 (see Table 9). It has hence been proven that the quantitation of initial copies of mixed genes in a artificial co-cultivation system of microorganisms (quantitation of target nucleic acids) by this method has good accuracy.

TABLE 9

Results of T-RFLP (Determined by Fluorescence Emitting Probes)

| Strain No. | DSMZ No. | Length of HhaI fragment (bp) | Molar fraction % determined from T-RFLP | Number of quantitated copies | Number of quantitated copies/ number of initially added copies |
|---|---|---|---|---|---|
| Paracoccus pantotrophus | 65 | 22 | 9.50 | 28120 | 0.94 |
| Sphingomonas natatoria | 3183T | 43 | 10.10 | 29896 | 1.00 |
| Bdellovibrio stolpii | 12778 | 52 | 9.90 | 29304 | 0.98 |
| Microbacterium imperiale | 20530 | 104 | 9.60 | 28416 | 0.95 |
| Pseudomonas fluorescens | 50108 | 168 | 9.70 | 28712 | 0.96 |
| Agromyces medislanum | 20152 | 332 | 10.10 | 29896 | 1.00 |
| Cellulomonas cellulans | 43879 | 404 | 9.80 | 29008 | 0.97 |
| Brevibacterium liquefaciens | 20579 | 432 | 10.40 | 30784 | 1.03 |
| Leminorella grimontii | 5078 | 531 | 10.30 | 30488 | 1.02 |
| Rhodococcus luteus | 43673 | 626 | 10.60 | 31376 | 1.05 |

EXAMPLE 39

Example Directed to a Real-Time Quantitative PCR Method Making Use of Fluorescence Emitting Probes A description will be made about an Example of a real-time quantitative PCR method, the basic principle of which is to conduct quantitative PCR by using both prior art primers and fluorescence emitting probes according to the present invention and to conduct real-time monitoring of amplified products by the probes.

1) Experimental Procedures and Conditions

Preparation of Template DNA

After the cenome DNA of *Paracoccus denitrificans* DSM 413 was extracted by using "DNeasy™ Tissue Kit" (trade name, product of QIAGEN GmbH, Hilden, Germany), the 16S rRNA gene was amplified by conventional PCR while using a Primer set consisting of E1OF (AGAGTTTGATC-CTGGCTCAG: not modified with any fluorescent dye (SEQ ID NO: 84)) and E140OR(GGTTACCTTGTTACGACTT (SEQ ID NO: 85)). PCR amplification products were quantitated, respectively, by using "Pico Green dsDNA Quantitation Kit" (trade name, product of Molecular Probes, Inc., OR, U.S.A.), and a solution containing the 16S rRNA gene at 6 ng/μL was prepared.

Other Conditions

The base sequence of the fluorescence emitting probe was 5'CTAATCCTTT—(Texas Red)GGCGAT—(Dabcyl) AAATC3' (SEQ ID NO: 83) in which the $9^{th}$ T from the 5' end was modified with Texas Red and the $15^{th}$ from the 5' end was modified with Dabcyl. Modifications were conducted in a similar manner as in Example 7. In addition, the 3' end of the probe was phosphorylated to inhibit any extension from the 3' end. As a forward primer and a reverse primer, those employed in conventional PCR were used (E10F, E1400R) (namely, primers not modified with any fluorescent dye). As a real-time PCR apparatus, "cycler" (trade mark, manufactured by Bio-Rad Laboratories, Inc., CA, U.S.A.) was used.

For both of the conventional PCR method and the real-time quantitative PCR method, the following PCR conditions were employed: $1^{st}$ denature: 95° C., 120 seconds; denaturation: 95° C., 60 seconds; annealing: 56° C., 60 seconds; and extension: 72° C., 70 seconds. The concentration of Mg ions was set at 2 mM. dNTP was added to give a final concentration of 2.5 mM, respectively. As a Taq polymerase, "Gene Taq" (trade name, product of NIPPON GENE CO., LTD., Tokyo, Japan) was used. The primers were each added at 100 nM in terms of final concentration in both of the conventional PCR method and the real-time quantitative PCR method. The DNA solution was used as a standard template solution, and was added at concentrations of from 0.6 pg to 6 ng/reaction, respectively. Using as a template an amplified product of a 16S rRNA gene derived from *Paracoccus denitififcans* DSM 413 as prepared in the above-described manner, the template was added to the reaction system to give concentrations of from 0.6 pg to 6 ng/reaction, respectively. The fluorescence emitting primer was added at 50 nM. Measurement of fluorescence was conducted once after denature and once after annealing in each cycle. The emitting rate of fluorescence (%) was determined in a similar manner as in Example 38.

2) Results

The results of real-time monitoring of the amplified products by the fluorescent emitting probes are shown in FIG. 35. It has been found from this diagram that amplified products can be monitored by using fluorescence emitting probes. Further, a relation between the number of cycles required to reach a threshold and the count of initially-added DNA is illustrated in FIG. 35. As is readily appreciated from this diagram, it is understood that the number of cycles and the number of copies added initially is in a linear relation. Incidentally, the correlation coefficient at this time was 0.9993 ($R^2$=0.9993). Accordingly, it has been found from this diagram that the quantitation of initial copies of a target gene can be accurately achieved from the $n^{th}$ number of a cycle in which the threshold is reached.

From the above results, it has been proven that the determination of an initial concentration of a target nucleic acid (the number of copies of the target nucleic acid existed before amplification) is feasible by real-time quantitative PCR making use of fluorescence emitting probes.

EXAMPLE 40

Detection of Single Nucleotide Polymorphism by Using a Fluorescence Emitting Probe or a Fluorescence Quenching Probe Based on a specific example, a description will be made about a method for detecting single nucleotide polymorphism from a denaturation curve by using a fluorescence emitting probe or fluorescence quenching probe.

1) Experimental Procedures

As the fluorescence emitting probe, the same fluorescence emitting probe as that employed in Example 39 was used. As the fluorescence quenching probe, that having a similar base sequence as the fluorescence emitting probe and modified at the 5' end thereof with "BODIPY FL" was used {(BODIPY FL)-5'CTAATCCTTTGGCGATAAATC3' (SEQ ID NO: 83)}. The modification was conducted in a similar manner as in Example 8. Employed as targets were a base sequence ((5')GATTTATCGC CAAAGGATTA G(3') (SEQ ID NO: 86)), which was 100% complementary with above-described fluorescence emitting probe and fluorescence quenching probe, and a base sequence ((5')GATTTATCGT CAAAGGATTA G(3') (SEQ ID NO: 87)) complementary with above-described fluorescence emitting probe and fluorescence quenching probe except for the inclusion of single nucleotide polymorphism that the $10^{th}$ C from the 5' end was replaced by T. The probe was added to a final concentration of 100 nM. A synthesized target DNA was added to a final concentration of 400 nM. The composition of a hybridization solution was similar to that employed in Example 12. As the synthesized target DNA, one of two targets furnished for this Experiment was used. The experiment was conducted by adding the solution, which had been prepared beforehand under the above-described conditions, into a fluorescence measuring tube and heating the solution at 0.1° C./sec from 30° C. to 80° C., during which measurement of fluorescence was continuously conducted.

From the results of this fluorescence measurement, probe-target denaturation curves were prepared. An evaluation was made as to whether or not a sequence including single nucleotide polymorphism can be discriminated from a difference in the denaturation curves. As an experimental apparatus, "cycler" (trade mark, manufactured by Bio-Rad Laboratories, Inc., CA, U.S.A.) was employed. As fluorescence filters, a fluorescence filter for Texas Red provided by Bio-Rad Laboratories, Inc., CA, U.S.A. was used for the detection of fluorescence from the fluorescence emitting probe, and a fluorescence filter for FITC also provided by Bio-Rad Laboratories, Inc., CA, U.S.A. was employed for the detection of fluorescence from the fluorescence quenching probe.

2) Results

The results are diagrammatically shown in FIG. 36. It has been found from the diagram that for each of a fluorescence emitting probe and a fluorescence quenching probe, the Tm value of its denaturation curve with a target containing single nucleotide polymorphism is lower by about 10° C. than the Tm value of its denaturation curve with a 100% complementary target. This indicates that the existence or non-existence of a hydrogen bond as much as one base appeared as the above difference in Tm. From the foregoing, it has been proven that single nucleotide polymorphism can be easily distinguished by using a fluorescence emitting probe or a fluorescence quenching probe.

EXAMPLE 41

DNA Chip Making Use of Fluorescence Emitting Probes

Based on a specific example, a description will be made about a DNA chip making use of fluorescence emitting probes.

1) Experimental Procedures

Fluorescence emitting probes of the base sequences shown in Table 10 were prepared. All of them are fragmentary base sequences of human CYP21 gene, and contain SNPs in their base sequences.

As probe names, the SNPs ID numbers allotted by the Whitehead Institute (http://waldo.wi.mit.edu/cvar_snps/) were used as were. The synthesis process was similar to that in Example 7 except for the following two matters. (1) To the 5' end, an amino linker was introduced by using "5'-Amino-Modifier C12" (trade name, product of Glen Research Corporation, VA, U.S.A.). (2) Depending upon the base sequence of the probe, the modification with Texas Red was conducted using not only "Amino-Modifier C6 dT" but also "Amino-Modifier C6 dC" (trade name, product of Glen Research Corporation, VA, U.S.A.). The base sequences of the probes and the positions modified with Texas Red and Dabcyl in the probes are shown in Table 10. As target nucleic acids, those presented in Table 11 were used.

TABLE 10

| | Used Fluorescence Emitting Probes | | |
|---|---|---|---|
| Probe name | Base sequence (SNPs at the underlined position) | Position modified by Texas Red as counted from the 5' end (5' end base: $0^{th}$) | Position of Dabcyl as counted from the 5' end |
| WIAF-10544 | 5'CGCAGCCGA<u>G</u> CATGGAAGA3' (SEQ ID NO: 88) | 6 | 12 |
| WIAF-13038 | 5'CGCTGCTG<u>C</u>C CTCCGG3' (SEQ ID NO: 89) | 5 | 11 |
| WIAF-10600 | 5'AAGGGCAC<u>G</u>T GCACATGGC3' (SEQ ID NO: 90) | 9 | 15 |

TABLE 10-continued

Used Fluorescence Emitting Probes

| Probe name | Base sequence (SNPs at the underlined position) | Position modified by Texas Red as counted from the 5' end (5' end base: 0$^{th}$) | Position of Dabcyl as counted from the 5' end |
|---|---|---|---|
| WIAF-10579 | 5'CATCGTGGAG ATGCAGCTGA GG3' (SEQ ID NO: 91) | 5 | 11 |
| WIAF-10578 | 5'CCTGCAGCAT CATCTGTTAC CTCAC3' (SEQ ID NO: 92) | 10 | 16 |

TABLE 11

Base Sequences of Target Nucleic

| Probe name | Base sequence | Remarks |
|---|---|---|
| No.1 100% match target | 5'TCTTCCATGC TCGGCTGCG3' (SEQ ID NO: 93) | Not modified |
| No.1 1 mismatch target | 5'TCTTCCATGG TCGGCTGCG3' (SEQ ID NO: 94) | Not modified; mismatched at the underlined position |
| No.2 100% match target | 5'CCGGAGGGCA GCAGCG3' (SEQ ID NO: 95) | Not modified |
| No.2 1 mismatch target | 5'CCGGAGGACA GCAGCG3' (SEQ ID NO: 96) | Not modified; mismatched at the underlined position |
| No.3 100% match target | 5'GCCATGTGCA CGTGCCCTT3' (SEQ ID NO: 97) | Not modified |
| No.3 1 mismatch target | 5'GCCATGTGCA AGTGCCTT3' (SEQ ID NO: 98) | Not modified; mismatched at the underlined position |
| No.4 100% mismatch target | 5'GCCTGCCACG AGGCTCTCC3' (SEQ ID NO: 99) | Not modified |
| No.4 1 mismatch target | 5'GCCTGCCACC AGGCTCTCC3' (SEQ ID NO: 100) | Not modified; mismatched at the underlined position |
| No.5 100% match target | 5'GTGAGGTAAC AGATGATGCT GCAGG3' (SEQ ID NO: 101) | Not modified |
| No.5 1 mismatch target | 5'GTGAGGTAAC AGTTGATGCT GCAGG3' (SEQ ID NO: 102) | Not modified; mismatched at the underlines position |

Preparation of DNA Chip

Spotting was conducted by applying one spot per probe solution. Except for this, a DNA chip was prepared in a similar manner as in the above-described preparation of the DNA chip making use of the fluorescence quenching probes.

In each of the probes of the present invention fixed on a slide glass, fluorescence from Texas Red is quenched when the probe is not hybridized with a target nucleic acid but, when hybridized, emission of fluorescence substantially increases compared with the emission of fluorescence when not hybridized.

Detection or Determination Method of SNPs

A 100% match target mixture solution—which contained the five 100% targets at concentrations of 100 µM, respectively, in 50 mM THE buffer (pH 7.2)—was placed on the DNA chip prepared as described above. A 1 mismatch target mixture solution—which contained the five 1 mismatch targets at concentrations of 100 µM, respectively—was prepared likewise, and was placed on a DNA chip which was different from the DNA chip on which the 100% match target mixture solution was placed. Cover glasses were placed over those solutions and were sealed with a nail varnish to avoid leakage of the target nucleic acids. Therefore, the two DNA chips were prepared in total in this test. Each of those chips was continuously observed for the emission of fluorescence at varied temperatures, and denaturation curves with the targets were prepared.

Measuring Equipment

Detecting or determining equipment was similar to that illustrated in FIG. 13.

2) Results of the Experiment

The results of the experiment are illustrated in FIG. 37. It is understood from the diagram that in all the probes, the intensity of fluorescence increased as the temperature dropped. This indicates that each fluorescence emitting probe was hybridized with its corresponding target base sequence. It has therefore been demonstrated that a denaturation curve of the hybridization complex of a probe according to the present invention and a target nucleic acid can be easily monitored by the method of this invention. further, the difference in Tm value between a probe which matches 100% with a target nucleic acid and a probe which mismatches by one base with the target nucleic acid was as much as about 10° C. in this investigation, so that it was possible to easily distinguish these probes from each other from their denaturation curves. Accordingly, this experiment has demonstrated that the use of a DNA chip according to the present invention makes it possible to simultaneously practice an analysis of plural types of SNPs.

EXAMPLE 42

Gene Amplification and Real-Time Detection of Amplified Products on a DNA Chip on which Fluorescence Emitting Probes and Fluorescence Quenched Probes were Fixed Based on a specific example, a description will be made about a method for conducting gene amplification and also real-time monitoring of amplified products on a DNA chip with fluorescence emitting probes and florescence quenching probes fixed thereon. Further, detection of SNPs was conducted from denaturation curves between the amplified genes and the fluorescence emitting probes and fluorescence quenching probes.

1) Experimental Procedures (1) Fluorescence Emitting Probes

Fluorescence emitting probes and fluorescence quenching probes are shown in Table 12. They had the same base sequences as those employed in Example 41. The fluorescence emitting probes were used in a form phosphorylated at the 3' ends thereof. They were synthesized in a similar manner as in Example 41. The base sequences of the probes and the positions modified with Texas Red and Dabcyl in the probes are as indicated in Table 10.

(2) Fluorescence Quenching Probes

The base sequences of the fluorescence quenching probes are the same as those of the fluorescence emitting probes. To the 5' ends of the fluorescence quenching probes, an MMT amino linker was introduced using "5'-Amino-Modifier C12" (trade name, product of Glen Research Corporation, VA, U.S.A.). Subsequent to deprotection of TFA as a protecting group, the respective oligonucleotides were modified with "BODIPY FL" (trade name, product of Molecular Probes, Inc., OR, U.S.A.) via the amino linker. The fluorescence quenching probes were in a form phosphorylated at the 3' ends thereof. As target nucleic acids, those shown in Table 11 were used. Except for these, details of their purification and modification procedures were similar to those practiced in Example 8.

(3) Primers

As a forward primer, one having the base sequence of 5' CTTGGGGGGGCATATCTG3' (SEQ ID NO: 103) was used. As a reverse primer, on the other hand, one having the base sequence of 5' ACATCCGGCTTTGACTCTCTCT3' (SEQ ID NO: 104) was employed. This primer set can amplify a section (2509 bp) of the human CYP21 gene. The fluorescence emitting probes and the fluorescence quenching probes have base sequences 100% complementary with their corresponding, SNPs-free amplified products. It was, therefore, expected that the intensities of fluorescence from the fluorescent emitting probes and fluorescence quenching probes shown in Table 12 would increase with the corresponding amplified products.

Preparation of DNA Chip

On a slide glass, the individual probe solutions were spotted at a rate of one spot per probe solution. Except for this, a DNA chip was prepared in a similar manner as in the preparation of the DNA chip making use of the quenching probes.

Where a fluorescence emitting probe is fixed on a slide glass, fluorescence from Texas Red is quenched when the probe is not hybridized with a target nucleic acid. When hybridized, however, the emission of fluorescence substantially increases compared with the emission of fluorescence when not hybridized. Where a fluorescence quenching probe is fixed on a slide glass, conversely, "BODIPY FL" emits fluorescence when not hybridized with a target nucleic acid but, when hybridized, significantly quenches fluorescence compared with the emission of fluorescence when not hybridized.

Procedures of Real-Time Monitoring PCR

Using as a template the human genome employed in Example 28, PCR was conducted on the DNA chip while using the above-mentioned primers. PCR products were detected by the fixed fluorescence emitting probes or fluorescence emitting probes. The experiment was carried out using the equipment illustrated in FIG. 13. On the DNA chip with the fluorescence emitting probes and fluorescence emitting probes fixed thereon, a solution containing the primers, the template, Taq polymerase, dNTP, $MgCl_2$ and the like was placed. To avoid leakage of the solution, a cover glass was placed over the solution and sealed with a nail varnish. The chip was mounted on a transparent warming plate with a temperature control program stored therein, and a PCR reaction was conducted on the chip. Amplified products were detected in real time by tracking changes in fluorescence from the fixed fluorescence emitting probes and fluorescence quenched probes by the microscope shown in FIG. 13.

The first denature was conducted at 95° C. for 120 seconds, followed by PCR cycles under the following conditions: denaturation: 95° C./60 sec, annealing: 69° C./60 sec, and extension: 72° C./120 sec. As primer concentrations, the concentrations of the forward primer and reverse primer were both set at 0.5 μM in terms of final concentration. The template was added at a final concentration of 1.5 ng/μL. As the DNA polymerase, "Gene Taq™" (trade name, product of NIPPON GENE CO., LTD., Tokyo, Japan) was used at a concentration of 0.5 unit/20 μL. The concentration of Mg ions was set at 2 mM. dNTP was added to give a final concentration of 2.5 mM, respectively.

Preparation of Denaturation Curves

Denaturation curves between the fixed fluorescence emitting probes and fluorescence quenching probes and the PCR amplification products were prepared in a similar manner as in Example 41 to conduct detection of SNPs.

2) Results

The results of the experiment are shown in FIG. 38. It is understood from the diagram that in all the probes, the change in fluorescence increases with the number of cycle. It has, therefore, been demonstrated that gene amplification and real-time detection of the amplified products can be conducted at the same time by the method of the present invention. The results of the preparation of the denaturation curves of the hybridization complex the amplification products and the respective probes are shown in FIG. 39. It is appreciated from the diagram that in all the probes, a significant change in fluorescence was observed as the temperature became lower. This indicates that the fluorescence emitting probes and fluorescence quenching probes hybridized with the corresponding target base sequences. Accordingly, it has been ascertained to be possible to easily monitor the denaturation curves between the probes of the present invention and the target nucleic acids. The denaturation curves between the amplification product and the fluorescence emitting probe and fluorescence quenching probe WIAF-10600 are in substantial conformity with the denaturation curve between the artificially-synthesized, mismatch-free target and the WIAF-10600 probe as obtained in Example 41, thereby indicating that the human genome employed as a template in this Example is 100% complementary with the base sequence of the probe WIAF-10600.

The denaturation curves between the amplification product and the fluorescence emitting probe and fluorescence quenching probe WIAF-10578 are in substantial conformity with the denaturation curve between the artificially-synthesized, mismatch-free target and the WIAF-10578 probe as obtained in Example 41, thereby indicating that the human genome employed as a template in this Example contains a mismatch relative to the base sequence of the probe WIAF-105787. As can be appreciated from the foregoing, it has been found that use of a DNA chip according to the present invention makes it possible to simultaneously conduct an analysis of plural types of SNPs in an amplification product after a genetic amplification is conducted.

TABLE 12

Used Fluorescence Emitting Probes and Fluorescence Quenching Probes

| Probe name | Probe type | Sequence | Position modified by Texas Red as counted from the 5' end (5' end base: 0th) | Position of Dabcyl as counted from the 5' end |
|---|---|---|---|---|
| WIAF-10600-No. 1 | Fluorescence emitting probe | 5'AAGGGCACGT GCACATGGC3' (SEQ ID NO: 105) | 6 | 12 |
| WIAF-10578-No. 2 | Fluorescence emitting probe | 5'CCTGCAGCAT CATCTGTTAC CTCAC3' (SEQ ID NO: 106) | 5 | 11 |
| WIAF-10600-No. 3 | Fluorescence emitting probe | 5'AAGGGCACGT GCACATGGC3' (SEQ ID NO: 107) | 9 | 15 |
| WIAF-10579-No. 4 | Fluorescence emitting probe | 5'CCTGCAGCAT CATCTGTTAC CTCAC3' (SEQ ID NO: 108) | 5 | 11 |

---

The invention claimed is:

1. A method of determining the initial amounts of individual species of a target gene, comprising:
- amplifying a target gene and monitoring the amplification by real-time PCR;
- performing a polymorphous analysis with respect to the amplified target gene to determine a polymorphous composition ratio of individual species of the target gene; and
- determining the initial amount of the target gene from the percentage of a change in the intensity of fluoresence occurring as a result of hybridization of the nucleic acid probe to the amplified target gene; and
- determining the initial amounts of individual species of the target gene by multiplying the initial amount of the target gene by said polymorphous composition ratio of individual species of the target gene,
- wherein the real-time PCR is accomplished with a nucleic acid probe,
- wherein the probe comprises a single-stranded oligonucleotide capable of hybridizing to the target gene,
- wherein the probe is labeled with a fluorescent dye and a quencher substance,
- wherein the oligonucleotide is labeled with the fluorescent dye and the quencher substance such that the intensity of fluorescence in a hybridization reaction system increases when the probe is hybridized with the target gene, and
- wherein the oligonucleotide forms no stem-loop structure between bases at positions where the oligonucleotide is labeled with the fluorescent dye and the quencher substance.

2. The method of claim 1, wherein the polymorphous analysis is T-RFLP (terminal restriction fragment length polymorphism), RFLP (restriction fragment length polymorphism), SSCP (single strand conformation) or CFLP (cleavage fragment length polymorphism).

3. The method of claim 1, wherein the single-stranded oligonucleotide is labeled on the same nucleotide thereof with the fluorescent dye and the quencher substance.

4. The method of claim 1, wherein the distance between the bases at the positions where the oligonucleotide is labeled with the fluorescent dye and quencher substance, respectively, is 1 to 20 bases.

5. The method of claim 1, wherein the probe is labeled at a 3' end thereof with the fluorescent dye.

6. The method of claim 1, wherein the probe is labeled at a 5' end thereof with the fluorescent dye.

7. The method of claim 1, wherein the probe has G or C as a 5' end base and is labeled at the 5' end thereof with the fluorescent dye.

8. The method of claim 1, wherein a hydroxyl group on a 3' carbon of ribose or deoxyribose at the 3' end or a hydroxyl group on a 3' or 2' carbon of ribose at the 3' end has been phosphorylated.

9. The method of claim 1, wherein the probe is labeled at a 5' end phosphate group and/or a 3' end phosphate group thereof with the fluorescent dye.

10. The method of claim 1, wherein the oligonucleotide of the probe is a chemically-modified nucleic acid.

11. The method of claim 10, wherein the chemically-modified nucleic acid is 2'-O-methyloligonucleotide, 2'-O-ethyloligonucleotide, 2'-O-butyloligonucleotide, 2'-O-ethyleneoligonucleotide, or 2'-O-benzyl-oligonucleotide.

12. The method of claim 1, wherein the oligonucleotide of the probe is a chimeric oligonucleotide which comprises a ribonucleotide and a deoxyribonucleotide.

13. The method of claim 12, wherein the chimeric oligonucleotide comprises 2'-O-methyloligonucleotide, 2'-ethyloligonucleotide, 2'-O-butyloligonucleotide 2'-O-ethyleneoligonucleotide, or 2'-O-benzyl-oligonucleotide.

14. The method of claim 1, wherein said polymorphous analysis is T-RFLP.

15. The method of claim 14, wherein the amplified target gene is digested by making use of at least one endonuclease selected from Bso FI, Hha I, Hph I, Mn1 I, Rca I, Alu I and Msp I.

16. The method of claim 14, wherein said restriction endonuclease is at leat one endonuclease selected from Rca I, Alu I and Msp I.

17. The method of claim 15, wherein said endonuclease is Hha I.

18. The method of claim 1, wherein said quantitative real-time monitoring PCR method makes use of a nucleic acid probe labeled with a fluorescent dye and a quencher, wherein the fluorescent dye is one dye selected from FITC, EDANS, Texas red, 6-Joe, TMR, Alexa 488, Alexa 532, "BODIPY FL/C3", and "BODIPY FL/C6"; the quencher is one dye selected from Dabcyl, "QSY7", "QSY33", Ferrocene, methyl viologen, and N,N'dimethyl-2,9-diazopyrenium.

19. A method for determining the initial amounts of individual species of a target gene, comprising:
(1) amplifying a target gene and monitoring the amplification by a quantitative real-time PCR making use of a fluorescence-quenching probe labeled with a fluorescent dye at the 5'-end thereof as a primer(s);
(2) digesting the amplified target gene using an endonuclease;
(3) thermally modifying the obtained gene fragments into single-stranded forms
(4) detecting gene fragment(s) labeled with a fluorescent dye at the 5'-end thereof by a sequencer or HPLC by measuring a fluorescent emission in the fluorescent dye as a signaling marker;
(5) measuring the fluorescent intensity of fragment peaks detected by the sequencer or HPLC, which peaks are caused by the gene fragments,
and then, determining a composition ratio of individual fragments; and (6) determining the initial amount of the target gene from the percentage of a change in the intensity of fluorescence occurring as a result of hybridization of the nucleic acid probe to the amplified target gene; and (7) determining the initial amounts of individual species of the target gene by multiplying the initial amount of the target gene by said composition ratio of individual fragments, wherein said fluorescence-quenching probe is labeled at a phosphate group or a 5'-OH group of a ribose or deoxyribose which is obtained by dephosphorization of the 5'-end, and has a base sequence designed such that, when the probe hybridizes at the end portion thereof to the target nucleic acid, at least one G (guanine) base exists in a base sequence of the target gene at a portion 1 to 3 bases apart from end base of the target gene hybridized with the probe.

20. The method of claim 19, wherein the gene fragments obtaining by said digestion are analyzed and determined using a sequencer or HPLC.

* * * * *

SEQUENCE LISTING

<160> NUMBER OF SEQ ID NOS: 108

<210> SEQ ID NO 1
<211> LENGTH: 15
<212> TYPE: DNA
<213> ORGANISM: Artificial Sequence
<220> FEATURE:
<223> OTHER INFORMATION: Synthetic DNA

<400> SEQUENCE: 1 gggggaaaa aaaaa                                                        15

<210> SEQ ID NO 2
<211> LENGTH: 15
<212> TYPE: DNA
<213> ORGANISM: Artificial Sequence
<220> FEATURE:
<223> OTHER INFORMATION: Synthetic DNA

<400> SEQUENCE: 2
tttttttttc ccccc                                                       15

<210> SEQ ID NO 3
<211> LENGTH: 17
<212> TYPE: DNA
<213> ORGANISM: Artificial Sequence
<220> FEATURE:

-continued

```
<223> OTHER INFORMATION: Synthetic DNA

<400> SEQUENCE: 3
ctgcctcccg taggagt                                                  17

<210> SEQ ID NO 4
<211> LENGTH: 20
<212> TYPE: DNA
<213> ORGANISM: Artificial Sequence
<220> FEATURE:
<223> OTHER INFORMATION: Synthetic DNA

<400> SEQUENCE: 4
cccacatcgt tttgtctggg                                               20

<210> SEQ ID NO 5
<211> LENGTH: 30
<212> TYPE: DNA
<213> ORGANISM: Artificial Sequence
<220> FEATURE:
<223> OTHER INFORMATION: Synthetic DNA

<400> SEQUENCE: 5
atatatattt tttttgtttt tttttttttt                                    30

<210> SEQ ID NO 6
<211> LENGTH: 30
<212> TYPE: DNA
<213> ORGANISM: Artificial Sequence
<220> FEATURE:
<223> OTHER INFORMATION: Synthetic DNA

<400> SEQUENCE: 6
atatatattt tttttgttt tttttttttt                                     30

<210> SEQ ID NO 7
<211> LENGTH: 30
<212> TYPE: DNA
<213> ORGANISM: Artificial Sequence
<220> FEATURE:
<223> OTHER INFORMATION: Synthetic DNA

<400> SEQUENCE: 7
atatatattt ttttttgtt tttttttttt                                     30

<210> SEQ ID NO 8
<211> LENGTH: 30
<212> TYPE: DNA
<213> ORGANISM: Artificial Sequence
<220> FEATURE:
<223> OTHER INFORMATION: Synthetic DNA

<400> SEQUENCE: 8
atatatattt ttttttttgt tttttttttt                                    30

<210> SEQ ID NO 9
<211> LENGTH: 30
<212> TYPE: DNA
<213> ORGANISM: Artificial Sequence
<220> FEATURE:
<223> OTHER INFORMATION: Synthetic DNA

<400> SEQUENCE: 9
atatatattt tttttctttt tttttttttt                                    30
```

```
<210> SEQ ID NO 10
<211> LENGTH: 30
<212> TYPE: DNA
<213> ORGANISM: Artificial Sequence
<220> FEATURE:
<223> OTHER INFORMATION: Synthetic DNA

<400> SEQUENCE: 10
atatatattt ttttttcttt tttttttttt                                    30

<210> SEQ ID NO 11
<211> LENGTH: 30
<212> TYPE: DNA
<213> ORGANISM: Artificial Sequence
<220> FEATURE:
<223> OTHER INFORMATION: Synthetic DNA

<400> SEQUENCE: 11
atatatattt tttttttctt tttttttttt                                    30

<210> SEQ ID NO 12
<211> LENGTH: 30
<212> TYPE: DNA
<213> ORGANISM: Artificial Sequence
<220> FEATURE:
<223> OTHER INFORMATION: Synthetic DNA

<400> SEQUENCE: 12
atatatattt ttttttttct tttttttttt                                    30

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
atatatattt tttttttttc tttttttttt                                    30

<210> SEQ ID NO 14
<211> LENGTH: 18
<212> TYPE: DNA
<213> ORGANISM: Artificial Sequence
<220> FEATURE:
<223> OTHER INFORMATION: Synthetic DNA

<400> SEQUENCE: 14
aacaaaaaaa atatatat                                                 18

<210> SEQ ID NO 15
<211> LENGTH: 18
<212> TYPE: DNA
<213> ORGANISM: Artificial Sequence
<220> FEATURE:
<223> OTHER INFORMATION: Synthetic DNA

<400> SEQUENCE: 15
acaaaaaaaa atatatat                                                 18

<210> SEQ ID NO 16
<211> LENGTH: 18
<212> TYPE: DNA
<213> ORGANISM: Artificial Sequence
<220> FEATURE:
<223> OTHER INFORMATION: Synthetic DNA
```

```
<400> SEQUENCE: 16
caaaaaaaaa atatatat                                              18

<210> SEQ ID NO 17
<211> LENGTH: 18
<212> TYPE: DNA
<213> ORGANISM: Artificial Sequence
<220> FEATURE:
<223> OTHER INFORMATION: Synthetic DNA

<400> SEQUENCE: 17
aaaaaaaaaa atatatat                                              18

<210> SEQ ID NO 18
<211> LENGTH: 18
<212> TYPE: DNA
<213> ORGANISM: Artificial Sequence
<220> FEATURE:
<223> OTHER INFORMATION: Synthetic DNA

<400> SEQUENCE: 18
aagaaaaaaa atatatat                                              18

<210> SEQ ID NO 19
<211> LENGTH: 18
<212> TYPE: DNA
<213> ORGANISM: Artificial Sequence
<220> FEATURE:
<223> OTHER INFORMATION: Synthetic DNA

<400> SEQUENCE: 19
agaaaaaaaa atatatat                                              18

<210> SEQ ID NO 20
<211> LENGTH: 18
<212> TYPE: DNA
<213> ORGANISM: Artificial Sequence
<220> FEATURE:
<223> OTHER INFORMATION: Synthetic DNA

<400> SEQUENCE: 20
gaaaaaaaaa atatatat                                              18

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA

<400> SEQUENCE: 21
tatatatata tttttggggg                                            20

<210> SEQ ID NO 22
<211> LENGTH: 20
<212> TYPE: DNA
<213> ORGANISM: Artificial Sequence
<220> FEATURE:
<223> OTHER INFORMATION: Synthetic DNA

<400> SEQUENCE: 22
tatatatata tttttttgggg                                           20

<210> SEQ ID NO 23
<211> LENGTH: 20
```

```
<212> TYPE: DNA
<213> ORGANISM: Artificial Sequence
<220> FEATURE:
<223> OTHER INFORMATION: Synthetic DNA

<400> SEQUENCE: 23
tatatatata tttttttggg                                                     20

<210> SEQ ID NO 24
<211> LENGTH: 20
<212> TYPE: DNA
<213> ORGANISM: Artificial Sequence
<220> FEATURE:
<223> OTHER INFORMATION: Synthetic DNA

<400> SEQUENCE: 24
tatatatata ttttttttgg                                                     20

<210> SEQ ID NO 25
<211> LENGTH: 20
<212> TYPE: DNA
<213> ORGANISM: Artificial Sequence
<220> FEATURE:
<223> OTHER INFORMATION: Synthetic DNA

<400> SEQUENCE: 25
tatatatata tttttttttg                                                     20

<210> SEQ ID NO 26
<211> LENGTH: 20
<212> TYPE: DNA
<213> ORGANISM: Artificial Sequence
<220> FEATURE:
<223> OTHER INFORMATION: Synthetic DNA

<400> SEQUENCE: 26
tatatatata tttttccccc                                                     20

<210> SEQ ID NO 27
<211> LENGTH: 20
<212> TYPE: DNA
<213> ORGANISM: Artificial Sequence
<220> FEATURE:
<223> OTHER INFORMATION: Synthetic DNA

<400> SEQUENCE: 27
tatatatata ttttttcccc                                                     20

<210> SEQ ID NO 28
<211> LENGTH: 20
<212> TYPE: DNA
<213> ORGANISM: Artificial Sequence
<220> FEATURE:
<223> OTHER INFORMATION: Synthetic DNA

<400> SEQUENCE: 28
tatatatata tttttttccc                                                     20

<210> SEQ ID NO 29
<211> LENGTH: 20
<212> TYPE: DNA
<213> ORGANISM: Artificial Sequence
<220> FEATURE:
<223> OTHER INFORMATION: Synthetic DNA

<400> SEQUENCE: 29
```

```
tatatatata ttttttttcc                                          20
```

<210> SEQ ID NO 30
<211> LENGTH: 20
<212> TYPE: DNA
<213> ORGANISM: Artificial Sequence
<220> FEATURE:
<223> OTHER INFORMATION: Synthetic DNA

<400> SEQUENCE: 30

```
tatatatata tttttttttc                                          20
```

<210> SEQ ID NO 31
<211> LENGTH: 20
<212> TYPE: DNA
<213> ORGANISM: Artificial Sequence
<220> FEATURE:
<223> OTHER INFORMATION: Synthetic DNA

<400> SEQUENCE: 31

```
tatatatata tttttttttt                                          20
```

<210> SEQ ID NO 32
<211> LENGTH: 20
<212> TYPE: DNA
<213> ORGANISM: Artificial Sequence
<220> FEATURE:
<223> OTHER INFORMATION: Synthetic DNA

<400> SEQUENCE: 32

```
cccccaaaaa tatatatata                                          20
```

<210> SEQ ID NO 33
<211> LENGTH: 20
<212> TYPE: DNA
<213> ORGANISM: Artificial Sequence
<220> FEATURE:
<223> OTHER INFORMATION: Synthetic DNA

<400> SEQUENCE: 33

```
ccccaaaaaa tatatatata                                          20
```

<210> SEQ ID NO 34
<211> LENGTH: 20
<212> TYPE: DNA
<213> ORGANISM: Artificial Sequence
<220> FEATURE:
<223> OTHER INFORMATION: Synthetic DNA

<400> SEQUENCE: 34

```
cccaaaaaaa tatatatata                                          20
```

<210> SEQ ID NO 35
<211> LENGTH: 20
<212> TYPE: DNA
<213> ORGANISM: Artificial Sequence
<220> FEATURE:
<223> OTHER INFORMATION: Synthetic DNA

<400> SEQUENCE: 35

```
ccaaaaaaaa tatatatata                                          20
```

<210> SEQ ID NO 36
<211> LENGTH: 20
<212> TYPE: DNA
<213> ORGANISM: Artificial Sequence

```
<220> FEATURE:
<223> OTHER INFORMATION: Synthetic DNA

<400> SEQUENCE: 36
caaaaaaaaa tatatata                                                     20

<210> SEQ ID NO 37
<211> LENGTH: 20
<212> TYPE: DNA
<213> ORGANISM: Artificial Sequence
<220> FEATURE:
<223> OTHER INFORMATION: Synthetic DNA

<400> SEQUENCE: 37
gggggaaaaa tatatata                                                     20

<210> SEQ ID NO 38
<211> LENGTH: 20
<212> TYPE: DNA
<213> ORGANISM: Artificial Sequence
<220> FEATURE:
<223> OTHER INFORMATION: Synthetic DNA

<400> SEQUENCE: 38
ggggaaaaaa tatatata                                                     20

<210> SEQ ID NO 39
<211> LENGTH: 20
<212> TYPE: DNA
<213> ORGANISM: Artificial Sequence
<220> FEATURE:
<223> OTHER INFORMATION: Synthetic DNA

<400> SEQUENCE: 39
gggaaaaaaa tatatata                                                     20

<210> SEQ ID NO 40
<211> LENGTH: 20
<212> TYPE: DNA
<213> ORGANISM: Artificial Sequence
<220> FEATURE:
<223> OTHER INFORMATION: Synthetic DNA

<400> SEQUENCE: 40
ggaaaaaaaa tatatata                                                     20

<210> SEQ ID NO 41
<211> LENGTH: 20
<212> TYPE: DNA
<213> ORGANISM: Artificial Sequence
<220> FEATURE:
<223> OTHER INFORMATION: Synthetic DNA

<400> SEQUENCE: 41
gaaaaaaaaa tatatata                                                     20

<210> SEQ ID NO 42
<211> LENGTH: 20
<212> TYPE: DNA
<213> ORGANISM: Artificial Sequence
<220> FEATURE:
<223> OTHER INFORMATION: Synthetic DNA

<400> SEQUENCE: 42
aaaaaaaaaa tatatata                                                     20
```

<210> SEQ ID NO 43
<211> LENGTH: 18
<212> TYPE: DNA
<213> ORGANISM: Artificial Sequence
<220> FEATURE:
<223> OTHER INFORMATION: Synthetic DNA

<400> SEQUENCE: 43
cccccctttt tttttttt                                                   18

<210> SEQ ID NO 44
<211> LENGTH: 18
<212> TYPE: DNA
<213> ORGANISM: Artificial Sequence
<220> FEATURE:
<223> OTHER INFORMATION: Synthetic DNA

<400> SEQUENCE: 44
ggggggaaaa aaaaaaaa                                                   18

<210> SEQ ID NO 45
<211> LENGTH: 18
<212> TYPE: DNA
<213> ORGANISM: Artificial Sequence
<220> FEATURE:
<223> OTHER INFORMATION: Synthetic DNA

<400> SEQUENCE: 45 tttttteeee cccccccc                                                   18

<210> SEQ ID NO 46
<211> LENGTH: 18
<212> TYPE: DNA
<213> ORGANISM: Artificial Sequence
<220> FEATURE:
<223> OTHER INFORMATION: Synthetic DNA

<400> SEQUENCE: 46
aaaaaagggg gggggggg                                                   18

<210> SEQ ID NO 47
<211> LENGTH: 15
<212> TYPE: DNA
<213> ORGANISM: Artificial Sequence
<220> FEATURE:
<223> OTHER INFORMATION: Synthetic DNA

<400> SEQUENCE: 47
aaaaaaaaag ggggg                                                      15

<210> SEQ ID NO 48
<211> LENGTH: 15
<212> TYPE: DNA
<213> ORGANISM: Artificial Sequence
<220> FEATURE:
<223> OTHER INFORMATION: Synthetic DNA

<400> SEQUENCE: 48 ttttttttc ccccc                                                       15

<210> SEQ ID NO 49
<211> LENGTH: 15
<212> TYPE: DNA
<213> ORGANISM: Artificial Sequence
<220> FEATURE:
<223> OTHER INFORMATION: Synthetic DNA

<400> SEQUENCE: 49 gggggggga aaaaa                                              15

<210> SEQ ID NO 50
<211> LENGTH: 15
<212> TYPE: DNA
<213> ORGANISM: Artificial Sequence
<220> FEATURE:
<223> OTHER INFORMATION: Synthetic DNA

<400> SEQUENCE: 50
ccccccccct ttttt                                             15

<210> SEQ ID NO 51
<211> LENGTH: 35
<212> TYPE: DNA
<213> ORGANISM: Artificial Sequence
<220> FEATURE:
<223> OTHER INFORMATION: Synthetic DNA/RNA chimera

<400> SEQUENCE: 51
catccccacc ttcctccgag ttgaccccgg cagtc                       35

<210> SEQ ID NO 52
<211> LENGTH: 21
<212> TYPE: DNA
<213> ORGANISM: Artificial Sequence
<220> FEATURE:
<223> OTHER INFORMATION: Synthetic DNA

<400> SEQUENCE: 52
tcctttgagt tcccggccgg a                                      21

<210> SEQ ID NO 53
<211> LENGTH: 32
<212> TYPE: RNA
<213> ORGANISM: Artificial Sequence
<220> FEATURE:
<223> OTHER INFORMATION: Synthetic RNA

<400> SEQUENCE: 53
cccuggucgu aagggccaug augacuugac gu                          32

<210> SEQ ID NO 54
<211> LENGTH: 35
<212> TYPE: RNA
<213> ORGANISM: Artificial Sequence
<220> FEATURE:
<223> OTHER INFORMATION: Synthetic RNA

<400> SEQUENCE: 54
cauccccacc uuccuccgag uugaccccgg caguc                       35

<210> SEQ ID NO 55
<211> LENGTH: 17
<212> TYPE: RNA
<213> ORGANISM: Artificial Sequence
<220> FEATURE:
<223> OTHER INFORMATION: Synthetic RNA

<400> SEQUENCE: 55
ccuuccuccg aguugac                                           17

<210> SEQ ID NO 56

```
<211> LENGTH: 35
<212> TYPE: DNA
<213> ORGANISM: Artificial Sequence
<220> FEATURE:
<223> OTHER INFORMATION: Synthetic DNA

<400> SEQUENCE: 56
catccccacc ttcctccgag ttgaccccgg cagtc                                35

<210> SEQ ID NO 57
<211> LENGTH: 36
<212> TYPE: DNA
<213> ORGANISM: Artificial Sequence
<220> FEATURE:
<223> OTHER INFORMATION: Synthetic DNA

<400> SEQUENCE: 57
catccccacc ttcctctcgg cttatcaccg gcagtc                               36

<210> SEQ ID NO 58
<211> LENGTH: 19
<212> TYPE: DNA
<213> ORGANISM: Artificial Sequence
<220> FEATURE:
<223> OTHER INFORMATION: Synthetic DNA

<400> SEQUENCE: 58
cttttttttt ccccccccc                                                  19

<210> SEQ ID NO 59
<211> LENGTH: 19
<212> TYPE: DNA
<213> ORGANISM: Artificial Sequence
<220> FEATURE:
<223> OTHER INFORMATION: Synthetic DNA

<400> SEQUENCE: 59 tttcttttttt ccccccccc                                                 19

<210> SEQ ID NO 60
<211> LENGTH: 18
<212> TYPE: DNA
<213> ORGANISM: Artificial Sequence
<220> FEATURE:
<223> OTHER INFORMATION: Synthetic DNA

<400> SEQUENCE: 60
ggggggggaa aaaaaaag                                                   18

<210> SEQ ID NO 61
<211> LENGTH: 18
<212> TYPE: DNA
<213> ORGANISM: Artificial Sequence
<220> FEATURE:
<223> OTHER INFORMATION: Synthetic DNA

<400> SEQUENCE: 61
ggggggggaa aaagaaaa                                                   18

<210> SEQ ID NO 62
<211> LENGTH: 17
<212> TYPE: DNA
<213> ORGANISM: Artificial Sequence
<220> FEATURE:
<223> OTHER INFORMATION: Synthetic DNA

<400> SEQUENCE: 62
```

```
cggggggggt tttttt                                                    17

<210> SEQ ID NO 63
<211> LENGTH: 17
<212> TYPE: DNA
<213> ORGANISM: Artificial Sequence
<220> FEATURE:
<223> OTHER INFORMATION: Synthetic DNA

<400> SEQUENCE: 63
aaaaaaaacc cccccca                                                   17

<210> SEQ ID NO 64
<211> LENGTH: 17
<212> TYPE: DNA
<213> ORGANISM: Artificial Sequence
<220> FEATURE:
<223> OTHER INFORMATION: Synthetic DNA

<400> SEQUENCE: 64
aaaaaaaacc ccccccc                                                   17

<210> SEQ ID NO 65
<211> LENGTH: 17
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (17)..(17)
<223> OTHER INFORMATION: n = c, g, a, or t

<400> SEQUENCE: 65
aaaaaaaaac cccccccn                                                  17

<210> SEQ ID NO 66
<211> LENGTH: 17
<212> TYPE: DNA
<213> ORGANISM: Artificial Sequence
<220> FEATURE:
<223> OTHER INFORMATION: Synthetic DNA

<400> SEQUENCE: 66
aaaaaaaacc ccccccg                                                   17

<210> SEQ ID NO 67
<211> LENGTH: 50
<212> TYPE: DNA
<213> ORGANISM: Artificial Sequence
<220> FEATURE:
<223> OTHER INFORMATION: Synthetic DNA

<400> SEQUENCE: 67
aaacgatgtg ggaaggccca gacagccagg atgttggctt agaagcagcc               50

<210> SEQ ID NO 68
<211> LENGTH: 16
<212> TYPE: DNA
<213> ORGANISM: Artificial Sequence
<220> FEATURE:
<223> OTHER INFORMATION: Synthetic DNA

<400> SEQUENCE: 68
ccttcccaca tcgttt                                                    16
```

```
<210> SEQ ID NO 69
<211> LENGTH: 16
<212> TYPE: DNA
<213> ORGANISM: Artificial Sequence
<220> FEATURE:
<223> OTHER INFORMATION: Synthetic DNA

<400> SEQUENCE: 69
ccttcccata tcgttt                                                   16

<210> SEQ ID NO 70
<211> LENGTH: 16
<212> TYPE: DNA
<213> ORGANISM: Artificial Sequence
<220> FEATURE:
<223> OTHER INFORMATION: Synthetic DNA

<400> SEQUENCE: 70
ccttcccaaa tcgttt                                                   16

<210> SEQ ID NO 71
<211> LENGTH: 16
<212> TYPE: DNA
<213> ORGANISM: Artificial Sequence
<220> FEATURE:
<223> OTHER INFORMATION: Synthetic DNA

<400> SEQUENCE: 71
ccttcccaga tcgttt                                                   16

<210> SEQ ID NO 72
<211> LENGTH: 16
<212> TYPE: DNA
<213> ORGANISM: Artificial Sequence
<220> FEATURE:
<223> OTHER INFORMATION: Synthetic DNA

<400> SEQUENCE: 72
ccttccctga tcgttt                                                   16

<210> SEQ ID NO 73
<211> LENGTH: 16
<212> TYPE: DNA
<213> ORGANISM: Artificial Sequence
<220> FEATURE:
<223> OTHER INFORMATION: Synthetic DNA

<400> SEQUENCE: 73
ccttccctgt tcgttt                                                   16

<210> SEQ ID NO 74
<211> LENGTH: 19
<212> TYPE: DNA
<213> ORGANISM: Artificial Sequence
<220> FEATURE:
<223> OTHER INFORMATION: Synthetic DNA

<400> SEQUENCE: 74
catcgtttac ggcgtggac                                                19

<210> SEQ ID NO 75
<211> LENGTH: 19
<212> TYPE: DNA
<213> ORGANISM: Artificial Sequence
<220> FEATURE:
<223> OTHER INFORMATION: Synthetic DNA
```

<400> SEQUENCE: 75
ccagcagccg cggtaatac                                                    19

<210> SEQ ID NO 76
<211> LENGTH: 20
<212> TYPE: DNA
<213> ORGANISM: Artificial Sequence
<220> FEATURE:
<223> OTHER INFORMATION: Synthetic DNA

<400> SEQUENCE: 76
agagtttgat cctggctcag                                                   20

<210> SEQ ID NO 77
<211> LENGTH: 19
<212> TYPE: DNA
<213> ORGANISM: Artificial Sequence
<220> FEATURE:
<223> OTHER INFORMATION: Synthetic DNA

<400> SEQUENCE: 77
ggttaccttg ttacgactt                                                    19

<210> SEQ ID NO 78
<211> LENGTH: 14
<212> TYPE: DNA
<213> ORGANISM: Artificial Sequence
<220> FEATURE:
<223> OTHER INFORMATION: Synthetic DNA

<400> SEQUENCE: 78
cgggcggtgt gtac                                                         14

<210> SEQ ID NO 79
<211> LENGTH: 23
<212> TYPE: DNA
<213> ORGANISM: Artificial Sequence
<220> FEATURE:
<223> OTHER INFORMATION: Synthetic DNA

<400> SEQUENCE: 79
ctggtctcct taaacctgtc ttg                                               23

<210> SEQ ID NO 80
<211> LENGTH: 22
<212> TYPE: DNA
<213> ORGANISM: Artificial Sequence
<220> FEATURE:
<223> OTHER INFORMATION: Synthetic DNA

<400> SEQUENCE: 80
ggttggccaa tctactccca gg                                                22

<210> SEQ ID NO 81
<211> LENGTH: 18
<212> TYPE: DNA
<213> ORGANISM: Artificial Sequence
<220> FEATURE:
<223> OTHER INFORMATION: Synthetic DNA
<221> NAME/KEY: misc_feature
<222> LOCATION: (2)..(2)
<223> OTHER INFORMATION: n = c, g, i, a, or t

<400> SEQUENCE: 81
cntaacacat gcaagtcg                                                     18

<210> SEQ ID NO 82
<211> LENGTH: 19
<212> TYPE: DNA
<213> ORGANISM: Artificial Sequence
<220> FEATURE:
<223> OTHER INFORMATION: Synthetic DNA

<400> SEQUENCE: 82
ttgtacacac cgcccgtca                                              19

<210> SEQ ID NO 83
<211> LENGTH: 21
<212> TYPE: DNA
<213> ORGANISM: Artificial Sequence
<220> FEATURE:
<223> OTHER INFORMATION: Synthetic DNA

<400> SEQUENCE: 83
ctaatccttt ggccataaat c                                           21

<210> SEQ ID NO 84
<211> LENGTH: 20
<212> TYPE: DNA
<213> ORGANISM: Artificial Sequence
<220> FEATURE:
<223> OTHER INFORMATION: Synthetic DNA

<400> SEQUENCE: 84
agagtttgat cctggctcag                                             20

<210> SEQ ID NO 85
<211> LENGTH: 19
<212> TYPE: DNA
<213> ORGANISM: Artificial Sequence
<220> FEATURE:
<223> OTHER INFORMATION: Synthetic DNA

<400> SEQUENCE: 85
ggttaccttg ttacgactt                                              19

<210> SEQ ID NO 86
<211> LENGTH: 21
<212> TYPE: DNA
<213> ORGANISM: Artificial Sequence
<220> FEATURE:
<223> OTHER INFORMATION: Synthetic DNA

<400> SEQUENCE: 86
gatttatcgc caaaggatta g                                           21

<210> SEQ ID NO 87
<211> LENGTH: 21
<212> TYPE: DNA
<213> ORGANISM: Artificial Sequence
<220> FEATURE:
<223> OTHER INFORMATION: Synthetic DNA

<400> SEQUENCE: 87
gatttatcgt caaaggatta g                                           21

<210> SEQ ID NO 88
<211> LENGTH: 19
<212> TYPE: DNA
<213> ORGANISM: Artificial Sequence
<220> FEATURE:
<223> OTHER INFORMATION: Synthetic DNA

<400> SEQUENCE: 88
cgcagccgag catggaaca                                                    19

<210> SEQ ID NO 89
<211> LENGTH: 16
<212> TYPE: DNA
<213> ORGANISM: Artificial Sequence
<220> FEATURE:
<223> OTHER INFORMATION: Synthetic DNA

<400> SEQUENCE: 89
cgctgctgcc ctccgg                                                       16

<210> SEQ ID NO 90
<211> LENGTH: 19
<212> TYPE: DNA
<213> ORGANISM: Artificial Sequence
<220> FEATURE:
<223> OTHER INFORMATION: Synthetic DNA

<400> SEQUENCE: 90
aagggcacgt gcacatggc                                                    19

<210> SEQ ID NO 91
<211> LENGTH: 22
<212> TYPE: DNA
<213> ORGANISM: Artificial Sequence
<220> FEATURE:
<223> OTHER INFORMATION: Synthetic DNA

<400> SEQUENCE: 91
catcgtggag atgcagctga gg                                                22

<210> SEQ ID NO 92
<211> LENGTH: 25
<212> TYPE: DNA
<213> ORGANISM: Artificial Sequence
<220> FEATURE:
<223> OTHER INFORMATION: Synthetic DNA

<400> SEQUENCE: 92
cctgcagcat catctgttac ctcac                                             25

<210> SEQ ID NO 93
<211> LENGTH: 19
<212> TYPE: DNA
<213> ORGANISM: Artificial Sequence
<220> FEATURE:
<223> OTHER INFORMATION: Synthetic DNA

<400> SEQUENCE: 93
tcttccatgc tcggctgcg                                                    19

<210> SEQ ID NO 94
<211> LENGTH: 19
<212> TYPE: DNA
<213> ORGANISM: Artificial Sequence
<220> FEATURE:
<223> OTHER INFORMATION: Synthetic DNA

<400> SEQUENCE: 94
tcttccatgg tcggctgcg                                                    19

<210> SEQ ID NO 95

```
<211> LENGTH: 16
<212> TYPE: DNA
<213> ORGANISM: Artificial Sequence
<220> FEATURE:
<223> OTHER INFORMATION: Synthetic DNA

<400> SEQUENCE: 95
ccggagggca gcagcg                                                    16

<210> SEQ ID NO 96
<211> LENGTH: 16
<212> TYPE: DNA
<213> ORGANISM: Artificial Sequence
<220> FEATURE:
<223> OTHER INFORMATION: Synthetic DNA

<400> SEQUENCE: 96
ccggaggaca gcagcg                                                    16

<210> SEQ ID NO 97
<211> LENGTH: 19
<212> TYPE: DNA
<213> ORGANISM: Artificial Sequence
<220> FEATURE:
<223> OTHER INFORMATION: Synthetic DNA

<400> SEQUENCE: 97
gccatgtgca cgtgccctt                                                 19

<210> SEQ ID NO 98
<211> LENGTH: 19
<212> TYPE: DNA
<213> ORGANISM: Artificial Sequence
<220> FEATURE:
<223> OTHER INFORMATION: Synthetic DNA

<400> SEQUENCE: 98
gccatgtgca agtgccctt                                                 19

<210> SEQ ID NO 99
<211> LENGTH: 19
<212> TYPE: DNA
<213> ORGANISM: Artificial Sequence
<220> FEATURE:
<223> OTHER INFORMATION: Synthetic DNA

<400> SEQUENCE: 99
gcctgccacg aggctctcc                                                 19

<210> SEQ ID NO 100
<211> LENGTH: 19
<212> TYPE: DNA
<213> ORGANISM: Artificial Sequence
<220> FEATURE:
<223> OTHER INFORMATION: Synthetic DNA

<400> SEQUENCE: 100
gcctgccacc aggctctcc                                                 19

<210> SEQ ID NO 101
<211> LENGTH: 25
<212> TYPE: DNA
<213> ORGANISM: Artificial Sequence
<220> FEATURE:
<223> OTHER INFORMATION: Synthetic DNA

<400> SEQUENCE: 101
```
gtgaggtaac agatgatgct gcagg                                      25

<210> SEQ ID NO 102
<211> LENGTH: 25
<212> TYPE: DNA
<213> ORGANISM: Artificial Sequence
<220> FEATURE:
<223> OTHER INFORMATION: Synthetic DNA

<400> SEQUENCE: 102
gtgaggtaac agttgatgct gcagg                                      25

<210> SEQ ID NO 103
<211> LENGTH: 18
<212> TYPE: DNA
<213> ORGANISM: Artificial Sequence
<220> FEATURE:
<223> OTHER INFORMATION: Synthetic DNA

<400> SEQUENCE: 103 cttgggggggg catatctg                                             18

<210> SEQ ID NO 104
<211> LENGTH: 22
<212> TYPE: DNA
<213> ORGANISM: Artificial Sequence
<220> FEATURE:
<223> OTHER INFORMATION: Synthetic DNA

<400> SEQUENCE: 104
acatccggct ttgactctct ct                                         22

<210> SEQ ID NO 105
<211> LENGTH: 19
<212> TYPE: DNA
<213> ORGANISM: Artificial Sequence
<220> FEATURE:
<223> OTHER INFORMATION: Synthetic DNA

<400> SEQUENCE: 105
aagggcacgt gcacatggc                                             19

<210> SEQ ID NO 106
<211> LENGTH: 25
<212> TYPE: DNA
<213> ORGANISM: Artificial Sequence
<220> FEATURE:
<223> OTHER INFORMATION: Synthetic DNA

<400> SEQUENCE: 106
cctgcagcat catctgttac ctcac                                      25

<210> SEQ ID NO 107
<211> LENGTH: 19
<212> TYPE: DNA
<213> ORGANISM: Artificial Sequence
<220> FEATURE:
<223> OTHER INFORMATION: Synthetic DNA

<400> SEQUENCE: 107
aagggcacgt gcacatggc                                             19

<210> SEQ ID NO 108
<211> LENGTH: 25
<212> TYPE: DNA

```
<213> ORGANISM: Artificial Sequence
<220> FEATURE:
<223> OTHER INFORMATION: Synthetic DNA

<400> SEQUENCE: 108
cctgcagcat catctgttac ctcac                                              25
```